United States Patent
Vu et al.

(10) Patent No.: US 12,404,518 B2
(45) Date of Patent: Sep. 2, 2025

(54) EXPRESSION OF IPT7 FROM TSS PROMOTER INCREASES ROOT MASS AND CARBON SEQUESTRATION

(71) Applicant: Salk Institute for Biological Studies, La Jolla, CA (US)

(72) Inventors: Jessica Vu, La Jolla, CA (US); Xuelin Wu, La Jolla, CA (US); Joanne Chory, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 225 days.

(21) Appl. No.: 17/923,463

(22) PCT Filed: May 6, 2021

(86) PCT No.: PCT/US2021/031023
§ 371 (c)(1),
(2) Date: Nov. 4, 2022

(87) PCT Pub. No.: WO2021/226306
PCT Pub. Date: Nov. 11, 2021

(65) Prior Publication Data
US 2023/0203520 A1    Jun. 29, 2023

Related U.S. Application Data

(60) Provisional application No. 63/020,950, filed on May 6, 2020.

(51) Int. Cl.
*C12N 15/82* (2006.01)

(52) U.S. Cl.
CPC ..... *C12N 15/8262* (2013.01); *C12N 15/8243* (2013.01)

(58) Field of Classification Search
None
See application file for complete search history.

(56) References Cited

U.S. PATENT DOCUMENTS

| | | | |
|---|---|---|---|
| 2004/0177403 A1* | 9/2004 | Kakimoto et al. | ... C12N 9/1285 |
| 2009/0163729 A1 | 6/2009 | Li et al. | |
| 2012/0084885 A1 | 4/2012 | Alexandrov et al. | |
| 2013/0096032 A1 | 4/2013 | Bush et al. | |
| 2016/0333367 A1* | 11/2016 | Immanen et al. | . C12N 15/8261 |
| 2019/0185872 A1 | 6/2019 | Immanen et al. | |

FOREIGN PATENT DOCUMENTS

| | | |
|---|---|---|
| WO | WO-2007149583 A2 | 12/2007 |
| WO | WO-2008069878 A2 | 6/2008 |
| WO | WO-2008157827 A2 | 12/2008 |
| WO | WO-2017178150 A1 | 10/2017 |
| WO | WO-2018175900 A2 | 9/2018 |
| WO | WO-2021226306 A1 | 11/2021 |
| WO | WO-2022082020 A1 | 4/2022 |

OTHER PUBLICATIONS

Ali et al., A fruitful decade using synthetic promoters in the improvement of transgenic plants, 2019, Frontiers in Plant Science, vol. 10, pp. 1-14 (Year: 2019).*
Kakimoto et al., Pub. No. US2004/0177403, Pub. Date: Sep. 9, 2004, Seq ID No. 7 AtIPT7 coding sequence (Year: 2004).*
Kakimoto et al., Pub. No. US2004/0177403, Pub. Date: Sep. 9, 2004, Seq ID No. 8 AtIPT7 amino acid sequence (Year: 2004).*
Dello Ioio et al., A Phabulosa/Cytokinin Feedback Loop Controls Root Growth in *Arabidopsis*, 2012, Current Biology, vol. 22, pp. 1699-1704 (Year: 2012).*
Raines et al., The cytokinin response factors modulate root and shoot growth and promote leaf senescence in *Arabidopsis*, 2016, The Plant Journal, vol. 85, pp. 134-147 (Year: 2016).*
Peng et al., CYCP2;1 integrates genetic and nutritional information to promote meristem cell division in *Arabidopsis*, 2014, Developmental Biology, vol. 393(1), pp. 160-170 (Year: 2014).*
Amelung et al., "Towards a global-scale soil climate mitigation strategy," Nature Communications, 2020 11:5427, 10 pages.
Carrington et al., "Biochemical changes across a carbon saturation gradient: Lignin, cutin, and suberin decomposition and stabilization in fractionated carbon pools," Soil Biology and Biochemistry, 2012, vol. 47, pp. 179-190.
Chen and Melitz, "Cytokinin biosynthesis in a cell-free system from cytokinin-autotrophic tobacco tissue cultures," FEBS Letters, Nov. 1979, vol. 107, No. 1, pp. 15-20.
Coulson, High-performance searching of biosequence databases, Trends in Biotechnology, Mar. 1994, vol. 12, pp. 76-80.
Ejiri et al., "Some Accessions of Amazonian Wild Rice (*Oryza glumaepatula*) Constitutively Form a Barrier to Radial Oxygen Loss along Adventitious Roots under Aerated Conditions," Plants 2020, 9, 880, 13 pages.
Energy Futures Initiative, "From the Ground Up: Cutting-Edge Approaches for Land-Based Carbon Dioxide Removal," Dec. 2020, © 2020 Energy Futures Initiative, 48 pages.
Feng et al., "Molecular-level methods for monitoring soil organic matter responses to global climate change," Journal of Environmental Monitoring, 2011, 13: 1246-1254.
GenBank Accession No. ABY78886.1, isopentenyl transferase IPT7 [*Zea mays*], May 17, 2018, 1 page.
GenBank Accession No. AL035524.1, *Arabidopsis thaliana* DNA Chromosome 4, BAC Clone T13J8 (Essaii Project), Jul. 26, 2016, 33 pages.
GenBank Accession No. AVP26993.1, isopentenyl transferase [*Oryza sativa*], Mar. 25, 2018, 1 page.
GenBank Accession No. CDM82045.1, unnamed protein product [*Triticum aestivum*], Sep. 25, 2015, 2 pages.

(Continued)

*Primary Examiner* — Bratislav Stankovic
*Assistant Examiner* — Christina L Meadows
(74) *Attorney, Agent, or Firm* — Klarquist Sparkman, LLP

(57) ABSTRACT

The disclosure provides nucleic acid constructs that include a TPR-domain suppressor of STIMPY (TSS) promoter operably linked to an isopentenyl-transferase 7 (IPT7) coding sequence. The introduction of such a construct into a plant or plant cell generates transgenic plants having increased root mass and greater carbon sequestration capacity. Plants generated using the methods are provided. Such plants can include other desirable traits.

19 Claims, 12 Drawing Sheets
Specification includes a Sequence Listing.

(56) References Cited

OTHER PUBLICATIONS

GenBank Accession No. EU263130.1, *Zea mays* isopentenyl transferase IPT7 (IPT7) gene, complete cds, May 17, 2008, 2 pages.
GenBank Accession No. JN128581.1, Triticum aestivum isopentenyltransferase 7 (IPT7) mRNA, partial cds, Aug. 25, 2012, 2 pages.
GenBank Accession No. MF182112.1, *Oryza sativa* cultivar NAGINA22 isopentenyl transferase (IPT7) mRNA, complete cds, Mar. 25, 2018, 2 pages.
GenBank Accession No. NP_194540. myb domain protein 41 [*Arabidopsis thaliana*], Feb. 14, 2019, 3 pages.
GenBank Accession No. OAP02016.1, IPT7 [*Arabidopsis thaliana*], May 25, 2016, 2 pages.
Gou et al., "The MYB107 Transcription Factor Positively Regulates Suberin Biosynthesis," Plant Physiology, Feb. 2017, vol. 173, pp. 1045-1058.
Höfer et al., "The *Arabidopsis* cytochrome P450 CYP86A1 encodes a fatty acid omega-hydroxylase involved in suberin monomer biosynthesis," Journal of Experimental Botany, 2008, vol. 59, No. 9, pp. 2347-2360.
Huang, X., et al., "A tool for analyzing and annotating genomic sequences," Genomics, Nov. 15, 1997, vol. 46(1), pp. 37-45.
International Preliminary Report on Patentability for International Application No. PCT/US2021/031023 dated Nov. 17, 2022, 14 pages.
International Search Report and Written Opinion for International Application No. PCT/US2021/031023 dated Oct. 21, 2021, 21 pages.
Kasahara et al., "Distinct Isoprenoid Origins of cis- and trans-Zeatin Biosyntheses in *Arabidopsis*," J Biol Chem., Apr. 2, 2004, vol. 279, No. 14, pp. 14049-14054.
Kosma et al., "Analysis of aliphatic waxes associated with root periderm or exodermis from eleven plant species," Phytochemistry, Sep. 2015, vol. 117, pp. 351-362.
Kosma, et al., "AtMYB41 activates ectopic suberin synthesis and assembly in multiple plant species and cell types,". The Plant Journal, 2014, vol. 80. pp. 216-229.
Kosma et al., "Identification of an *Arabidopsis* Fatty Alcohol: Caffeoyl-Coenzyme A Acyltransferase Required for the Synthesis of Alkyl Hydroxycinnamates in Root Waxes," Plant Physiology, Sep. 2012, vol. 160, pp. 237-248.
Lal, R., "Sequestering Atmospheric Carbon Dioxide," Critical Reviews in Plant Science, 2009, 28:90-96.
Lashbrooke et al., "MYB107 and MYB9 Homologs Regulate Suberin Deposition in Angiosperms," The Plant Cell, Sep. 2016, vol. 28: 2097-2116.
Ma Q., et al., "Expression of Isopentenyl Transferase Gene (ipt) in Leaf and Stem Delayed Leaf Senescence Without Affecting Root Growth," Plant Cell Reports, Nov. 2009, vol. 28(11), pp. 1759-1765.
Mahmood et al., "Overexpression of ANAC046 Promotes Suberin Biosynthesis in Roots of *Arabidopsis thaliana*," Int. J. Mol. Sci. 2019, 20, 6117, 18 pages.
Miyawaki et al., "Expression of cytokinin biosynthetic isopentenyltransferase genes in *Arabidopsis*: tissue specificity and regulation by auxin, cytokinin, and nitrate," The Plant Journal (2004) 37: 128-138.
Miyawaki et al., "Roles of Arabidopsis ATP / ADP isopentenyltransferases and tRNA isopentenyltransferases in cytokinin biosynthesis," PNAS, Oct. 31, 2006, vol. 103, No. 44, pp. 16598-16603.
Molina et al., "Identification of an *Arabidopsis* Feruloyl-Coenzyme A Transferase Required for Suberin Synthesis," Plant Physiology, Nov. 2009, vol. 151, pp. 1317-1328.

NCBI Reference Sequence: NM_113267.3, *Arabidopsis thaliana* isopentenyltransferase 7 (IPT7), mRNA, Oct. 22, 2022, 3 pages.
Ogura et al., "Root System Depth in *Arabidopsis* is Shaped by EXOCYST70A3 via the Dynamic Modulation of Auxin Transport," Cell, Jul. 2019, 178, 400-412.
Poitout et al., "Responses to Systemic Nitrogen Signaling in *Arabidopsis* Roots Involve trans-Zeatin in Shoots," The Plant Cell, Jun. 2018, 30: 1243-1257.
Preston et al., "13C nuclear magnetic resonance spectroscopy with cross-polarization and magic-angle spinning investigation of the proximate-analysis fractions used to assess litter quality in decomposition studies," Canadian Journal of Botany, 1997, vol. 75, pp. 1601-1613.
Shukla et al., "Suberin plasticity to developmental and exogenous cues is regulated by a set of MYB transcription factors," bioRxiv, Jan. 27, 2021, 28 pages, preprint doi: https://doi.org/10.1101/2021.01.27.428267.
Skylar et al., "Stimpy Mediates Cytokinin Signaling During Shoot Meristem Establishment in *Arabidopsis* Seedlings," Development, Feb. 2010, vol. 137 (4), pp. 541-549.
Takei et al., "AtIPT3 is a Key Determinant of Nitrate-Dependent Cytokinin Biosynthesis in *Arabidopsis*," Plant Cell Physiol. (2004) 45(8): 1053-1062.
Vazquez et al., "Evolution of Arabidopsis MIR genes generates novel microRNA classes," Nucleic Acids Research, 2008, vol. 36, No. 20, pp. 6429-6438.
Vishwanath et al., "Suberin: biosynthesis, regulation, and polymer assembly of a protective extracellular barrier," Plant Cell Reports (2015) vol. 34, pp. 573-586.
Vysotskaia et al., "Effects of local induction of ipt-gene in roots on cytokinins content in leaf cells tobacco plants," Tsitologiia. 2014, vol. 56(11):816-21. Abstract Only, retrieved from https://pubmed.ncbi.nlm.nih.gov/25707208/.
Wei et al., "MYB41, MYB107, and MYC2 promote ABA-mediated primary fatty alcohol accumulation via activation of AchnFAR in wound suberization in kiwifruit," Horticulture Research (2020) 7:86, 10 pages.
Wei et al., "Three Transcription Activators of ABA Signaling Positively Regulate Suberin Monomer Synthesis by Activating Cytochrome P450 CYP86A1 in Kiwifruit," Frontiers in Plant Science (2020) 10:1650, 15 pages.
Winkler et al., "Insoluble alkyl carbon components in soils derive mainly from cutin and suberin," Organic Geochemistry, 2005, vol. 36, pp. 519-529.
Woo H.R., et al., "Plant Senescence: How Plants Know When and How to Die," Journal of Experimental Botany, Feb. 2018, vol. 69(4), pp. 715-718.
Yang et al., "Synergistic action of auxin and cytokinin mediates aluminum-induced root growth inhibition in *Arabidopsis*," EMBO Reports, 2017, 18(7):1213-1230.
Ye Z.H., et al., "Expression of an Auxin- and Cytokinin-Regulated Gene in Cambial Region in Zinnia," Proceedings of the National Academy of Sciences, Jul. 1994, vol. 91(14), pp. 6539-6543.
Jasinski et al., "KNOX Action in *Arabidopsis* is Mediated by Coordinate Regulation of Cytokinin and Gibberellin Activities", Current Biology, 15:1560-1565, 2005.
Tvorogova et al., "The WUSCHEL-related homeobox transcription factor MtWOX9-1 stimulates somatic embryogenesis in Medicago truncatula", Plant Cell, Tissue and Organ Culture (PCTOC), 138:517-527, 2019.
Extended European Search Report for EP21799896.2, dated May 8, 2024, 9 pages.
Dello Ioio et al., "A Phabulosa/Cytokinin Feedback Loop Controls Root Growth in *Arabidopsis*", Current Biology, 22(18):1699-1704, 2012.
Skylar et al., "Metabolic sugar signal promotes *Arabidopsis* meristematic proliferation via G2", Developmental Biology, 351:82-89, 2011.

* cited by examiner

FIG. 4
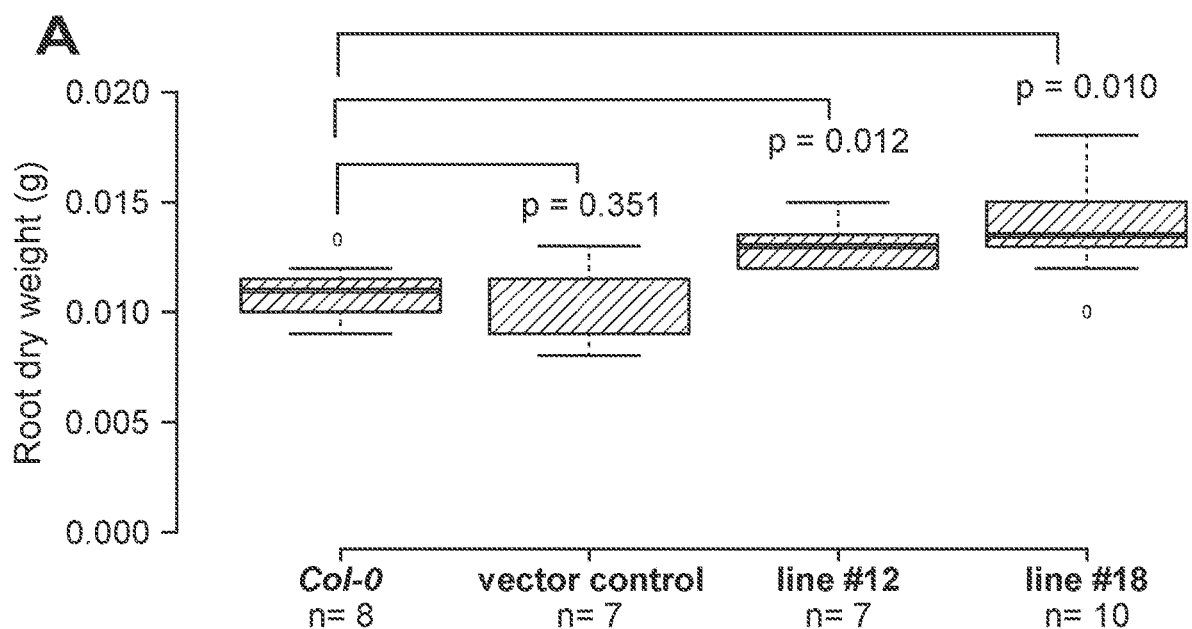
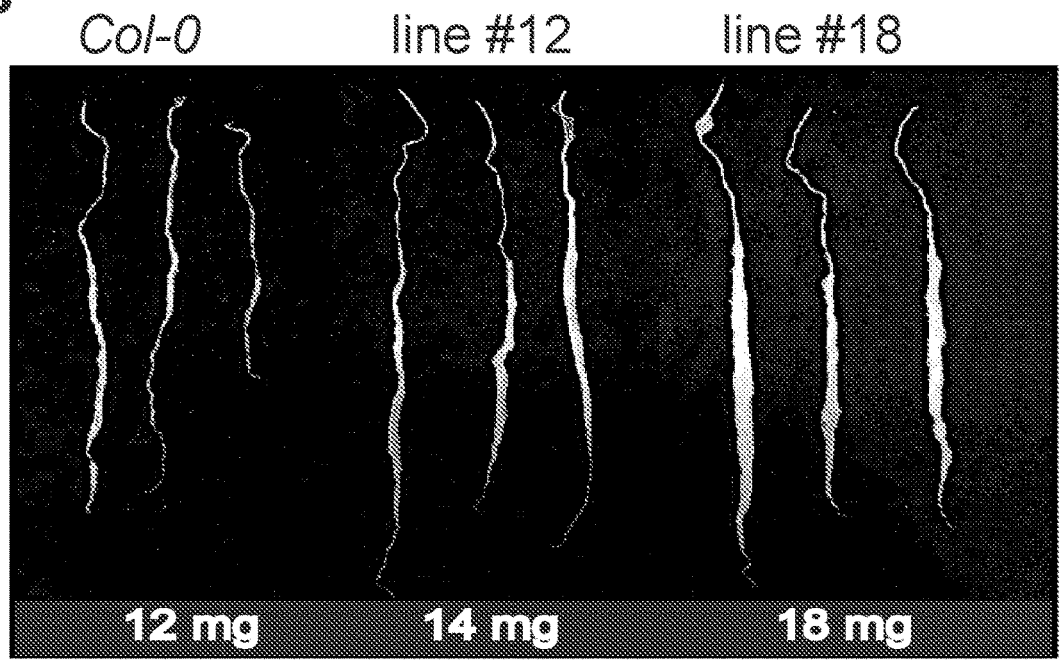

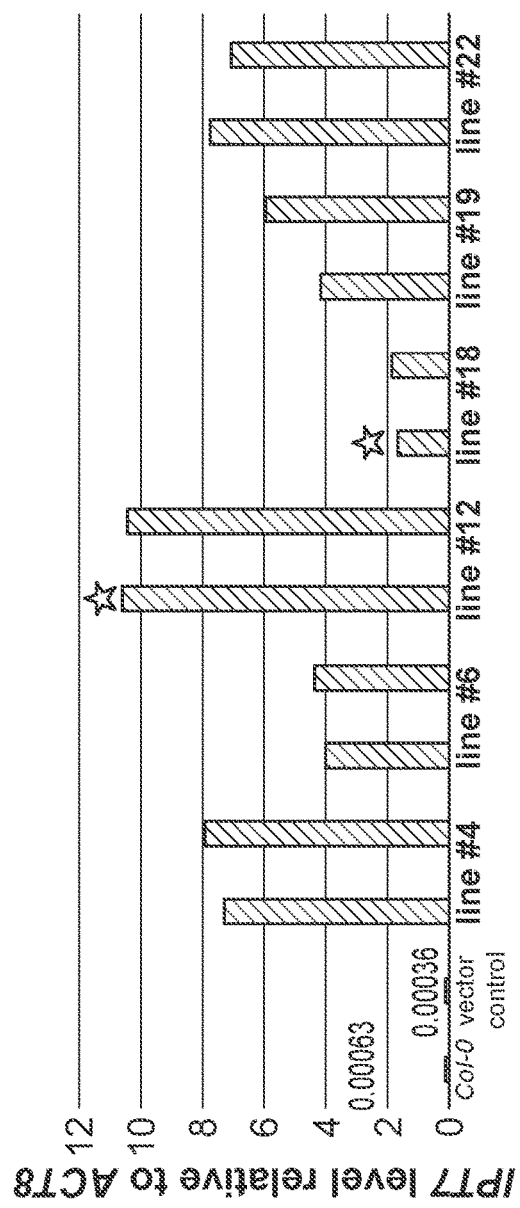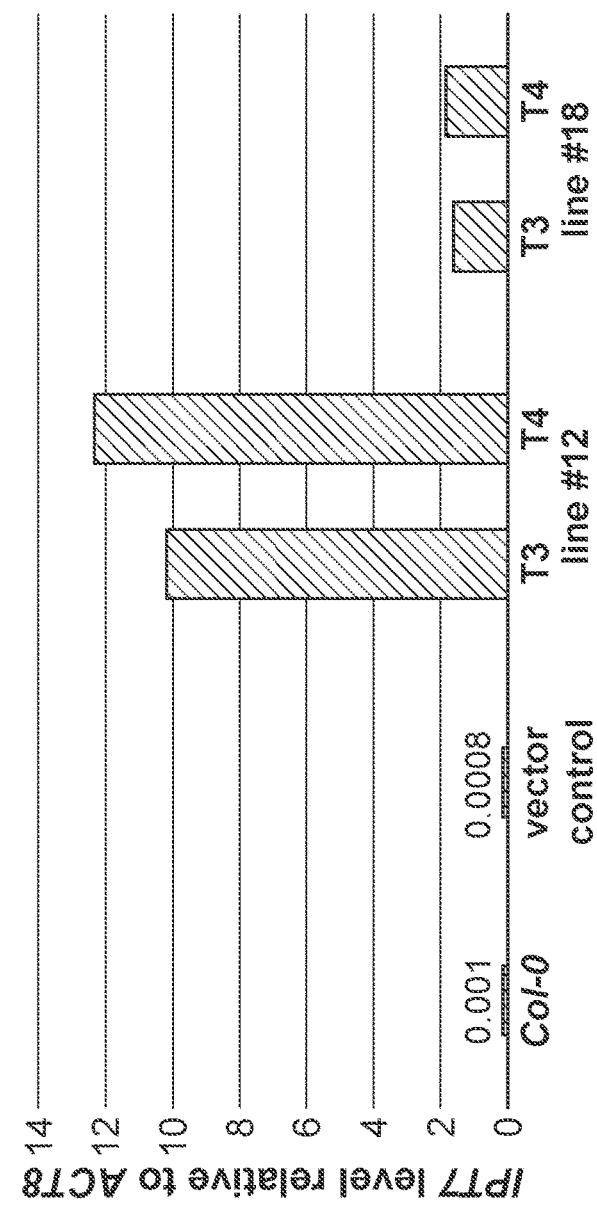
FIG. 6

FIG. 12

MKFSTSSLKQVQPTLCFKNKLSKVVNSFLHPKEK
VIFVMGATGSGKSRLAIDLATRFQGEIINSDKIQL
YKGLDVLTNKVTPKECRGVPHHLLGVEDSEAGNLT
ATQYSRLASQAISKLSANNKLPIVAGGSNSYIEAL
VNHSSGFLNNYDCCFIWDVSLPVLNSFVSKRVD
RMMEAGLLEEVREVFNPKANYSVGIRRAIGVPELH
EYLRNESLVDRATKSKMLDVAVKNIKKNTEILACR
QLKKIQRLHKKWKMSMHRVDATEVFLKRNVEEQDE
AWENLVARPSERIVDKFYNNQLKNDDVEHCIAA
SYGGGSRAHMI* (SEQ ID NO: 4)

SEQUENCE LISTING

<160> NUMBER OF SEQ ID NOS: 4

<210> SEQ ID NO 1
<211> LENGTH: 1643
<212> TYPE: DNA
<213> ORGANISM: Arabidopsis thaliana

<400> SEQUENCE: 1

```
ggacatttca tacacgttgg gccatatggc ccatatcaat gtatcattt  gtgttaggtt      60 ttatccactg gattctatgt caccttgaac atatattatt gctttgctca agctccccgt     120
gtctacgttc tgtcaagtag ttttccccctt tctcacatag atagctagat gccttatgca     180
tatcattcaa ttttaggctt catacgcgta aaaatggatt ttcaaaaaga gaaaaagaca     240
aagactcaag caaaatctag ggagccctca cgtggttcgt ctctactaat catggtctct     300
atatgctagg cttttttgtta gattagaaac ataacgcaaa gtcacatgat ggcacgtgtc     360
cgatcctaac aaatgtgata cttcctaaca gactcttgga aaattcctaa cgattgatat     420
catagcaaca tgttacattg taatttataa atcgatcgaa gaagaaaata attggatgta     480
cggtatcgga aaattcgaca atacataatt tgcgttgata aattaaagat ctatctatat     540
ggtagaaagc ttatattgga tgcttagttc caagcatgag tatcaatgta tcatgcatag     600
ggaatatctt tgacatgtaa acttttggtg ttatgcaatg atcattgtca aagaatgcca     660
ttcacaattt tacgaaggtg aagactacat atataaatgc tcgctaaggt tttgccaata     720
ctaatccgga aataaagtgt ttctgacgaa aagatctacc caaagatgta tgttagtaag     780
ttgcagcgca catgaatgga tccaattata tgtttgtcaa cgaaccaatt acgatcattt     840
```

```
caaaaaaaaa ataacgatca tttcttgaaa tcgtttttaa cgatgaagtg cgcaatttat      900
tttgtagacg gtaacaacca tgcaaataga attaaagaag aaaaataaac aaaaaaaaga      960
ctaatctaga cgaattaaaa aaaaaaaaaa actacacaaa tgaaattttg aaacttttg     1020 tttataattt tcttttgaaa attcaaaaat ttatgcttaa taatcttgtg gcaaaaaaag    1080
cccaaaagag ccaaaagtt cataaacacg aagatccata ctgtaaaata aactaaaata     1140
aattgataat aagatatgta aagtcatggg tgaaatctca aaaaatgatg aaaataaggg    1200
ggaaacatta aattaaattc aattgttcaa aaaaaggaa aaaatcatat agaaagatag     1260
aagaaaagat gaagttggtg atgaggtgtt aagaagcaa acaagaaat gagaggtctc      1320 aattttactt agcctcaaaa cactcttaag gagaatagaa gagagaatag cctcgcacct    1380
tatcctatcc tttctatctc tctctctata tctctatctc tattttctca atcactattt    1440
gacccctctc gtatcttatt tcctttact tcctcattgt caccaccact agtccctcat     1500
ttatacacac acacacacac acacacaccc ttctctcttc ttttttcctt ctatcttctt    1560
cttcctcacc cttcatctcc acttattcaa atacacactt cccctgccaa gtctttaggg   1620
atataattca atccaaggct agc                                            1643

<210> SEQ ID NO 2
<211> LENGTH: 1313
<212> TYPE: DNA
<213> ORGANISM: Arabidopsis thaliana

<400> SEQUENCE: 2
gacaactcac gactcgttga ggtgatctac cgcaaggact aaacaacaaa acatatattt       60
ttttgtccca acaaaaaaag tcaatcatca tgaagttctc aatctcatca ctgaagcagg      120
tacaaccaat cttgtgcttc aagaacaagc tatctaaggt caacgtcaac tcttttctcc      180
atcccaaaga aaaagtcatc tttgtgatgg gagctaccgg atcgggtaag tctcgtctcg      240
ccatcgacct agcaactcgt tttcaaggag agatcataaa ctccgacaag attcaacttt      300
acaagggcct agacgtccta acaaacaaag tcacccctaa agaatgccga ggcgtgcctc      360
accacttgct tggagtattc gactccgaag ccggaaacct aacggccacc cagtatagcc      420
gccttgcgtc acaagcaatc tcgaaactct cagcgaacaa caagcttccc atagtagccg      480
gtggatcaaa ctcttacatc gaagcacttg ttaatcattc ctcggggttt ttattaaaca      540
actacgattg ttgtttcatt tgggtcgacg tttccttacc cgtacttaac tcctttgtct      600
caaaacgtgt cgaccgcatg atggaagcag gattactcga agaagtaaga gaagtgttca      660
atccaaaagc gaattactcc gtagggatac gacgagctat cggagtcccc gagctccatg      720
aatatttacg taacgaatct ctagtggacc gtgccacaaa aagtaaaatg cttgacgtag      780
ccgttaaaaa tatcaaaaag aacactgaga ttttagcttg tcgacagtta aaaagattc      840 aacggcttca caagagtgg aagatgtcta tgcatcgtgt tgacgccact gaggtgttct      900
tgaaacgcaa cgtagaagaa caagacgagg cttgggagaa tcttgtagcg agaccaagcg      960
agagaatcgt cgataagttt tataataata ataaccaact gaaaaatgat gatgttgagc     1020
actgtttggc ggcatcttac ggcggaggaa gtggaagtag agcccacaat atgatatgaa     1080
aagttttgtc attgatcatg tgaagctttt tggagtgtga gattaaagat gagtctccaa     1140
gatttcgtat gtgtggtggt gattccacgg aggtttttc aacgtacagg tgtgacattt     1200
accccgagag aaaaaaacaa aaaagttttt tcttttttaag tgtttgtata gaagaagata    1260
```

```
ttcggttaat attaattgtt tgataccta t tgactacgag ttcacgataa ccg    1313
```

<210> SEQ ID NO 3
<211> LENGTH: 10169
<212> TYPE: DNA
<213> ORGANISM: Artificial Sequence
<220> FEATURE:
<223> OTHER INFORMATION: vector pMX202

<400> SEQUENCE: 3

```
ttgatcccga ggggaaccct gtggttggca tgcacataca aatggacgaa cggataaacc     60
ttttcacgcc cttttaaata tccgttattc taataaacgc tcttttctct taggtttacc    120
cgccaatata tcctgtcaaa cactgatagt ttaaactgaa ggcgggaaac gacaatctga    180
tccaagctca agctgctcta gccaatacgc aaaccgcctc tccccgcgcg ttggccgatt    240
cattaatgca gctggcacga caggtttccc gactggaaag cgggcagtga gcgcaacgca    300
attaatgtga gttagctcac tcattaggca ccccaggctt tacactttat gcttccggct    360
cgtatgttgt gtggaattgt gagcggataa caatttcaca caggaaacag ctatgaccat    420
gattacgaat tcgagctcgg tacccgggga tcctctagag tcgacctgca gagctttcgt    480
tcgtatcatc ggtttcgaca acgttcgtca agttcaatgc atcagtttca ttgcgcacac    540
accagaatcc tactgagttc gagtattatg cattgggaa acatgttttt cttgtaccat     600
ttgttgtgct tgtaatttac tgtgtttttt attcggtttt cgctatcgaa ctgtgaaatg    660
gaaatggatg gagaagagtt aatgaatgat atggtccttt tgttcattct caaattaata    720
ttatttgttt tttctcttat ttgttgtgtg ttgaatttga aaatataaga gatatgcaaa    780
cattttgttt tgagtaaaaa tgtgtcaaat cgtggcctct aatgaccgaa gttaatatga    840
ggagtaaaac acttgtagtt gtaccattat gcttattcac taggcaacaa atatattttc    900
agacctagaa aagctgcaaa tgttactgaa tacaagtatg tcctcttgtg ttttagacat    960
ttatgaactt tcctttatgt aattttccag aatccttgtc agattctaat cattgcttta   1020
taattatagt tatactcatg gatttgtagt tgagtatgaa atatttttt aatgcatttt    1080
atgacttgcc aattgattga caacatgcat caatcgaagc ttggcactgg ccgtcgtttt   1140
acaacgtcgt gactgggaaa accctggcgt tacccaactt aatcgccttg cagcacatcc   1200
cccttttcgcc agctggcgta atagcgaaga ggcccgcacc gatcgccctt cccaacagtt   1260
gcgcagcctg aatggcgaat gctagagcag cttgccaatc gaggccgacc aaccgcaagc   1320
gttgtcagtg ttgcaaagcg ctctgtgtgg gcctacttta attgcttcca gtgttaaatt   1380
ggcgaaaggc aataatatcg caaaatattg tgttgtaaaa tgtaattatg ttttaatttc   1440
atggaaatgt ttgagcataa ttttttattaa tgtactaaat tactgttttg ttaaatgcaa   1500
ttttgctttc tcgggatttt aatatcaaaa tctatttaga aatacacaat attttgttgc   1560
aggcttgctg gagaatcgat ctgctatcat aaaaattaca aaaaatttt atttgcctca   1620
attattttag gattggtatt aaggacgctt aaattatttg tcgggtcact acgcatcatt   1680
gtgattgaga agatcagcga tacgaaatat tcgtagtact atcgataatt tatttgaaaa   1740
ttcataagaa aagcaaacgt tacatgaatt gatgaaacaa tacaaagaca gataaagcca   1800
cgcacattta ggatattggc cgagattact gaatattgag taagatcacg gaatttctga   1860
caggagcatg tcttcaattc agcccaaatg gcagttgaaa tactcaaacc gccccatatg   1920
caggagcgga tcattcattg tttgtttggt tgcctttgcc aacatgggag tccaaggttt   1980
cagggaagct ggaattccgg ggtgggcgaa gaactccagc atgagatccc cgcgctggag   2040
```

```
gatcatccag ccggcgtccc ggaaaacgat tccgaagccc aacctttcat agaaggcggc    2100
ggtggaatcg aaatctcgtg atggcaggtt gggcgtcgct tggtcggtca tttcgaaccc    2160
cagagtcccg ctcagaagaa ctcgtcaaga aggcgataga aggcgatgcg ctgcgaatcg    2220
ggagcggcga taccgtaaag cacgaggaag cggtcagccc attcgccgcc aagctcttca    2280
gcaatatcac gggtagccaa cgctatgtcc tgatagcggt ccgccacacc cagccggcca    2340
cagtcgatga atccagaaaa gcggccattt tccaccatga tattcggcaa gcaggcatcg    2400
ccatgggtca cgacgagatc ctcgccgtcg gcatgcgcg ccttgagcct ggcgaacagt    2460
tcggctggcg cgagccctg atgctcttcg tccagatcat cctgatcgac aagaccggct    2520
tccatccgag tacgtgctcg ctcgatgcga tgtttcgctt ggtggtcgaa tgggcaggta    2580
gccggatcaa gcgtatgcag ccgccgcatt gcatcagcca tgatggatac tttctcggca    2640
ggagcaaggt gagatgacag gagatcctgc cccggcactt cgcccaatag cagccagtcc    2700
cttcccgctt cagtgacaac gtcgagcaca gctgcgcaag gaacgcccgt cgtggccagc    2760
cacgatagcc gcgctgcctc gtcctggagt tcattcaggg caccggacag gtcggtcttg    2820
acaaaaagaa ccgggcgccc ctgcgctgac agccggaaca cggcggcatc agagcagccg    2880
attgtctgtt gtgcccagtc atagccgaat agcctctcca cccaagcggc cggagaacct    2940
gcgtgcaatc catcttgttc aatcatgcga acgatccgg ggaattcgct agagtcgatt    3000
tggtgtatcg agattggtta tgaaattcag atgctagtgt aatgtattgg taatttggga    3060
agatataata ggaagcaagg ctatttatcc atttctgaaa aggcgaaatg gcgtcaccgc    3120
gagcgtcacg cgcattccgt tcttgctgta aagcgttgtt tggtacactt ttgactagcg    3180
aggcttggcg tgtcagcgta tctattcaaa agtcgttaat ggctgcggat caagaaaaag    3240
ttggaataga aacagaatac ccgcgaaatt caggcccggt tgccatgtcc tacacgccga    3300
aataaacgac caaattagta gaaaaataaa aactgactcg gatacttacg tcacgtcttg    3360
cgcactgatt tgaaaaatct caatataaac aaagacggcc acaagaaaaa accaaaacac    3420
cgatattcat taatcttatc tagtttctca aaaaaattca tatcttccac acgtgaaaat    3480
gccaatttct cagacctacc tcggctctgc gaaggccccc gctggtatca aaagttttta    3540
tttcatccga catggcgcga ccgacctcaa cgagaaggaa attgtcgtga acggtgagaa    3600
gctctggggc gtgcaaggtt ccggaacgaa catcggtctc aatgcaaaag gggaacgcca    3660
ggctctgttg gccctcgaa attcggcgtt aattcagtac attaaaaacg tccgcaatgt    3720
gttattaagt tgtctaagcg tcaatttgtt tacaccacaa tatatcctgc caccagccag    3780
ccaacagctc cccgaccggc agctcggcac aaaatcacca ctcgatacag gcagcccatc    3840
agtccgggac ggcgtcagcg ggagagccgt tgtaaggcgg cagactttgc tcatgttacc    3900
gatgctattc ggaagaacgg caactaagct gccgggtttg aaacacggat gatctcgcgg    3960
agggtagcat gttgattgta acgatgacag agcgttgctg cctgtgatca attcgggcac    4020
gaacccagtg gacataagcc tcgttcggtt cgtaagctgt aatgcaagta gcgtaactgc    4080
cgtcacgcaa ctggtccaga accttgaccg aacgcagcgg tggtaacggc gcagtggcgg    4140
ttttcatggc ttcttgttat gacatgtttt tttggggtac agtctatgcc tcgggcatcc    4200
aagcagcaag cgcgttacgc cgtgggtcga tgtttgatgt tatggagcag caacgatgtt    4260
acgcagcagg gcagtcgccc taaaacaaag ttaaacatca tggggaagc ggtgatcgcc    4320 gaagtatcga ctcaactatc agaggtagtt ggcgtcatcg agcgccatct cgaaccgacg    4380
```

```
ttgctggccg tacatttgta cggctccgca gtggatggcg gcctgaagcc acacagtgat    4440
attgatttgc tggttacggt gaccgtaagg cttgatgaaa caacgcggcg agctttgatc    4500
aacgaccttt tggaaacttc ggcttcccct ggagagagcg agattctccg cgctgtagaa    4560
gtcaccattg ttgtgcacga cgacatcatt ccgtggcgtt atccagctaa gcgcgaactg    4620
caatttggag aatggcagcg caatgacatt cttgcaggta tcttcgagcc agccacgatc    4680
gacattgatc tggctatctt gctgacaaaa gcaagagaac atagcgttgc cttggtaggt    4740
ccagcggcgg aggaactctt tgatccggtt cctgaacagg atctatttga ggcgctaaat    4800
gaaaccttaa cgctatggaa ctcgccgccc gactgggctg gcgatgagcg aaatgtagtg    4860
cttacgttgt cccgcatttg gtacagcgca gtaaccggca aaatcgcgcc gaaggatgtc    4920
gctgccgact gggcaatgga gcgcctgccg gcccagtatc agcccgtcat acttgaagct    4980
agacaggctt atcttggaca agaagaagat cgcttggcct cgcgcgcaga tcagttggaa    5040
gaatttgtcc actacgtgaa aggcgagatc accaaggtag tcggcaaata atgtctagct    5100
agaaattcgt tcaagccgac gccgcttcgc cggcgttaac tcaagcgatt agatgcacta    5160
agcacataat tgctcacagc caaactatca ggtcaagtct gcttttatta tttttaagcg    5220
tgcataataa gccctacaca aattgggaga tatatcatgc atgaccaaaa tcccttaacg    5280
tgagttttcg ttccactgag cgtcagaccc cgtagaaaag atcaaaggat cttcttgaga    5340 tcctttttt ctgcgcgtaa tctgctgctt gcaaacaaaa aaaccaccgc taccagcggt    5400
ggtttgtttg ccggatcaag agctaccaac tcttttttccg aaggtaactg gcttcagcag    5460
agcgcagata ccaaatactg tccttctagt gtagccgtag ttaggccacc acttcaagaa    5520
ctctgtagca ccgcctacat acctcgctct gctaatcctg ttaccagtgg ctgctgccag    5580
tggcgataag tcgtgtctta ccgggttgga ctcaagacga tagttaccgg ataaggcgca    5640
gcggtcgggc tgaacggggg gttcgtgcac acagcccagc ttggagcgaa cgacctacac    5700
cgaactgaga tacctacagc gtgagctatg agaaagcgcc acgcttcccg aagggagaaa    5760
ggcggacagg tatccggtaa gcggcagggt cggaacagga gagcgcacga gggagcttcc    5820
agggggaaac gcctggtatc tttatagtcc tgtcgggttt cgccacctct gacttgagcg    5880
tcgatttttg tgatgctcgt caggggggcg gagcctatgg aaaaacgcca gcaacgcggc    5940 cttttttacgg ttcctggcct tttgctggcc ttttgctcac atgttctttc ctgcgttatc    6000
ccctgattct gtggataacc gtattaccgc ctttgagtga gctgataccg ctcgccgcag    6060
ccgaacgacc gagcgcagcg agtcagtgag cgaggaagcg gaagagcgcc tgatgcggta    6120
ttttctcctt acgcatctgt gcggtatttc acaccgcata tggtgcactc tcagtacaat    6180
ctgctctgat gccgcatagt taagccagta tacactccgc tatcgctacg tgactgggtc    6240
atggctgcgc cccgacaccc gccaacaccc gctgacgcgc cctgacgggc ttgtctgctc    6300
ccggcatccg cttacagaca agctgtgacc gtctccggga gctgcatgtg tcagaggttt    6360
tcaccgtcat caccgaaacg cgcgaggcag ggtgccttga tgtgggcgcc ggcggtcgag    6420
tggcgacggc gcggcttgtc cgcgccctgg tagattgcct ggccgtaggc cagccatttt    6480
tgagcggcca gcgccgcgga taggccgacg cgaagcggcg gggcgtaggg agcgcagcga    6540
ccgaagggta ggcgcttttt gcagctcttc ggctgtgcgc tggccagaca gttatgcaca    6600
ggccaggcgg gttttaagag ttttaataag ttttaaagag ttttaggcgg aaaaatcgcc    6660
ttttttctct tttatatcag tcacttacat gtgtgaccgg ttcccaatgt acggctttgg    6720
gttcccaatg tacgggttcc ggttcccaat gtacggcttt gggttcccaa tgtacgtgct    6780
```

```
atccacagga aagagacctt ttcgaccttt ttccctgct agggcaattt gccctagcat   6840
ctgctccgta cattaggaac cggcggatgc ttcgccctcg atcaggttgc ggtagcgcat   6900
gactaggatc gggccagcct gccccgcctc ctccttcaaa tcgtactccg gcaggtcatt   6960
tgacccgatc agcttgcgca cggtgaaaca gaacttcttg aactctccgg cgctgccact   7020
gcgttcgtag atcgtcttga caaccatct ggcttctgcc ttgcctgcgg cgcggcgtgc    7080
caggcggtag agaaaacggc cgatgccggg atcgatcaaa aagtaatcgg ggtgaaccgt   7140
cagcacgtcc gggttcttgc cttctgtgat ctcgcggtac atccaatcag ctagctcgat   7200
ctcgatgtac tccggccgcc cggtttcgct ctttacgatc ttgtagcggc taatcaaggc   7260
ttcaccctcg ataccgtca ccaggcggcc gttcttggcc ttcttcgtac gctgcatggc    7320
aacgtgcgtg gtgtttaacc gaatgcaggt ttctaccagg tcgtctttct gcttccgcc    7380
atcggctcgc cggcagaact tgagtacgtc cgcaacgtgt ggacggaaca cgcggccggg   7440
cttgtctccc ttcccttccc ggtatcggtt catggattcg gttagatggg aaaccgccat   7500
cagtaccagg tcgtaatccc acacactggc catgccggcc ggccctgcgg aaacctctac   7560
gtgcccgtct ggaagctcgt agcggatcac ctcgccagct cgtcggtcac gcttcgacag   7620
acggaaaacg gccacgtcca tgatgctgcg actatcgcgg gtgcccacgt catagagcat   7680
cggaacgaaa aaatctggtt gctcgtcgcc cttgggcggc ttcctaatcg acggcgcacc   7740
ggctgccggc ggttgccggg attctttgcg gattcgatca gcggccgctt gccacgattc   7800
accggggcgt gcttctgcct cgatgcgttg ccgctgggcg gcctgcgcgg ccttcaactt   7860
ctccaccagg tcatcaccca gcgccgcgcc gatttgtacc gggccggatg gtttgcgacc   7920
gtcacgccga ttcctcgggc ttggggggttc cagtgccatt gcagggccgg cagacaaccc   7980
agccgcttac gcctggccaa ccgcccgttc ctccacacat ggggcattcc acggcgtcgg   8040
tgcctggttg ttcttgattt tccatgccgc ctcctttagc cgctaaaatt catctactca   8100
tttattcatt tgctcattta ctctggtagc tgcgcgatgt attcagatag cagctcggta   8160
atggtcttgc cttggcgtac cgcgtacatc ttcagcttgg tgtgatcctc cgccggcaac   8220
tgaaagttga cccgcttcat ggctggcgtg tctgccaggc tggccaacgt tgcagccttg   8280
ctgctgcgtg cgctcggacg gccggcactt agcgtgtttg tgcttttgct catttctct    8340
ttacctcatt aactcaaatg agttttgatt taatttcagc ggccagcgcc tggacctcgc   8400
gggcagcgtc gccctcgggt tctgattcaa gaacggttgt gccggcggcg gcagtgcctg   8460
ggtagctcac gcgctgcgtg atacgggact caagaatggg cagctcgtac ccggccagcg   8520
cctcggcaac ctcaccgccg atgcgcgtgc ctttgatcgc ccgcgacacg acaaaggccg   8580
cttgtagcct tccatccgtg acctcaatgc gctgcttaac cagctccacc aggtcggcg    8640
tggcccatat gtcgtaaggg cttggctgca ccggaatcag cacgaagtcg gctgccttga   8700
tcgcggacac agccaagtcc gccgcctggg gcgctccgtc gatcactacg aagtcgcgcc   8760
ggccgatggc cttcacgtcg cggtcaatcg tcggcggtc gatgccgaca acggttagcg    8820
gttgatcttc ccgcacggcc gcccaatcgc gggcactgcc ctggggatcg gaatcgacta   8880
acagaacatc ggccccggcg agttgcaggg cgcgggctag atgggttgcg atggtcgtct   8940
tgcctgaccc gccttctgg ttaagtacag cgataacctt catgcgttcc ccttgcgtat    9000
ttgtttattt actcatcgca tcatatacgc agcgaccgca tgcgcaagc tgttttactc    9060
aaatacacat cacctttta gacggcggcg ctcggtttct tcagcggcca agctggccgg    9120
```

```
ccaggccgcc agcttggcat cagacaaacc ggccaggatt tcatgcagcc gcacggttga      9180
gacgtgcgcg gcggctcga  acacgtaccc ggccgcgatc atctccgcct cgatctcttc      9240
ggtaatgaaa aacggttcgt cctggccgtc ctggtgcggt ttcatgcttg ttcctcttgg      9300
cgttcattct cggcggccgc cagggcgtcg gcctcggtca atgcgtcctc acggaaggca      9360
ccgcgccgcc tggcctcggt gggcgtcact tcctcgctgc gctcaagtgc gcggtacagg      9420
gtcgagcgat gcacgccaag cagtgcagcc gcctctttca cggtgcggcc ttcctggtcg      9480
atcagctcgc gggcgtgcgc gatctgtgcc ggggtgaggg tagggcgggg gccaaacttc      9540
acgcctcggg ccttggcggc ctcgcgcccg ctccgggtgc ggtcgatgat tagggaacgc      9600
tcgaactcgg caatgccggc gaacacggtc aacaccatgc ggccggccgg cgtggtggtg      9660
tcggcccacg gctctgccag gctacgcagg cccgcgccgg cctcctggat gcgctcggca      9720
atgtccagta ggtcgcgggt gctgcgggcc aggcggtcta gcctggtcac tgtcacaacg      9780
tcgccagggc gtaggtggtc aagcatcctg gccagctccg gcggtcgcg  cctggtgccg      9840 gtgatcttct cggaaaacag cttggtgcag ccggccgcgt gcagttcggc ccgttggttg      9900
gtcaagtcct ggtcgtcggt gctgacgcgg gcatagccca gcaggccagc ggcggcgctc      9960
ttgttcatgg cgtaatgtct ccggttctag tcgcaagtat tctactttat gcgactaaaa      10020
cacgcgacaa gaaaacgcca ggaaaagggc agggcggcag cctgtcgcgt aacttaggac      10080
ttgtgcgaca tgtcgttttc agaagacggc tgcactgaac gtcagaagcc gactgcacta      10140
tagcagcgga ggggttggat caaagtact                                       10169

<210> SEQ ID NO 4
<211> LENGTH: 329
<212> TYPE: PRT
<213> ORGANISM: Arabidopsis thaliana

<400> SEQUENCE: 4

Met Lys Phe Ser Ile Ser Ser Leu Lys Gln Val Gln Pro Ile Leu Cys
1               5                   10                  15

Phe Lys Asn Lys Leu Ser Lys Val Asn Val Asn Ser Phe Leu His Pro
            20                  25                  30

Lys Glu Lys Val Ile Phe Val Met Gly Ala Thr Gly Ser Gly Lys Ser
        35                  40                  45

Arg Leu Ala Ile Asp Leu Ala Thr Arg Phe Gln Gly Glu Ile Ile Asn
    50                  55                  60

Ser Asp Lys Ile Gln Leu Tyr Lys Gly Leu Asp Val Leu Thr Asn Lys
65                  70                  75                  80

Val Thr Pro Lys Glu Cys Arg Gly Val Pro His His Leu Leu Gly Val
                85                  90                  95

Phe Asp Ser Glu Ala Gly Asn Leu Thr Ala Thr Gln Tyr Ser Arg Leu
            100                 105                 110

Ala Ser Gln Ala Ile Ser Lys Leu Ser Ala Asn Asn Lys Leu Pro Ile
        115                 120                 125

Val Ala Gly Gly Ser Asn Ser Tyr Ile Glu Ala Leu Val Asn His Ser
    130                 135                 140

Ser Gly Phe Leu Asn Asn Tyr Asp Cys Cys Phe Ile Trp Val Asp
145                 150                 155                 160

Val Ser Leu Pro Val Leu Asn Ser Phe Val Ser Lys Arg Val Asp Arg
                165                 170                 175

Met Met Glu Ala Gly Leu Leu Glu Glu Val Arg Glu Val Phe Asn Pro
            180                 185                 190
```

```
Lys Ala Asn Tyr Ser Val Gly Ile Arg Arg Ala Ile Gly Val Pro Glu
        195                 200                 205

Leu His Glu Tyr Leu Arg Asn Glu Ser Leu Val Asp Arg Ala Thr Lys
    210                 215                 220

Ser Lys Met Leu Asp Val Ala Val Lys Asn Ile Lys Lys Asn Thr Glu
225                 230                 235                 240

Ile Leu Ala Cys Arg Gln Leu Lys Lys Ile Gln Arg Leu His Lys Lys
                245                 250                 255

Trp Lys Met Ser Met His Arg Val Asp Ala Thr Glu Val Phe Leu Lys
                260                 265                 270

Arg Asn Val Glu Glu Gln Asp Glu Ala Trp Glu Asn Leu Val Ala Arg
        275                 280                 285

Pro Ser Glu Arg Ile Val Asp Lys Phe Tyr Asn Asn Asn Asn Gln Leu
        290                 295                 300

Lys Asn Asp Asp Val Glu His Cys Leu Ala Ala Ser Tyr Gly Gly Gly
305                 310                 315                 320

Ser Gly Ser Arg Ala His Asn Met Ile
                325
```

EXPRESSION OF IPT7 FROM *TSS* PROMOTER INCREASES ROOT MASS AND CARBON SEQUESTRATION

CROSS-REFERENCE TO RELATED APPLICATION

This application is a U.S. national phase application of International PCT Application No. PCT/US2021/031023, filed May 6, 2021, which claims priority to, and the benefit of U.S. Provisional Patent Application No. 63/020,950, filed May 6, 2020, each of which is incorporated by reference herein in its entirety for all purposes.

SEQUENCE LISTING

The instant application contains a Sequence Listing which has been submitted electronically in ASCII format and is hereby incorporated by reference in its entirety. Said ASCII copy created on Nov. 3, 2022 is named "SALK_005_01US_SeqList_ST25.txt" and is 20,671 bytes in size.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 provides a TSS promoter nucleic acid sequence. SEQ ID NO: 2 provides an IPT7 cDNA nucleic acid sequence from *Arabidopsis*. Nucleic acid positions 1-89 are untranslated regions. SEQ ID NO: 3 provides the nucleic acid sequence of vector pMX202 (vector map provided in FIG. 11). SEQ ID NO: 4 provides an IPT7 protein sequence from *Arabidopsis*. FIG. 12 indicates the mitochondria transit peptide (yellow highlighting) and the unconserved amino acids as compared to other IPT proteins (red highlighting).

FIELD

The disclosure provides methods of making and using transgenic plants having increased root mass, for example without significant decreases in above-ground growth. Such plants over-express *Arabidopsis* isopentenyl-transferase 7 (IPT7) from the *Arabidopsis* TPR-domain suppressor of STIMPY (TSS) promoter, which results in expression of IPT7 in the mesophyll cells of developing leaves. Such plants can be used to increase root biomass, for example to increase underground carbon sequestration.

BACKGROUND

The growth and development of the above- and below-ground tissue of a plant is highly coordinated. One of the plant hormones that control this process is cytokinin, which is a family of adenine-derived compounds. Cytokinin regulates many aspects of plant development, including promoting cell division, enhancing photosynthetic rate, regulating carbon partitioning, and inhibiting leaf senescence. The exact role of cytokinin in a given organ is dependent on its developmental stage. For example, increased cytokinin in leaf primordia reduces leaf size, while in older leaves delays senescence and changes source-sink relationship between the older and the younger leaves. In addition, reduced cytokinin levels in the root increase root growth in plants.

The first and rate-limiting step of cytokinin biosynthesis is catalyzed by the adenosine phosphate-isopentenyltransferases (IPT). The function of the IPT proteins are highly conserved, as ectopic expression of the *Agrobacterium* IPT gene increased cytokinin content in many plant species. Nine IPT genes are found in *Arabidopsis thaliana*, and seven catalyze the formation of cytokinin.

SUMMARY

Methods of increasing carbon sequestration are needed. Provided herein are plants expressing isopentenyl-transferase 7 (IPT7) by the promoter of TPR-domain suppressor of STIMPY (TSS). TSS promoter allows specific expression of IPT7 in the mesophyll cells of developing leaves. Such transgenic plants have increased root mass, such as an increase of at least 10%, at least 15%, at least 18%, at least 20%, at least 25%, or at least 30%, as compared to no expression of the IPT7 from TSS promoter. This phenotype allows for carbon sequestration underground, without a cost to the above-ground growth. The increase in root biomass becomes more pronounced when the plants are older, possibly due to a mild delay of leaf senescence, providing additional carbon resources for continued root growth. Such plants may also have increased drought resistance (such as an increase of at least about 20%, at least 25%, at least 30%, at least 40%, at least 50%, at least 60%, at least 70%, at least 80%, at least 90%, at least 100%, at least 200%, at least 300%, at least 400% or at least 500%, as compared to a wild-type plant of the same species), increased yield (such as an increase of at least about 20%, at least 25%, at least 30%, at least 40%, at least 50%, at least 60%, at least 70%, at least 80%, at least 90%, at least 100%, at least 200%, at least 300%, at least 400% or at least 500%, as compared to a wild-type plant of the same species), or both.

Provided herein are isolated transgenic nucleic acid molecules, which include a TPR-domain suppressor of STIMPY (TSS) promoter operably linked to an isopentenyl-transferase 7 (IPT7) coding sequence. Such molecules can be referred to herein as TSS:IPT7 molecules or complexes. The IPT7 coding sequence can be endogenous or exogenous to the plant. In some examples, the TSS promoter has at least 80%, at least 90%, at least 95%, at least 96%, at least 97%, at least 98%, at least 99%, or 100% sequence identity SEQ ID NO: 1. In some examples, the IPT7 coding sequence has (1) at least 80%, at least 90%, at least 95%, at least 96%, at least 97%, at least 98%, at least 99%, or 100% sequence identity SEQ ID NO: 2, or (2) at least 80%, at least 90%, at least 95%, at least 96%, at least 97%, at least 98%, at least 99%, or 100% sequence identity nucleotides 90 to 1079 of SEQ ID NO: 2. In some examples, the IPT7 coding sequence encodes a protein having at least 80%, at least 90%, at least 95%, at least 96%, at least 97%, at least 98%, at least 99%, or 100% sequence identity SEQ ID NO: 4.

The TSS:IPT7 molecules can be part of a vector, such as a plasmid vector not found in plants. In one example, such a vector has at least 80%, at least 90%, at least 95%, at least 96%, at least 97%, at least 98%, at least 99%, or 100% sequence identity SEQ ID NO: 3.

Also provided are isolated transgenic plant cells, transgenic plant parts, and transgenic plants which include the TSS:IPT7 molecules, such as a vector including a TSS:IPT7 molecule. The disclosed transgenic plant cells, transgenic plant parts, and transgenic plants can further include one or more additional exogenous nucleic acid(s) encoding a protein(s) that confers upon the transgenic plant, transgenic plant part, or transgenic plant cell a desired trait, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism. The disclosed transgenic plant cells, transgenic plant parts, and transgenic plants can further include single locus conversion. Exemplary plant parts include a protoplast, leaf, stem, root, root tips, anther, pistil, stamen, seed, embryo, pollen, ovule, microspore, protoplast, sporophyte, gametophyte, cotyledon, hypocotyl, flower, shoot, tissue, petiole, or meristematic cell. In some examples, the transgenic plant cells, transgenic plant parts, and transgenic plants is or is from a dicot. Exemplary dicots include but are not limited to a canola, tobacco, legume (e.g., pea, bean, lentil, or peanut), daisy, mint, lettuce, tomato, woody tree (e.g., oak tree, maple tree, elm tree, apple tree, orange tree), rose bush, sunflower, or squash.

In some examples, the disclosed transgenic plants express at least about 10%, at least 20%, at least 25%, at least 30%, at least 40%, at least 50%, at least 60%, at least 70%, at least 80%, at least 90%, at least 100%, at least 200%, at least 300%, at least 400%, at least 500% or greater levels of IPT7 in mesophyll cells of developing leaves (such as at least 10-fold, at least 50-fold, at least 100-fold, at least 500-fold, or at least 1000-fold more) as compared to a wild-type plant. In some examples, a developing leaf has fully differentiated chloroplasts, may or may not be going through expansion, but has not entered senescence. In some examples, the disclosed transgenic plants have (1) at least about 5%, at least 6%, at least 7%, at least 8%, at least 9%, at least 10%, at least 11%, at least 12%, at least 13%, at least 14%, at least 15%, at least 16%, at least 17%, at least 18%, at least 19% or at least 20% more cells in the root meristematic zone at seedling stage as compared to a wild-type plant, (2) at least about 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29% or at least 30% greater root biomass as compared to a wild-type plant, (3) or no significant decrease in above ground growth as compared to a wild-type plant (e.g., as evidenced by days to flowering, rosette dry weight, or shoot dry weight), or (4) combinations thereof.

In some examples, the disclosed transgenic plants have an increased ability to sequester carbon in their roots, such as an increase of at least 20%, at least 40%, at least 50%, at least 60%, at least 70%, at least 80%, at least 90%, at least 95%, at least 100%, or at least 200% as compared to an amount of carbon sequestered by a native plant of the same species (e.g., a wild type native plant of the same species). Thus, methods of increasing carbon sequestration underground using the disclosed transgenic plants are provided.

Also provided are methods for increasing root mass in a plant. Such methods can include introducing a TSS:IPT7 molecule (or vector including such) into a plant cell, allowing the cell to develop into a plant (for example by cultivating the cell to form a cell culture, regenerating the cell culture to form a plant), and expressing IPT7 from the TSS promoter in mesophyll cells of developing leaves of the plant, thereby increasing root mass in the plant (for example by at least 10%, at least 15%, at least 20%, or at least 25%), in comparison to a wild type plant. Thus, in some examples, the methods include measuring root mass in the plant and in some examples comparing the measured root mass to a root mass observed with a wild type plant.

Also provided are methods for breeding a plant with increased root mass. Such methods can include crossing a transgenic plant provided herein that includes a TSS:IPT7 molecule (or vector including such) with a second plant, obtaining seed from the crossing, planting the seeds and growing the seeds to plants, and selecting from said plants those with increased root mass.

Also provided are methods for generating a plant with increased root mass. Such methods can include crossing a transgenic plant provided herein that includes a TSS:IPT7 molecule (or vector including such) with a second plant, thereby generating plants with increased root mass.

The present disclosure also provides isolated recombinant nucleic acid molecules, which comprise a TPR-domain suppressor of STIMPY (TSS) promoter operably linked to an isopentenyl-transferase (IPT) coding sequence, wherein the IPT coding sequence is modified to encode an IPT peptide that comprises amino acids 1-29 and 298-329 of SEQ ID NO: 4 at the corresponding positions in the unmodified IPT coding sequence. In some examples, the unmodified IPT coding sequence is a homolog, homeolog, ortholog or paralog of an IPT7 coding sequence that encodes the peptide of SEQ ID NO: 4.

The present disclosure further provides isolated recombinant nucleic acid molecules which comprise a TPR-domain suppressor of STIMPY (TSS) promoter operably linked to a modified isopentenyl-transferase 3 (IPT3) or a modified isopentenyl-transferase 4 (IPT4) coding sequence, wherein the coding sequence of the IPT3 or IPT4 nucleic acids have been modified to comprise nucleic acids encoding amino acids 1-29 and 298-329 of SEQ ID NO: 4 at the corresponding positions in unmodified IPT3 or IPT4 coding sequences, respectively.

The present disclosure also provides isolated recombinant nucleic acid molecules for expression in mesophyll cells in non-senescing leaves which comprise a promoter operably linked to an isopentenyl-transferase 7 (IPT7) coding sequence, wherein the promoter drives the expression of IPT7 in the mesophyll cells in non-senescing leaves.

This disclosure further provides isolated recombinant nucleic acid molecules for expression in mesophyll cells in non-senescing leaves which comprise a promoter operably linked to an isopentenyl-transferase (IPT) coding sequence, wherein the IPT coding sequence is modified to encode an IPT peptide that comprises amino acids 1-29 and 298-329 of SEQ ID NO: 4 at the corresponding positions in the unmodified IPT coding sequence; and wherein the promoter drives the expression of the IPT coding sequence in the mesophyll cells in non-senescing leaves.

The present disclosure also provides vectors comprising any of the above disclosed isolated recombinant nucleic acid molecules.

The present invention further provides plant cells, plant tissues, plant parts, seeds and/or whole plants comprising of any of the above such isolated recombinant nucleic acid molecules or vectors.

The present disclosure provides methods of modifying a nucleic acid sequences encoding an isopentenyl-transferase (IPT), said methods comprising substituting or otherwise altering the nucleic acid sequences so that they encode amino acids 1-29 and 298-329 of SEQ ID NO: 4 at the corresponding amino acid positions encoded by the unmodified IPT nucleic acid sequence. In some such methods, the unmodified IPT nucleic acid sequence is a homolog, homeolog, ortholog or paralog of an IPT7 nucleic acid sequence that encodes the peptide of SEQ ID NO: 4.

The present disclosure also provides isolated nucleic acid molecules comprising a TPR-domain suppressor of STIMPY (TSS) promoter. In some examples, the TSS promoter comprises at least 80%, at least 90%, at least 95%, at least 96%, at least 97%, at least 98%, at least 99%, or 100% sequence identity to SEQ ID NO: 1. The present disclosure also provides vectors comprising such isolated nucleic acid molecules. The present disclosure further provides isolated transgenic plant cells comprising such isolated nucleic acid molecules and vectors. The present disclosure provides transgenic plants, transgenic plant tissues or transgenic plant parts which comprise such isolated transgenic nucleic acid molecules, vectors, and/or plant cells.

The foregoing and other objects and features of the disclosure will become more apparent from the following detailed description, which proceeds with reference to the accompanying figures.

BRIEF DESCRIPTION OF THE DRAWINGS

FIGS. 4A-4B. TSS:IPT7 expression leads to increased root biomass in mature hydroponically grown *Arabidopsis*. (A) The root dry weight was measured in 6-week-old plants. The average root dry weight per plant for each genotype is: Col-0 (wildtype)—11 mg, vector control—10.1 mg, TSS:IPT7 line #12-13 mg (18% increase), TSS:IPT7 line #18- 13.7 mg (24% increase). (B) Images of fresh roots from 7-week-old hydroponically grown plants are shown. The increase in the size of the root bundle is visible and their average dry weight is marked below each genotype.

FIGS. 6A-6B. TSS:IPT7 expression is stable through generations in *Arabidopsis*. (A) IPT7 expression levels in six independent single-insertion homozygous T3 lines (i.e., lines #4, 6, 12, 18, 19 and 22) were compared to the vector control. Two sibling populations from each line were included in the analyses. The two lines that are marked with the stars were chosen for the analysis in T4 (i.e., TSS:IPT7 line #12 and TSS:IPT7 line #18). (B) IPT7 expression levels in the green tissues of 10-day-old seedlings were measured using RT-qPCR. Results from the T3 and T4 samples of two independent single-insertion homozygous lines are shown here compared to Col-0 (wildtype) and the vector control.

FIG. 12. Amino acid sequence of IPT7 (SEQ ID NO: 4) with the unique amino acids on either end highlighted. The first highlighted letters contain the mitochondria transit peptide. The second highlighted letters are the unconserved amino acids between IPT7 and other IPT proteins of the same subfamily.

DETAILED DESCRIPTION

I. Definitions

Figure 1:
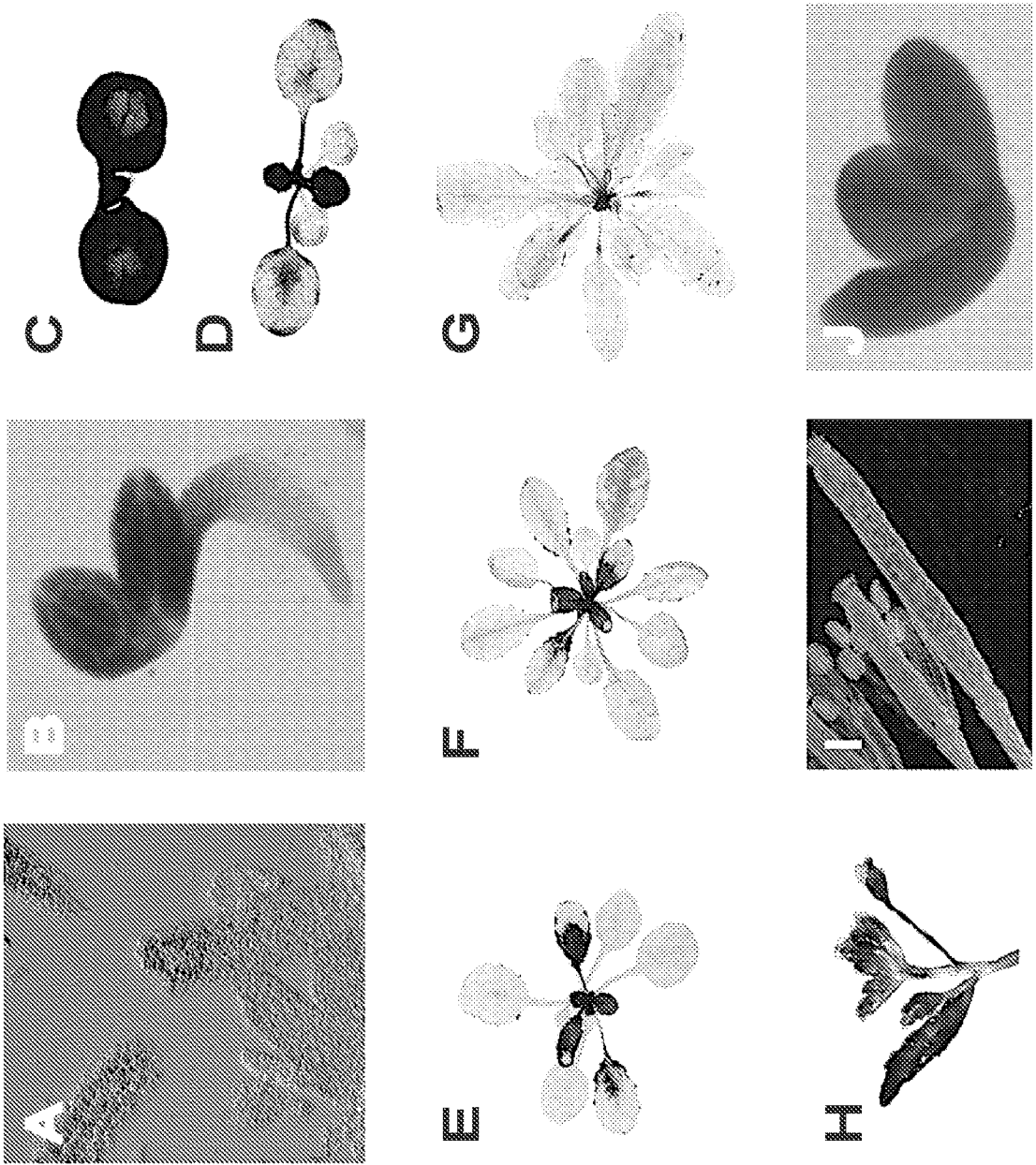
FIGS. 1A-1J. Expression pattern of TSS gene and TSS promoter-driven GUS activities in *Arabidopsis thaliana*. (A) In situ hybridization with an antisense TSS probe on a longitudinal section through the shoot apex of a 5-day-old seedling. TSS mRNA signal is displayed in a darker color code and is only found in the mesophyll cells of the young leaves. (B-J) TSS promoter GUS activity in 48 hour (B), 7-day-old (C) and 2-week-old (D) seedlings, 3-week (E), 4-week (F), and 6-week (G) rosette leaves, inflorescence (H), young siliques (I), and a walking-stick stage embryo (J). Tissues with GUS signal are displayed in a darker color code. The image in (B) shows clear exclusion of GUS activities from the vasculatures in the cotyledons.

Unless stated otherwise, all technical and scientific terms used herein have the same meaning as commonly understood by those of ordinary skill in the art to which the disclosure belongs. While the following terms are believed to be well understood by one of ordinary skill in the art, the following definitions are set forth to facilitate explanation of the presently disclosed subject matter. Although any methods and materials similar or equivalent to those described herein can be used in the practice or testing of the present disclosure, preferred methods and materials are described. The following terms are defined below. These definitions are for illustrative purposes and are not intended to limit the common meaning in the art of the defined terms.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

The terms and expressions, which have been employed herein, are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps. All GenBank® Accession numbers cited herein are incorporated by reference in their entirety for the sequence available on May 6, 2021.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers. As used herein, "comprising" is synonymous with "including," "containing," or "characterized by," and is inclusive or open-ended and does not exclude additional, un-recited elements or method steps. "Comprising A or B" means "including A" or "including B" or "including A and B." As used herein, "consisting of" excludes any element, step, or ingredient not specified in the aspect element. As used herein, "consisting essentially of" does not exclude materials or steps that do not materially affect the basic and novel characteristics of the aspect. In each instance herein, any of the terms "comprising", "consisting essentially of" and "consisting of" may be replaced with either of the other two terms. The disclosure illustratively described herein suitably may be practiced in the absence of any element or elements, limitation or limitations that is/are not specifically disclosed herein.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "at least a portion" or "fragment" of a nucleic acid or polypeptide means a portion having the minimal size characteristics of such sequences, or any larger fragment of the full-length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids. In some embodiments, a fragment of a polypeptide or polynucleotide comprises at least 10%, 20%, 30%, 40%, 50%, 60%, 70%, 80%, 90%, 95%, 96%, 97%, 98%, or 99% of the entire length of the reference polypeptide or polynucleotide. In some embodiments, a polypeptide or polynucleotide fragment may contain 5, 10, 15, 20, 25, 30, 35, 40, 45, 50, 60, 70, 80, 90, 100, 200, 300, 400, 500, 600, 700, 800, 900, 1000, 2000 or more nucleotides or amino acids.

As used herein, "cell" includes a plant cell, whether isolated, in tissue culture, or incorporated in a plant or plant part. In some examples, a cell includes a transgenic nucleic acid molecule, such as one not found in the cell in nature, such as a TSS:IPT7 nucleic acid molecule.

As used herein, the term "codon optimization" implies that the codon usage of a DNA or RNA is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism.

As used herein, the term "endogenous" or "endogenous gene," refers to the naturally occurring gene, in the location in which it is naturally found within the host cell genome. With reference to a nucleic acid or protein refers to the nucleic acid or protein in question as found in a plant in its natural form (i.e., without any human intervention). "Endogenous gene" is synonymous with "native gene" as used herein. An endogenous gene as described herein can include alleles of naturally occurring genes that have been mutated according to any of the methods of the present disclosure, i.e. an endogenous gene could have been modified at some point by traditional plant breeding methods and/or next generation plant breeding methods.

As used herein, a "vector" refers to a nucleic acid molecule into which a foreign nucleic acid molecule can be introduced without disrupting the ability of the vector to replicate and/or integrate in a host cell. In one example, a vector is not native to the cell into which it is introduced. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art.

A vector can include nucleic acid sequences that permit it to replicate in a host cell, such as an origin of replication. A vector can also include one or more selectable marker genes and other genetic elements known in the art. An integrating vector is capable of integrating itself into a host nucleic acid. An expression vector is a vector that contains the necessary regulatory sequences to allow transcription and translation of inserted gene or genes.

One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses).

As used herein, the term "exogenous" refers to a substance coming from some source other than its native source. For example, the terms "exogenous protein," or "exogenous gene" refer to a protein or gene from a non-native source, and that has been artificially supplied to a biological system. As used herein, the term "exogenous" is used interchangeably with the term "heterologous," and refers to a substance coming from some source other than its native source. As used herein with reference to a nucleic acid molecule, protein, vector, or cell, it refers to any such molecule, protein, vector, or cell, respectively, that does not originate from that particular cell or plant as found in nature. Thus, a non-naturally-occurring nucleic acid or vector is exogenous to a cell once introduced into the cell. An "exogenous" nucleic acid can either not occur in a plant in its natural form, be different from the nucleic acid in question as found in a plant in its natural form or can be identical to a nucleic acid found in a plant in its natural form but integrated not within their natural genetic environment.

In some examples, a transgenic plant/plant part/cell provided herein includes a TSS promoter (e.g., SEQ ID NO: 1) operably linked to an IPT7 coding sequence. Terms used herein as interchangeably and indicate the involvement of the hand of "man" (i.e., a human). The terms "non-naturally occurring" or "engineered", when referring to nucleic acid molecules or polypeptides indicate that the nucleic acid molecule or the polypeptide is at least substantially free from at least one other component with which they are naturally associated in nature and as found in nature. In addition, the terms can indicate that the nucleic acid molecules or polypeptides have a sequence not found in nature (such as a TSS: IPT7 construct).

A "recombinant" or "host cell" refers to a cell that has been genetically altered or is capable of being genetically altered by introduction of an exogenous polynucleotide, such as a recombinant plasmid or vector, such as one that expresses IPT7 from a TSS promoter. Typically, a host cell is a cell in which a vector can be propagated and its nucleic acid expressed. In specific examples, such cells are plant cells, such as from a dicot. The term also includes any progeny of the subject host cell. It is understood that all progeny may not be identical to the parental cell since there may be mutations that occur during replication. However, such progeny are included when the term "host cell" is used.

The terms "genetically engineered host cell," "recombinant host cell," and "recombinant strain" are used interchangeably herein and refer to host cells that have been genetically engineered by the methods of the present disclosure. Thus, the terms include a host cell (e.g., bacteria, yeast cell, fungal cell, CHO, human cell, plant cell, protoplast derived from plant, callus, etc.) that has been genetically altered, modified, or engineered, such that it exhibits an altered, modified, or different genotype and/or phenotype (e.g., when the genetic modification affects coding nucleic acid sequences), as compared to the naturally-occurring host cell from which it was derived. It is understood that the terms refer not only to the particular recombinant host cell in question, but also to the progeny or potential progeny of such a host cell.

As used herein, a "promoter" refers to an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some examples, a promoter used for recombinant expression of a nucleic acid molecule is not naturally occurring in the cell into which it is introduced, is not native to the nucleic acid molecule to which it is attached, or both. In one example, a promoter used is not endogenous (i.e., is exogenous) to the plant in which it is introduced. An exemplary promoter is the TSS promoter described herein (e.g., SEQ ID NO: 1).

As used herein, the term "heterologous" refers to a substance coming from some source or location other than its native source or location. In some embodiments, the term "heterologous nucleic acid" refers to a nucleic acid sequence that is not naturally found in the particular organism. For example, the term "heterologous promoter" may refer to a promoter that has been taken from one source organism and utilized in another organism, in which the promoter is not naturally found. However, the term "heterologous promoter" may also refer to a promoter that is from within the same source organism, but has merely been moved to a novel location, in which said promoter is not normally located.

Heterologous gene sequences can be introduced into a target cell by using an "expression vector," which can be a eukaryotic expression vector, for example a plant expression vector. Methods used to construct vectors are well known to a person skilled in the art and described in various publications. In particular, techniques for constructing suitable vectors, including a description of the functional components such as promoters, enhancers, termination and polyadenylation signals, selection markers, origins of replication, and splicing signals, are reviewed in the prior art. Vectors may include but are not limited to plasmid vectors, phagemids, cosmids, artificial/mini-chromosomes (e.g. ACE), or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif. In one embodiment the expression vector comprises at least one nucleic acid sequence which is a regulatory sequence necessary for transcription and translation of nucleotide sequences that encode for a peptide/polypeptide/ protein of interest.

As used herein, the term "naturally occurring" as applied to a nucleic acid, a polypeptide, a cell, or an organism, refers to a nucleic acid, polypeptide, cell, or organism that is found in nature. The term "naturally occurring" may refer to a gene or sequence derived from a naturally occurring source. Thus, for the purposes of this disclosure, a "non-naturally occurring" sequence is a sequence that has been synthesized, mutated, engineered, edited, or otherwise modified to have a different sequence from known natural sequences. In some embodiments, the modification may be at the protein level (e.g., amino acid substitutions). In other embodiments, the modification may be at the DNA level (e.g., nucleotide substitutions).

As used herein, the term "nucleotide change" or "nucleotide modification" refers to, e.g., nucleotide substitution, deletion, and/or insertion, as is well understood in the art. For example, such nucleotide changes/modifications include mutations containing alterations that produce silent substitutions, additions, or deletions, but do not alter the properties or activities of the encoded protein or how the proteins are made. As another example, such nucleotide changes/modifications include mutations containing alterations that produce replacement substitutions, additions, or deletions, that alter the properties or activities of the encoded protein or how the proteins are made.

As used herein, the term "protein modification" refers to, e.g., amino acid substitution, amino acid modification, deletion, and/or insertion, as is well understood in the art.

The term "next generation plant breeding" refers to a host of plant breeding tools and methodologies that are available to today's breeder. A key distinguishing feature of next generation plant breeding is that the breeder is no longer confined to relying upon observed phenotypic variation, in order to infer underlying genetic causes for a given trait. Rather, next generation plant breeding may include the utilization of molecular markers and marker assisted selection (MAS), such that the breeder can directly observe movement of alleles and genetic elements of interest from one plant in the breeding population to another and is not confined to merely observing phenotype. Further, next generation plant breeding methods are not confined to utilizing natural genetic variation found within a plant population. Rather, the breeder utilizing next generation plant breeding methodology can access a host of modern genetic engineering tools that directly alter/change/edit the plant's underlying genetic architecture in a targeted manner, in order to bring about a phenotypic trait of interest. In aspects, the plants bred with a next generation plant breeding methodology are indistinguishable from a plant that was bred in a traditional manner, as the resulting end product plant could theoretically be developed by either method. In particular aspects, a next generation plant breeding methodology may result in a plant that comprises: a genetic modification that is a deletion or insertion of any size; a genetic modification that is one or more base pair substitution; a genetic modification that is an introduction of nucleic acid sequences from within the plant's natural gene pool (e.g. any plant that could be crossed or bred with a plant of interest) or from editing of nucleic acid sequences in a plant to correspond to a sequence known to occur in the plant's natural gene pool; and offspring of said plants.

As used herein, the term "operably linked" refers to the association of nucleic acid sequences on a single nucleic acid fragment so that the function of one is regulated by the other. Thus, "operably linked" refers to a first nucleic acid sequence being operably linked with a second nucleic acid sequence when the first nucleic acid sequence is placed in a functional relationship with the second nucleic acid sequence. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA. For instance, a promoter (such as TSS) is operably linked to a nucleic acid sequence (such as an IPT7 coding sequence) if the promoter affects the transcription or expression of the nucleic acid sequence. Generally, operably linked DNA sequences are contiguous and, where necessary to join two protein-coding regions, in the same reading frame.

The terms "polynucleotide," "nucleic acid," and "nucleotide sequence," used interchangeably herein, refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. This term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. It also includes modified nucleic acids such as methylated and/or capped nucleic acids, nucleic acids containing modified bases, backbone modifications, and the like. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" "nucleic acid," and "nucleotide sequence" should be understood to include, as applicable to the embodiments being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

The term "traditional plant breeding" refers to the utilization of natural variation found within a plant population as a source for alleles and genetic variants that impart a trait of interest to a given plant. Traditional breeding methods make use of crossing procedures that rely largely upon observed phenotypic variation to infer causative allele association. That is, traditional plant breeding relies upon observations of expressed phenotype of a given plant to infer underlying genetic cause. These observations are utilized to inform the breeding procedure in order to move allelic variation into germplasm of interest. Further, traditional plant breeding has also been characterized as comprising random mutagenesis techniques, which can be used to introduce genetic variation into a given germplasm. These random mutagenesis techniques may include chemical and/or radiation-based mutagenesis procedures. Consequently, one key feature of traditional plant breeding, is that the breeder does not utilize a genetic engineering tool that directly alters/changes/edits the plant's underlying genetic architecture in a targeted manner, in order to introduce genetic diversity and bring about a phenotypic trait of interest.

A "CRISPR-associated effector" as used herein can thus be defined as any nuclease, nickase, or recombinase associated with the CRISPR (Clustered Regularly Interspaced Short Palindromic Repeats), having the capacity to introduce a single- or double-strand cleavage into a genomic target site, or having the capacity to introduce a targeted modification, including a point mutation, an insertion, or a deletion, into a genomic target site of interest. At least one CRISPR-associated effector can act on its own, or in combination with other molecules as part of a molecular complex. The CRISPR-associated effector can be present as fusion molecule, or as individual molecules associating by or being associated by at least one of a covalent or non-covalent interaction with gRNA and/or target site so that the components of the CRISPR-associated complex are brought into close physical proximity.

The term "Cas9 nuclease" and "Cas9" can be used interchangeably herein, which refer to a RNA-guided DNA endonuclease enzyme associated with the CRISPR (Clustered Regularly Interspaced Short Palindromic Repeats), including the Cas9 protein or fragments thereof (such as a protein comprising an active DNA cleavage domain of Cas9 and/or a gRNA binding domain of Cas9). Cas9 is a component of the CRISPR/Cas genome editing system, which targets and cleaves a DNA target sequence to form a DNA double strand breaks (DSB) under the guidance of a guide RNA.

The term "CRISPR RNA" or "crRNA" refers to the RNA strand responsible for hybridizing with target DNA sequences and recruiting CRISPR endonucleases and/or CRISPR-associated effectors. CrRNAs may be naturally occurring or may be synthesized according to any known method of producing RNA.

The term "tracrRNA" refers to a small trans-encoded RNA. TracrRNA is complementary to and base pairs with crRNA to form a crRNA/tracrRNA hybrid, capable of recruiting CRISPR endonucleases and/or CRISPR-associated effectors to target sequences.

The term "Guide RNA" or "gRNA" as used herein refers to an RNA sequence or combination of sequences capable of recruiting a CRISPR endonuclease and/or CRISPR-associated effectors to a target sequence. Typically, gRNA is composed of crRNA and tracrRNA molecules forming complexes through partial complement, wherein crRNA comprises a sequence that is sufficiently complementary to a target sequence for hybridization and directs the CRISPR complex (i.e. Cas9-crRNA/tracrRNA hybrid) to specifically bind to the target sequence. Also, single guide RNA (sgRNA) can be designed, which comprises the characteristics of both crRNA and tracrRNA. Therefore, as used herein, a guide RNA can be a natural or synthetic crRNA (e.g., for Cpf1), a natural or synthetic crRNA/tracrRNA hybrid (e.g., for Cas9), or a single-guide RNA (sgRNA).

The term "guide sequence" or "spacer sequence" refers to the portion of a crRNA or guide RNA (gRNA) that is responsible for hybridizing with the target DNA.

The term "protospacer" refers to the DNA sequence targeted by a guide sequence of crRNA or gRNA. In some embodiments, the protospacer sequence hybridizes with the crRNA or gRNA guide (spacer) sequence of a CRISPR complex.

The term "CRISPR landing site" as used herein, refers to a DNA sequence capable of being targeted by a CRISPR-Cas complex. In some embodiments, a CRISPR landing site comprises a proximately placed protospacer/Protopacer Adjacent Motif combination sequence that is capable of being cleaved by a CRISPR complex.

The term "CRISPR complex", "CRISPR endonuclease complex", "CRISPR Cas complex", or "CRISPR-gRNA complex" are used interchangeably herein. "CRISPR complex" refers to a Cas9 nuclease and/or a CRISPR-associated effectors complexed with a guide RNA (gRNA). The term "CRISPR complex" thus refers to a combination of CRISPR endonuclease and guide RNA capable of inducing a double stranded break at a CRISPR landing site. In some embodiments, "CRISPR complex" of the present disclosure refers to a combination of catalytically dead Cas9 protein and guide RNA capable of targeting a target sequence, but not capable of inducing a double stranded break at a CRISPR landing site because it loses a nuclease activity. In other embodiments, "CRISPR complex" of the present disclosure refers to a combination of Cas9 nickase and guide RNA capable of introducing gRNA-targeted single-strand breaks in DNA instead of the double-strand breaks created by wild-type Cas enzymes.

As used herein, the term "directing sequence-specific binding" in the context of CRISPR complexes refers to a guide RNA's ability to recruit a CRISPR endonuclease and/or a CRISPR-associated effectors to a CRISPR landing site.

As used herein the term "targeted" refers to the expectation that one item or molecule will interact with another item or molecule with a degree of specificity, so as to exclude non-targeted items or molecules. For example, a first polynucleotide that is targeted to a second polynucleotide, according to the present disclosure has been designed to hybridize with the second polynucleotide in a sequence specific manner (e.g., via Watson-Crick base pairing). In some embodiments, the selected region of hybridization is designed so as to render the hybridization unique to the one, or more targeted regions. A second polynucleotide can cease to be a target of a first targeting polynucleotide, if its targeting sequence (region of hybridization) is mutated or is otherwise removed/separated from the second polynucleotide. Furthermore, "targeted" can be interchangeably used with "site-specific" or "site-directed," which refers to an action of molecular biology which uses information on the sequence of a genomic region of interest to be modified, and which further relies on information of the mechanism of action of molecular tools, e.g., nucleases, including CRISPR nucleases and variants thereof, TALENs, ZFNs, meganucleases or recombinases, DNA-modifying enzymes, including base modifying enzymes like cytidine deaminase enzymes, histone modifying enzymes and the like, DNA-binding proteins, cr/tracr RNAs, guide RNAs and the like.

The term "seed region" refers to the critical portion of a crRNA's or guide RNA's guide sequence that is most susceptible to mismatches with their targets. In some embodiments, a single mismatch in the seed region of a crRNA/gRNA can render a CRISPR complex inactive at that binding site. In some embodiments, the seed regions for Cas9 endonucleases are located along the last ~12 nts of the 3' portion of the guide sequence, which correspond (hybridize) to the portion of the protospacer target sequence that is adjacent to the PAM. In some embodiments, the seed regions for Cpf1 endonucleases are located along the first ~5 nts of the 5' portion of the guide sequence, which correspond (hybridize) to the portion of the protospacer target sequence adjacent to the PAM.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature*

*Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Variants of protein sequences known and disclosed herein are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids and may possess sequence identities of at least 85% or at least 90% or at least 95% depending on their similarity to the reference sequence. Methods for determining sequence identity over such short windows are available at the NCBI website on the internet. These sequence identity ranges are provided for guidance only; it is entirely possible that strongly significant homologs could be obtained that fall outside of the ranges provided.

Variants of the disclosed nucleic acid sequences are typically characterized by possession of at least about 80%, at least 90%, at least 95%, at least 96%, at least 97%, at least 98% or at least 99% sequence identity counted over the full length alignment with the nucleic acid sequence using the NCBI Blast 2.0, gapped blastn set to default parameters. One of skill in the art will appreciate that these sequence identity ranges are provided for guidance only; it is possible that TSS promotor of IPT7 sequences could be obtained that fall outside of the ranges provided.

"Complementary" refers to the capacity for pairing, through base stacking and specific hydrogen bonding, between two sequences comprising naturally or non-naturally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santa Lucia, Nucl. Acids Research, 2005; 33 (19): 6258-6267.

A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a complementary nucleic acid) under the appropriate in vitro and/or in vivo conditions of temperature and solution ionic strength.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms know in the art including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, CA). Another alignment program is Sequencher (Gene Codes, Ann Arbor, Michigan), using default parameters, and MUSCLE (Multiple Sequence Comparison by Log-Expectation; a computer software licensed as public domain).

Herein, the term "hybridize" refers to pairing between complementary nucleotide bases (e.g., adenine (A) forms a base pair with thymine (T) in a DNA molecule and with uracil (U) in an RNA molecule, and guanine (G) forms a base pair with cytosine (C) in both DNA and RNA molecules) to form a double-stranded nucleic acid molecule. (See, e.g., Wahl and Berger (1987) Methods Enzymol. 152:399; Kimmel, (1987) Methods Enzymol. 152:507). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary. It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted.

The term "modified" refers to a substance or compound (e.g., a cell, a polynucleotide sequence, and/or a polypeptide sequence) that has been altered or changed as compared to the corresponding unmodified substance or compound.

"Isolated" refers to a material that is free to varying degrees from components which normally accompany it as found in its native state. An "isolated" biological component (such as a protein, nucleic acid, or cell) has been substantially separated, produced apart from, or purified away from other biological components in the cell or tissue of a plant in which the component occurs, such as other cells, chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Isolated nucleic acid molecules (such as vector comprising a TSS:IPT7 construct), or cells containing such, in some examples are at least 50% pure, such as at least 75%, at least 80%, at least 90%, at least 95%, at least 98%, or at least 100% pure.

The term "gene edited plant, part or cell" as used herein refers to a plant, part or cell that comprises one or more endogenous genes that are edited by a gene editing system. The gene editing system of the present disclosure comprises a targeting element and/or an editing element. The targeting element is capable of recognizing a target genomic sequence. The editing element is capable of modifying the target genomic sequence, e.g., by substitution or insertion of one or more nucleotides in the genomic sequence, deletion of one or more nucleotides in the genomic sequence, alteration of genomic sequences to include regulatory sequences, insertion of transgenes at a safe harbor genomic site or other specific location in the genome, or any combination thereof. The targeting element and the editing element can be on the same nucleic acid molecule or different nucleic acid molecules.

The term "plant" refers to whole plants. The term "plant part" include differentiated and undifferentiated tissues including, but not limited to: plant organs, plant tissues, roots, stems, shoots, rootstocks, scions, stipules, petals, leaves, flowers, ovules, pollens, bracts, petioles, internodes, bark, pubescence, tillers, rhizomes, fronds, blades, stamens, fruits, seeds, tumor tissue and plant cells (e.g., single cells, protoplasts, embryos, and callus tissue). Plant cells include, without limitation, cells from seeds, suspension cultures, embryos, meristematic regions, callus tissue, leaves, roots, shoots, gametophytes, sporophytes, pollen and microspores. The plant tissue may be in a plant or in a plant organ, tissue or cell culture. The term "plant" includes reference to an immature or mature whole plant, including a plant from which seed, roots, or leaves have been removed. Seed or embryo that will produce the plant is also considered to be the plant. The present disclosure also includes seeds produced by the plants provided herein, wherein the seeds can include an exogenous nucleic acid construct comprising a TSS promoter operably linked to an IPT7 coding sequence (i.e., TSS:IPT7 construct). In one embodiment, the seeds can develop into plants with increased root mass, as compared to a wild-type variety of the plant seed.

As used herein when discussing plants, the term "ovule" refers to the female gametophyte, whereas the term "pollen" means the male gametophyte.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "transformation" refers to the introduction of exogenous genetic material (e.g., TSS:IPT7 construct and vectors containing such) into cells, for example a plant cell. Exemplary mechanisms that are to transfer DNA into plant cells include (but not limited to) electroporation, microprojectile bombardment, *Agrobacterium*-mediated transformation and direct DNA uptake by protoplasts.

The terms "transgene" or "transgenic" as used herein refer to an exogenous gene or other genetic material (e.g., TSS:IPT7 construct and vectors containing such) that has been transferred into a plant or plant cell (such as the genome of such a plant or plant cell), for example by genetic engineering methods. Exemplary transgenes include cDNA (complementary DNA), genes, and promoters. In one example, describes a segment of DNA containing an IPT7 gene or coding sequence operably linked to a TSS promoter, which is introduced into the genome of a plant or plant cell. This non-native segment of DNA may retain the ability to produce RNA or protein in the transgenic plant, or it may alter the normal function of the transgenic plant's genetic code. In some examples, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

A transgenic plant, tissue or cell is produced when at least one nucleic acid sequence that is taken from the genome of one organism, or produced synthetically, and which is then introduced into a host cell or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation and thus inheritance of the respective at least one molecule introduced into the genome of a cell. The terms "transgene-free" refers to a condition that transgene is not present or found in the genome of a host cell or tissue or organism of interest.

The phrase "under conditions sufficient for" and similarly-worded phrases are used to describe any environment that permits a desired activity. In one example the desired activity is expression of an IPT7 protein from a TSS promoter in the mesophyll cells of developing leaves, for example to increase the root mass of the plant.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. The term "plant organ" refers to plant tissue or a group of tissues that constitute a morphologically and functionally distinct part of a plant. "Progeny" comprises any subsequent generation of a plant. In some example, the tissue culture includes a homogenous population of plant cells. In some example, the tissue culture includes a callus tissue. In some example, the tissue culture includes an anther culture. In some example, the tissue culture includes a hairy root cultures.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

The terms "increase" and "decrease" as used herein refer to a positive or negative change, respectively, in quantity from a control value. In some instances, the increase or decrease can be statistically significant. An increase is a positive change, such as an increase at least 5%, at least 10%, at least 20%, at least 30%, at least 40%, at least 50%, at least 100%, at least 200%, at least 300%, at least 400% or at least 500% as compared to the control value (such as a value observed in a native or wild-type plant). A decrease is a negative change, such as a decrease of at least 20%, at least 25%, at least 50%, at least 75%, at least 80%, at least 90%, at least 95%, at least 98%, at least 99%, or at least 100% decrease as compared to a control value (such as a value observed in a native or wild-type plant). In some examples the decrease is less than 100%, such as a decrease of no more than 90%, no more than 95% or no more than 99%. In some examples, the control value is a value or range of values expected for the same plant that is not transgenic, e.g., a wild-type plant (e.g., if the test plant is a transgenic tobacco plant, the control can be a native or wild-type tobacco plant of the same variety).

By "biologically active portion" is meant a portion of a full-length parent peptide or polypeptide which portion retains an activity of the parent molecule. For example, a biologically active portion of polypeptide of the disclosure will retain the ability to increase and/or enhance suberin levels in plant cells, tissues and whole plants. As used herein, the term "biologically active portion" includes deletion mutants and peptides, for example of at least about 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 contiguous amino acids, which comprise an activity of a parent molecule. Portions of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a peptide or polypeptide of the disclosure with proteinases such as endoLys-C, endoArg-C, endoGlu-C and *Staphylococcus* V8-protease. The digested fragments can be purified by, for example, high performance liquid chromatographic (HPLC) techniques. Recombinant nucleic acid techniques can also be used to produce such portions.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

As used herein, the term "regeneration" broadly refers to the development of a plant from tissue culture. Depending on the context, the terms "growing" or "regeneration" as used herein mean growing a whole, differentiated plant from a plant cell, a group of plant cells, a plant part (including seeds), or a plant piece (e.g., from a protoplast, callus, or tissue part). The cells may, or may not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

By "obtained from" is meant that a sample such as, for example, a nucleic acid extract or polypeptide extract is isolated from, or derived from, a particular source. For example, the extract may be isolated directly from plants.

By "variant" polypeptide is intended a polypeptide derived from the native protein by deletion (so-called truncation) or addition of one or more amino acids to the N-terminal and/or C-terminal end of the native protein;

deletion or addition of one or more amino acids at one or more sites in the native protein; or substitution of one or more amino acids at one or more sites in the native protein. Variant proteins encompassed by the present disclosure are biologically active, that is they continue to possess the desired biological activity of the native protein, that is, modulating or regulatory activity as described herein. Such variants may result from, for example, genetic polymorphism or from human manipulation. Biologically active variants of a native protein of the disclosure will have at least 40%, 50%, 60%, 70%, generally at least 75%, 80%, 85%, preferably about 90% to 95% or more, and more preferably about 98% or more sequence identity to the amino acid sequence for the native protein as determined by sequence alignment programs described elsewhere herein using default parameters. A biologically active variant of a protein of the disclosure may differ from that protein by as few as 1-15 amino acid residues, as few as 1-10, such as 6-10, as few as 5, as few as 4, 3, 2, or even 1 amino acid residue.

The proteins of the disclosure may be altered in various ways including amino acid substitutions, deletions, truncations, and insertions. Methods for such manipulations are generally known in the art. For example, amino acid sequence variants of the proteins can be prepared by mutations in the DNA. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be preferable.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another, Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to the nucleotide sequence of interest which is operably linked to termination signals. An exemplary promoter is the TSS promoter described herein (e.g., SEQ ID NO: 1). It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development in animal and/or plant.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, recombinant plant viruses. Non-limiting examples of plant viruses include, TMV-mediated (transient) transfection into tobacco (Tuipe, T-H et al (1993), J. Virology Meth, 42: 227-239), ssDNA genomes viruses (e.g., family Geminiviridae), reverse transcribing viruses (e.g., families Caulimoviridae, Pseudoviridae, and Metaviridae), dsNRA viruses (e.g., families Reoviridae and Partitiviridae), (−) ssRNA viruses (e.g., families Rhabdoviridae and Bunyaviridae), (+) ssRNA viruses (e.g., families Bromoviridae, Closteroviridae, Comoviridae, Luteoviridae, Potyviridae, Sequiviridae and Tombusviridae) and viroids (e.g., families Pospiviroldae and Avsunviroidae). Detailed classification information of plant viruses can be found in Fauquet et al (2008, "Geminivirus strain demarcation and nomenclature". *Archives of Virology* 153:783-821, incorporated herein by reference in its entirety), and Khan et al. (Plant viruses as molecular pathogens; Publisher Routledge, 2002, ISBN 1560228954, 9781560228950). Examples of non-viral vectors include, but are not limited to, liposomes, polyamine derivatives of DNA, and the like.

Also, "vector" is defined to include, inter alia, any plasmid, cosmid, phage or *Agrobacterium* binary vector in double or single stranded linear or circular form which may or may not be self-transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

As used herein, the terms "vector control", "control vector" and "Col-0" refer to plants carrying a GUS reporter gene under the control of a TSS promoter, in the same vector as TSS:IPT7. It can be called TSS:GUS. GUS, β-glucuronidase, has no activity in plants and will not affect cytokinin biosynthesis. This kind of control is used to rule out any unexpected effect that comes from parts of the transgene other than IPT7 protein.

As used herein, the term "offspring" refers to any plant resulting as progeny from a vegetative or sexual reproduction from one or more parent plants or descendants thereof. For instance, an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The term "plant" includes reference to whole plants, plant organs, plant tissues, and plant cells and progeny of same, but is not limited to angiosperms and gymnosperms such as *Arabidopsis*, potato, tomato, tobacco, alfalfa, lettuce, carrot, strawberry, sugar beet, cassava, sweet potato, soybean, lima bean, pea, chick pea, maize (corn), turf grass, wheat, rice, barley, sorghum, oat, oak, eucalyptus, walnut, palm and duckweed as well as fern and moss. Thus, a plant may be a monocot, a dicot, a vascular plant reproduced from spores such as fern or a non-vascular plant such as moss, liverwort, hornwort and algae. The word "plant," as used herein, also encompasses plant cells, seed, plant progeny, propagule whether generated sexually or asexually, and descendants of any of these, such as cuttings or seed. As used herein, a "plant cell" includes, but is not limited to, a protoplast, gamete producing cell, and a cell that regenerates into a whole plant. Mesophyll is a type of highly differentiated cell found in the mesophyll layer of plant leaves. These cells in the middle of the leaf contain many chloroplasts, allowing the cells to perform photosynthesis. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent.

A "selected plant species" may be, but is not limited to, a species of any one of these "plants."

In the present disclosure, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, black raspberry, blueberry, broccoli, Brussel's sprouts, cabbage, cane berry, canola, cantaloupe, carrot, cassava, cauliflower, cedar, a cereal, celery, chestnut, cherry, Chinese cabbage, citrus, Clementine, clover, coffee, corn, cotton, cowpea, cucumber, cypress, eggplant, elm, endive, eucalyptus, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, papaya, palm, parsley, parsnip, pea, peach, peanut, pear, peat, pepper, persimmon, pigeon pea, peach, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, wild strawberry, yams, yew, and zucchini.

Any commercially or scientifically valuable plant is envisaged in accordance with these embodiments of the disclosure. Exemplary plants that can be used in the disclosed methods, or generated with the disclosed methods, further include plants which belong to the super family Viridiplantae, in particular monocotyledonous and dicotyledonous plants including a fodder or forage legume, ornamental plant, food crop, tree, or shrub, such as on selected from *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia vi/losa, Pagopyrum* spp., *Feijoa sellowlana, Fragaria* spp., *Flemingia* spp, *Freycinetia banksli, Geranium thunbergii, Gingko biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macro tyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canadensis, Phormium cookianum, Photinia* spp., *Picea glauca, Pinus* spp., *Pisum*

*sativum, Podocarpus totara, Pogonarthria fleckii, Pogonehria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, switchgrass, *Miscanthus*, *Setaria*, fescue, eucalyptus, a tree, an ornamental plant, a perennial grass and a forage crop. Alternatively, algae and other non-Viridiplantae can be used. In one example, the plant is one found in a wetland.

Angiosperm is defined as vascular plants having seeds enclosed in an ovary. Angiosperms are seed plants that produce flowers that bear fruits. Angiosperms are divided into dicotyledonous and monocotyledonous plants.

Dicotyledonous plant (Dicot) is defined as a flowering plant whose embryos have two seed halves or cotyledons, branching leaf veins, and flower parts in multiples of four or five. Examples of dicots include but are not limited to, *Eucalyptus, Populus*, Liquidamber, *Acacia*, teak, mahogany, tobacco, *Arabidopsis*, tomato, potato sugar beet, broccoli, cassava, sweet potato, pepper, poinsettia, bean, rapeseed/canola, alfalfa, radish, crimson clover, field pennycress, soybean, carrot, strawberry, lettuce, oak, maple, walnut, rose, mint, squash, daisy, geranium, avocado, cotton/cottonseed and cactus.

*Thlaspi arvense*, known by the common name field pennycress (aka pennycress), is a flowering plant in the cabbage family Brassicaceae. CoverCress is a new oilseed crop grown over winter between normal full season corn and soybeans. CoverCress was developed from pennycress. Low fiber pennycress lines are provided in U.S. Pat. No. 10,709,151, which is assigned to CoverCress Inc.

Monocotyledonous Plant (Monocot) is defined as a flowering plant having embryos with one cotyledon or seed leaf, parallel leaf veins, and flower parts in multiples of three. Examples of monocots include, but are not limited to turfgrass, corn/maize, rice, oat, annual ryegrass, wheat, barley, sorghum, orchid, iris, lily, onion, and palm. Examples of turfgrass include, but are not limited to *Agrostis* spp. (bentgrass species including colonial bentgrass and creeping bentgrasses), *Poa pratensis* (Kentucky bluegrass), *Lolium* spp. (ryegrass species including annual ryegrass and perennial ryegrass), *Festuca arundinacea* (tall fescue) *Festuca rubra commutata* (Chewings fescue), *Cynodon dactylon* (bermudagrass, *Pennisetum clandestinum* (kikuyu grass), *Stenotaphrum secundatum* (St. Augustine grass), *Zoysia japonica* (zoysia grass), and *Dichondra micrantha*.

The methods for targeted gene-editing system as described herein can be used to confer desired traits on essentially any plant. A wide variety of plants and plant cell systems may be engineered for the desired physiological and agronomic characteristics described herein using the nucleic acid constructs of the present disclosure and the various transformation methods. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, grape, peach, pear, plum, raspberry, black raspberry, blackberry, cane berry, cherry, avocado, strawberry, wild strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). In some embodiments, fruit crops such as tomato, apple, peach, pear, plum, raspberry, black raspberry, blackberry, cane berry, cherry, avocado, strawberry, wild strawberry, grape and orange.

"Grain" is intended to mean the mature seed produced by commercial growers for purposes other than growing or reproducing the species.

"Biomass" is intended to mean the organic matter derived from an organism, such as a plant or part thereof, for example the roots. In some examples, above-ground biomass refers to all the above ground plant material at a particular point of time, thus including the leaves, stems and may include flowers (at varying stages of development given the flowering period ranges over a period of time). Above-ground biomass can include all vegetative and reproductive material produced by the plant at time of harvest. In some examples, root biomass refers to all the below ground plant material at a particular point of time, thus including the roots.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype. With regard to a SNP marker, allele refers to the specific nucleotide base present at that SNP locus in that individual plant.

As used herein, the term "locus" (plural: "loci") refers to any site that has been defined genetically. A locus may be a gene, or part of a gene, or a DNA sequence that has some regulatory role, and may be occupied by different sequences.

The term "amplifying" in the context of nucleic acid amplification is any process whereby additional copies of a selected nucleic acid (or a transcribed form thereof) are produced. An "amplicon" is an amplified nucleic acid, e.g., a nucleic acid that is produced by amplifying a template nucleic acid by any available amplification method.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the average person skilled in molecular-biological techniques which techniques are for instance described in Lefebvre and Chevre, 1995; Lorez and Wenzel, 2007, Srivastava and Narula, 2004, Meksem and Kahl, 2005, Phillips and Vasil, 2001. General information concerning AFLP technology can be found in Vos et al. (1995, AFLP: a new technique for DNA fingerprinting, Nucleic Acids Res. 1995 Nov. 11; 23(21): 4407-4414).

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "homologous" or "homolog" is known in the art and refers to related sequences that share a common ancestor or family member and are determined based on the degree of sequence identity. The terms "homology", "homologous", "substantially similar" and "corresponding substantially" are used interchangeably herein. Homologs usually control, mediate, or influence the same or similar biochemical pathways, yet particular homologs may give rise to differing phenotypes. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared.

The term "homolog" is sometimes used to apply to the relationship between genes separated by the event of speciation (see "ortholog") or to the relationship between genes separated by the event of genetic duplication (see "paralog").

The term "homeolog" refers to a homologous gene or chromosome, resulting from polyploidy or chromosomal duplication events. This contrasts with the more common 'homolog', which is defined immediately above.

The term "ortholog" refers to genes in different species that evolved from a common ancestral gene by speciation. Normally, orthologs retain the same function in the course of evolution. Identification of orthologs is critical for reliable prediction of gene function in newly sequenced genomes.

The term "paralog" refers to genes related by duplication within a genome. While orthologs generally retain the same function in the course of evolution, paralogs can evolve new functions, even if these are related to the original one.

"Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Michigan), AlignX, and Vector NTI (Invitrogen, Carlsbad, CA).

As used herein, the term "hybrid" refers to any individual cell, tissue or plant resulting from a cross between parents that differ in one or more genes.

As used herein, the term "cross" is synonymous with hybridize or crossbreed. The act of crossing includes the mating of genetically different individual plants, such as the mating of two parent plants.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

The term "backcross" as used herein refers to the mating of a hybrid to one of its parents. For example, hybrid progeny, for example a first generation hybrid ($F_1$), can be crossed back one or more times to one of its parents. Backcrossing can be used to introduce one or more single locus conversions (such as one or more desirable traits) from one genetic background into another.

A single locus converted (aka conversion) plant refers to plants developed by backcrossing and/or by genetic transformation, wherein essentially all of the desired morphological and physiological characteristics of a particular variety (such as increased root mass) are recovered in addition to the characteristics of the single locus transferred into the variety via the backcrossing technique and/or by genetic transformation.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor. Traditionally, a subline has been derived by inbreeding the seed from an individual plant selected at the F3 to F5 generation until the residual segregating loci are "fixed" or homozygous across most or all loci. Commercial varieties (or lines) can be produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

The term "line" is also used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (TO) plant regenerated from material of that line; (b) has a pedigree comprised of a TO plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the terms "wildtype check", "wildtype", "wild-type check", "wild-type" or "check" all refer to a first cell, tissue culture, part or organism which is essentially genetically the same as a second cell, tissue culture, part or organism, respectively, except that the corresponding second cell, tissue culture, part or organism comprises a heterologous genetic element not present in the first cell, tissue culture, part or organism. Thus, for example, a first plant would be a wildtype check relative to a second plant where the only meaningful genetic difference between the two is that the second plant comprises a heterologous gene not present in the first plant.

A "subject plant or plant cell" is one in which genetic alteration, such as transformation, has been affected as to a gene of interest, or is a plant or plant cell which is descended from a plant or cell so altered and which comprises the alteration.

A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As used herein, the terms "introgression", "introgressed" and "introgressing" refer to the process whereby genes of one species, variety or cultivar are moved into the genome of another species, variety or cultivar, by crossing those species. The crossing may be natural or artificial. The process may optionally be completed by backcrossing to the recurrent parent, in which case introgression refers to infiltration of the genes of one species into the gene pool of another through repeated backcrossing of an interspecific hybrid with one of its parents. An introgression may also be described as a heterologous genetic material stably integrated in the genome of a recipient plant.

As used herein, the term "population" means a genetically homogeneous or heterogeneous collection of plants sharing a common genetic derivation.

As used herein, the term "variety" or "cultivar" means a group of similar plants that by structural features and performance can be identified from other varieties within the same species. The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

A variety is deemed to be essentially derived from another variety ('the initial variety') when: (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and, (iii) except for the differences which result from the act of derivation, it conforms to the initial variety in the expression of the essential characteristics that result from the genotype or combination of genotypes of the initial variety. UPOV, Article 14(5)(b).

An "elite line" is an agronomically superior line that has resulted from many cycles of breeding and selection for superior agronomic performance. Numerous elite lines are available. An "elite population" is an assortment of elite individuals or lines that can be used to represent the state of the art in terms of agronomically superior genotypes of a given plant species.

"Genotype" refers to the genetic constitution of a cell or organism. "Germplasm" refers to the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

"Tolerance and "improved tolerance" are used interchangeably herein and refer to any type of increase in resistance or tolerance to, or any type of decrease in susceptibility. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance that is higher than that of a comparable susceptible plant or variety.

"Linkage" refers to a phenomenon wherein alleles on the same chromosome tend to segregate together more often than expected by chance, if their transmission was independent. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A 1/100 probability of recombination per generation is defined as a map distance of 1.0 centiMorgan (1.0 cM). The genetic elements or genes located on a single chromosome segment are physically linked. Two loci can be located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 9, 8, 7, 6, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 9%, 8%, 7%, 6%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less. When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

"Linkage disequilibrium" refers to a phenomenon wherein alleles tend to remain together in linkage groups when segregating from parents to offspring, with a greater frequency than expected from their individual frequencies.

"Linkage group" refers to traits or markers that generally co-segregate. A linkage group generally corresponds to a chromosomal region containing genetic material that encodes the traits or markers.

A "genetic map" is a description of genetic linkage relationships among loci on one or more chromosomes (or linkage groups) within a given species, generally depicted in a diagrammatic or tabular form.

A "map location" or "map position" or "relative map position" is an assigned location on a genetic map relative to linked genetic markers where a specified marker can be found within a given species. Map positions are generally provided in centimorgans. A "physical position" or "physical location" or "physical map location" is the position, typically in nucleotide bases, of a particular nucleotide, such as a SNP nucleotide, on a chromosome.

"Mapping" is the process of defining the linkage relationships of loci with genetic markers, populations segregating for the markers, and standard genetic principles of recombination frequency.

As used herein, the term "mass selection" refers to a form of selection in which individual plants are selected and the next generation propagated from the aggregate of their seeds. More details of mass selection are described herein in the specification.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "self-crossing", "self pollinated" or "self-pollination" means the pollen of one flower on one plant is applied (artificially or naturally) to the ovule (stigma) of the same or a different flower on the same plant.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T and G/C content) of primer. A pair of bi-directional primers consists of one forward and one reverse primer as commonly used in the art of DNA amplification such as in PCR amplification.

A probe comprises an identifiable, isolated nucleic acid that recognizes a target nucleic acid sequence. A probe includes a nucleic acid that is attached to an addressable location, a detectable label or other reporter molecule and that hybridizes to a target sequence. Typical labels include radioactive isotopes, enzyme substrates, co-factors, ligands, chemiluminescent or fluorescent agents, haptens, and enzymes. Methods for labelling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, NY, 1989 and Ausubel et al. *Short Protocols in Molecular Biology*, $4^{th}$ ed., John Wiley & Sons, Inc., 1999.

The terms "label" and "detectable label" refer to a molecule capable of detection. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

Methods for preparing and using nucleic acid probes and primers are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, NY, 1989; Ausubel et al. *Short Protocols in Molecular Biology*, $4^{th}$ ed., John Wiley & Sons, Inc., 1999; and Innis et al. *PCR Protocols, A Guide to Methods and Applications*, Academic Press, Inc., San Diego, CA, 1990. Amplification primer pairs can be derived from a known sequence, for example, by using computer programs intended for that purpose such as PRIMER (Version 0.5, 1991, Whitehead Institute for Biomedical Research, Cambridge, MA). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual (3rd ed., Cold Spring Harbor Laboratory Press, Plainview, New York). See also Innis et al. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The present disclosure provides an isolated nucleic acid sequence comprising a sequence selected from the group consisting of genes, homologs of the genes, orthologs of the genes, paralogs of the genes, and fragments and variations thereof. In one embodiment, the present disclosure provides an isolated polynucleotide encoding a protein produced by the nucleic acid sequence, comprising a nucleic acid sequence that shares at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to the genes.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The present disclosure also provides a chimeric gene comprising the isolated nucleic acid sequence of any one of the polynucleotides described above operably linked to suitable regulatory sequences.

The present disclosure also provides a recombinant construct comprising the chimeric gene as described above. In one embodiment, said recombinant construct is a gene silencing construct, such as used in RNAi gene silencing. In another embodiment, said recombinant construct is a gene editing construct, such as used in CRISPR-Cas gene editing system.

The expression vectors of the present disclosure may include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The present disclosure also provides a transformed host cell comprising the chimeric gene as described above. In one embodiment, said host cell is selected from the group consisting of bacteria, yeasts, filamentous fungi, algae, animals, and plants.

New breeding techniques (NBTs) refer to various new technologies developed and/or used to create new characteristics in plants through genetic variation, the aim being targeted mutagenesis, targeted introduction of new genes or gene silencing (RdDM). The following breeding techniques are within the scope of NBTs: targeted sequence changes facilitated through the use of Zinc finger nuclease (ZFN) technology (ZFN-1, ZFN-2 and ZFN-3, see U.S. Pat. No.

9,145,565, incorporated by reference in its entirety), Oligonucleotide directed mutagenesis (ODM, a.k.a., site-directed mutagenesis), Cisgenesis and intragenesis, epigenetic approaches such as RNA-dependent DNA methylation (RdDM, which does not necessarily change nucleotide sequence but can change the biological activity of the sequence), Grafting (on GM rootstock), Reverse breeding, Agro-infiltration for transient gene expression (agro-infiltration "sensu stricto", agro-inoculation, floral dip), Transcription Activator-Like Effector Nucleases (TALENs, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), engineered meganuclease, re-engineered homing endonucleases, DNA guided genome editing (Gao et al., Nature Biotechnology (2016), doi: 10.1038/nbt.3547, incorporated by reference in its entirety), and Synthetic genomics. A major part of today's targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development", which is incorporated by reference in its entirety.

As used herein, "suberin" refers to a highly hydrophobic and a somewhat 'rubbery' material. In roots, suberin is deposited in the radial and transverse cell walls of the endodermal cells.

Suberin is found in the phellem layer of the periderm (or cork). This is outermost layer of the bark. The cells in this layer are dead and abundant in suberin, preventing water loss from the tissues below. Suberin can also be found in various other plant structures. For example, they are present in the lenticels on the stems of many plants and the net structure in the rind of a netted melon is composed of suberised cells.

For a detailed report on suberin synthesis and export, see Vishwanath et al., 2015, Suberin: biosynthesis, regulation, and polymer assembly of a protective extracellular barrier, Plant Cell Rep. 34:573-586.

II. Nucleic Acid Molecules and Proteins

Isopentenyl-transferases (IPT). The enzyme isopentenyl-transferase (IPT) is responsible for the rate-limiting step of cytokinin biosynthesis, an important plant hormone with key roles in meristem maintenance and organ development (Chen et al., 2017, South African Journal of Botany 109: 96-111). Cytokinins, which are central regulators of cell division and differentiation in plants, are adenine derivatives carrying an isopentenyl side chain that may be hydroxylated. Plants have two classes of isopentenyltransferases (IPTs) acting on the adenine moiety: ATP/ADP isopentenyltransferases (in *Arabidopsis thaliana*, AtIPT1, 3, 4-8) and tRNA IPTs (in *Arabidopsis*, AtIPT2 and 9). See, e.g., Miyawaki et al., 2006, PNAS 103(46):16598-16603.

Isopentenyl-transferase 7 (IPT7). IPT7 is an enzyme involved in cytokinin biosynthesis. IPT7 catalyzes the transfer of an isopentenyl group from dimethylallyl diphosphate (DMAPP) to ATP and ADP. IPTs belong to the enzyme class EC 2.5.1.27. It is shown herein that expressing IPT7 from a TSS promoter in mesophyll cells of developing leaves of plants increases root mass of the plants.

In enzymology, an adenylate dimethylallyltransferase (EC 2.5.1.27) is an enzyme that catalyzes the chemical reaction: dimethylallyl diphosphate+AMP or ADP or ATP<=>diphosphate+N(6)-(dimethylally)adenosine 5'-phosphate. Thus, the two substrates of this enzyme are dimethylallyl diphosphate and AMP, whereas its two products are diphosphate and N6-(dimethylallyl)adenosine 5'-phosphate. This enzyme belongs to the family of transferases, specifically those transferring aryl or alkyl groups other than methyl groups. The systematic name of this enzyme class is dimethylallyl-diphosphate:AMP dimethylallyltransferase. Other names in common use include cytokinin synthase, isopentenyltransferase, 2-isopentenyl-diphosphate: AMP Delta2-isopentenyltransferase and adenylate isopentenyltransferase. See, e.g., "Cytokinin biosynthesis in a cell-free system from cytokinin-autotrophic tobacco tissue cultures". *FEBS Lett.* 107 (1):15-20. 1979. doi:10.1016/0014-5793(79)80452-4. PMID 499537.

IPT7 sequences are publicly available. For example, GenBank® Accession Nos: NM_113267.3 and OAP02016.1 disclose *Arabidopsis thaliana* nucleic acid and protein sequences, respectively (SEQ ID NOS: 2 and 4 provide an exemplary coding and protein sequence, respectively); GenBank® Accession Nos. JN128581.1 and CDM82045.1 disclose exemplary *Triticum aestivum* IPT7 nucleic acid and protein sequences, respectively; GenBank® Accession Nos: MF182112.1 and AVP26993.1 disclose exemplary IPT7 nucleic acid and protein sequences, respectively from *Oryza sativa*; and GenBank® Accession Nos: EU263130.1 and ABY78886.1 disclose exemplary IPT7 nucleic acid and protein sequences, respectively from *Zea mays*. It should be noted, however, that IPT7 from these species are not necessarily true homologs of *Arabidopsis* IPT7. The numbering system between species differ. For example, as far as is known at the present time there is no true homolog of AtIPT7 in monocots, because of the unique N-terminal mitochondria transit peptide present in AtIPT7.

However, one skilled in the art will appreciate that in some examples, an IPT7 sequence can include variant sequences (such as allelic variants, homologs, homeologs and orthologs) that retain IPT7 activity. In some examples, when an IPT7 gene is expressed in a plant from a TSS promoter, it increases root mass in the plant and/or increases the amount of carbon sequestered in the plant, such as a dicot or a monocot.

Tetratricopeptide repeat (TPR)-domain suppressor of STIMPY (TSS) promoter. As used herein, a tetratricopeptide repeat (TPR)-domain suppressor of STIMPY (TSS) promoter (TSS promoter or TSSp) refers to a promoter found in *Arabidopsis* which drives expression of the TSS gene (AT4 g28080), in the mesophyll cells of developing leaves.

An exemplary TSS promoter sequence is provided in SEQ ID NO: 1. The disclosure also provides TSS promoter sequences having at least 80%, at least 85%, at least 90%, at least 95%, at least 96%, at least 97%, at least 98%, at least 99%, or 100% sequence identity to SEQ ID NO: 1.

The disclosure encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified polynucleotide or polypeptide is substantially free of other cellular material, or culture medium when produced by recombinant techniques, or substantially free of chemical precursors or other chemicals when chemically synthesized. Suitably, an "isolated" polynucleotide is free of sequences (especially protein encoding sequences) that naturally flank the polynucleotide (i.e., sequences located at the 5' and 3' ends of the polynucleotide) in the genomic DNA of the organism from which the polynucleotide was derived. For example, in various embodiments, the isolated polynucleotide can contain less than about 5 kb, 4 kb, 3 kb, 2 kb, 1 kb, 0.5 kb, or 0.1 kb of nucleotide sequences that naturally flank the polynucleotide in genomic DNA of the cell from which the polynucleotide was derived. A polypeptide that is substantially free of cellular material includes preparations of protein having less than about 30%, 20%, 10%, 5%, (by dry weight) of contaminating protein. When the protein of the disclosure or biologically active portion thereof is recombinantly produced, culture medium suitably represents less than about 30%, 20%, 10%, or 5% (by dry weight) of chemical precursors or non-protein-of-interest chemicals.

A portion of a nucleotide sequence that encodes a biologically active portion of a polypeptide of the disclosure will encode at least about 5, 6, 7, 8, 9, 10, 11, 12, 13, 14, 15, 16, 17, 18, 19, 20, 21, 22, 23, 24, 25, 30, 40, 50, 60, 70, 80, 90, 100, 120, 150, 300, 400, 500, 600, 700, 800, 900 or 1000 contiguous amino acid residues, or almost up to the total number of amino acids present in a full-length polypeptide of the disclosure. Portions of a nucleotide sequence and/or upstream and downstream of the gene that are useful as hybridization probes or PCR primers generally need not encode a biologically active portion of a polypeptide.

Thus, a portion of a nucleotide sequence may encode a biologically active portion of a polypeptide, or it may be a fragment that can be used as a hybridization probe or PCR primer using standard methods known in the art. A biologically active portion of a polypeptide can be prepared by isolating a portion of one of the nucleotide sequences of the disclosure, expressing the encoded portion of the polypeptide (e.g., by recombinant expression in vitro), and assessing the activity of the encoded portion of the polypeptide. Nucleic acid molecules that are portions of a nucleotide sequence comprise at least about 15, 16, 17, 18, 19, 20, 25, 30, 50, 75, 100, 150, 200, 250, 300, 350, 400, 450, 500, 550, 600, 650, 700, 750, 800, 850, 900, 950, 1000, 1050, 1100, 1150, 1200, 1250, or 1300 nucleotides, or almost up to the number of nucleotides present in a full-length nucleotide sequence disclosed herein.

The disclosure also contemplates using variants of the disclosed nucleotide sequences. Nucleic acid variants can be naturally occurring, such as allelic variants (same locus), homologues (different locus), and orthologues (different organism) or can be non-naturally occurring. Naturally occurring variants such as these can be identified with the use of well-known molecular biology techniques, as, for example, with polymerase chain reaction (PCR) and hybridization techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of one of the polypeptides of the disclosure. Variant nucleotide sequences also include synthetically derived nucleotide sequences, such as those generated, for example, by using site-directed mutagenesis but which still encode a polypeptide of the disclosure. Generally, variants of a particular nucleotide sequence of the disclosure will have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

Variant nucleotide sequences also encompass sequences derived from a mutagenic or recombinant procedures such as 'DNA shuffling' which can be used for swapping domains in a polypeptide of interest with domains of other polypeptides. With DNA shuffling, one or more different coding sequences can be manipulated to create a new sequence possessing desired properties. In this procedure, libraries of recombinant polynucleotides are generated from a population of related polynucleotides comprising sequence regions that have substantial sequence identity and can be homologously recombined in vitro or in vivo. For example, using this approach, sequence motifs encoding a domain of interest may be shuffled between the gene of the disclosure and other known genes to obtain a new gene coding for a protein with an improved property of interest, such increasing suberin content of plant cells, plant tissues, plant parts and whole plants. Strategies for DNA shuffling are known in the art. See, for example: Stemmer (1994, Proc. Natl. Acad. Sci. USA 91:10747-10751; 1994, Nature 370:389-391); Crameri et al. (1997, Nature Biotech. 15:436-438); Moore et al. (1997, J. Mol. Biol. 272:336-347); Zlang et al. (1997 Proc. Natl. Acad. Sci. USA 94:450-44509); Crameri et al. (1998, Nature 391:288-291); and U.S. Pat. Nos. 5,605,793 and 5,837,458.

The present disclosure provides nucleotide sequences comprising at least a portion of the isolated proteins encoded by nucleotide sequences for a gene, homologs of the gene, orthologs of the gene, paralogs of gene, and fragments and variations thereof.

In some embodiments, the present disclosure provides a nucleotide sequence encoding the gene, and/or functional fragments and variations thereof comprising a nucleotide sequence that shares at least about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, about 99.1%, about 99.2%, about 99.3%, about 99.4%, about 99.5%, about 99.6%, about 99.7%, about 99.8%, or about 99.9% sequence identity.

In some embodiments, the present disclosure provides nucleotide sequences for the gene, homologs of the gene, orthologs of the gene, paralogs of the gene, and fragments and variations thereof comprising nucleotide sequences that share at least about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, about 99.1%, about 99.2%, about 99.3%, about 99.4%, about 99.5%, about 99.6%, about 99.7%, about 99.8%, or about 99.9% sequence identity.

In some embodiments, nucleotide sequences for the gene, homologs of the gene, orthologs of the gene, paralogs of the gene, and fragments and variations thereof can be used to be expressed in plants. In some embodiments, said nucleotide sequences can be used to be incorporated into an expression cassette, which is capable of directing expression of a nucleotide sequence for the gene, homologs of the gene, orthologs of the gene, paralogs of the gene, and fragments and variations thereof in a plant cell, plant tissue, plant part or whole plant. This expression cassette comprises a promoter operably linked to the nucleotide sequence of interest which is operably linked to termination signals. It also typically comprises sequences required for proper translation of the nucleotide sequence. The coding region usually codes for a protein of interest. In some embodiments, the expression cassette comprising the nucleotide sequence for the gene, homologs of the gene, orthologs of the gene, paralogs of the gene, and fragments and variations thereof is chimeric so that at least one of its components is heterologous with respect to at least one of its other components.

In other embodiments, the expression cassette is one which is naturally occurring but has been obtained in a recombinant form useful for heterologous expression. The expression of the nucleotide sequence in the expression cassette can be under the control of a constitutive promoter or of an inducible promoter which initiates transcription only when the host cell is exposed to some particular external stimulus. Also, the expression of the nucleotide sequence in the expression cassette can be under the control of a tissue-specific promoter, such as specific root tissues, including, but not limited to, the phellogen, pericycle or procambium. In the case of a multicellular organism, the promoter can also be specific to a particular tissue or organ or stage of development in animal and/or plant.

The present disclosure provides polypeptides and amino acid sequences comprising at least a portion of the proteins encoded by nucleotide sequences for the gene, homologs of the gene, orthologs of the gene, homeologs of the gene, paralogs of the gene, and fragments and variations thereof.

The present disclosure also provides an amino acid sequence encoded by the nucleic acid sequences of the gene, homologs of the gene, orthologs of the gene, paralogs of the gene, and/or fragments and variations thereof. In some embodiments, the present disclosure provides an isolated polypeptide comprising an amino acid sequence that shares at least about 70%, about 75%, about 80%, about 85%, at least about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of the gene, homologs of the gene, orthologs of the gene, paralogs of the gene, and/or fragments and variations thereof. In one embodiment, the present disclosure provides an isolated polypeptide comprising an amino acid sequence which encodes an amino acid sequence that shares at least about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to an amino acid sequence encoded by the nucleic acid sequences of the gene, homologs of the gene, orthologs of the gene, paralogs of the gene, and/or fragments and variations thereof.

The disclosure also encompasses variants and fragments of proteins of an amino acid sequence encoded by the nucleic acid sequences of the gene, homologs of the gene, orthologs of the gene and/or paralogs of the gene. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both.

Functional fragments and variants of a polypeptide include those fragments and variants that maintain one or more functions of the parent polypeptide. It is recognized that the gene or cDNA encoding a polypeptide can be considerably mutated without materially altering one or more of the polypeptide's functions. First, the genetic code is well-known to be degenerate, and thus different codons encode the same amino acids. Second, even where an amino acid substitution is introduced, the mutation can be conservative and have no material impact on the essential function (s) of a protein. See, e.g., Stryer Biochemistry 3rd Ed., 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. J. Immunol. 159(5): 2502-12, 1997). Other modifications that can be made without materially impairing one or more functions of a polypeptide can include, for example, in vivo or in vitro chemical and biochemical modifications or the incorporation of unusual amino acids. Such modifications include, but are not limited to, for example, acetylation, carboxylation, phosphorylation, glycosylation, ubiquination, labelling, e.g., with radionucleotides, and various enzymatic modifications, as will be readily appreciated by those well skilled in the art. A variety of methods for labelling polypeptides, and labels useful for such purposes, are well known in the art, and include radioactive isotopes such as 32P, ligands which bind to or are bound by labelled specific binding partners (e.g., antibodies), fluorophores, chemiluminescent agents, enzymes, and anti-ligands. Functional fragments and variants can be of varying length. For example, some fragments have at least 10, 25, 50, 75, 100, 200, or even more amino acid residues. These mutations can be natural or purposely changed. In some embodiments, mutations containing alterations that produce silent substitutions, additions, or deletions, but do not alter the properties or activities of the proteins or how the proteins are made are an embodiment of the disclosure.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (J. Bacteriol., 169:751 757, 1987), O'Regan et al. (Gene, 77:237 251, 1989), Sahin Toth et al. (Protein Sci., 3:240 247, 1994), Hochuli et al. (Bio/Technology, 6:1321 1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows exemplary conservative amino acid substitutions.

TABLE 1

Exemplary conservative amino acid substitutions listed

| Original Residue | Very Highly - Conserved Substitutions | Highly Conserved Substitutions (from the Blosum90 Matrix) | Conserved Substitutions (from the Blosum65 Matrix) |
| --- | --- | --- | --- |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some examples, variants can have no more than 3, 5, 10, 15, 20, 25, 30, 40, 50, or 100 conservative amino acid changes (such as very highly conserved or highly conserved amino acid substitutions). In other examples, one or several hydrophobic residues (such as Leu, Ile, Val, Met, Phe, or Trp) in a variant sequence can be replaced with a different hydrophobic residue (such as Leu, Ile, Val, Met, Phe, or Trp) to create a variant functionally similar to the disclosed an amino acid sequences encoded by the nucleic acid sequences of the gene, homologs of the gene, orthologs of the gene and/or paralogs of the gene, and/or fragments and variations thereof.

In some embodiments, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed an amino acid sequences encoded by the nucleic acid sequences of the gene, homologs of the gene, orthologs of the gene and/or paralogs of the gene, and/or fragments and variations thereof.

In some embodiments, functional fragments derived from the orthologs of the present disclosure are provided. The functional fragments can still confer the ability to increase suberin content in plant cells, plant tissues, plant parts and whole plants when expressed in a plant. In some embodiments, the functional fragments contain at least the conserved region or Bowman-Birk inhibitor domain of a wild-type orthologs, or functional variants thereof. In some embodiments, the functional fragments contain one or more conserved region shared by two or more orthologs, shared by two or more orthologs in the same plant genus, shared by two or more dicot orthologs, and/or shared by two or more monocot orthologs. The conserved regions or Bowman-Birk inhibitor domains can be determined by any suitable computer program, such as NCBI protein BLAST program and NCBI Alignment program, or equivalent programs. In some embodiments, the functional fragments are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids shorter compared to the orthologs of the present disclosure. In some embodiments, the functional fragments are made by deleting one or more amino acid of the orthologs of the present disclosure. In some embodiments, the functional fragments share at least 80%, 85%, 90%, 95%, 96%, 97%, 98%, 99%, or more identity to the orthologs of the present disclosure.

In some embodiments, functional chimeric or synthetic polypeptides derived from the orthologs of the present disclosure are provided. The functional chimeric or synthetic polypeptides can still confer the ability to increase suberin content when expressed in a plant. In some embodiments, the functional chimeric or synthetic polypeptides contain at least the conserved region or Bowman-Birk inhibitor domain of wild-type orthologs, or functional variants thereof. In some embodiments, the functional chimeric or synthetic polypeptides contain one or more conserved region shared by two or more orthologs, shared by two or more orthologs in the same plant genus, shared by two or more monocot orthologs, and/or shared by two or more dicot orthologs. The conserved regions or Bowman-Birk inhibitor domains can be determined by any suitable computer program, such as NCBI protein BLAST program and NCBI Alignment program, or equivalent programs. In some embodiments, the functional chimeric or synthetic polypeptides share at least 80%, 85%, 90%, 95%, 96%, 97%, 98%, 99%, or more identity to the orthologs of the present disclosure.

Sequences of conserved regions unique to target alleles can also be used to knock-down the level of one or more orthologs. In some embodiments, sequences of conserved regions can be used to make gene silencing molecules to target one or more orthologs. In some embodiments, the gene silencing molecules are selected from the group consisting of double-stranded polynucleotides, single-stranded polynucleotides or Mixed Duplex Oligonucleotides. In some embodiments, the gene silencing molecules comprises a DNA/RNA fragment of about 10 bp, 15 bp, 19 bp, 20 bp, 21 bp, 25 bp, 30 bp, 40 bp, 50 bp, 60 bp, 70 bp, 80 bp, 90 bp, 100 bp, 150 bp, 200 bp, 250 bp, 300 bp, 350 bp, 400 bp, 500 bp, 600 bp, 700 bp, 800 bp, 900 bp, 1000 bp, or more polynucleotides, wherein the DNA/RNA fragment share at least 90%, 95%, 99%, or more identity to a conserved region of the orthologs sequences of the present disclosure, or complementary sequences thereof.

III. Plant Transformation

The disclosure thus provides transgenic plants, plant parts, and plant cells expressing an IPT protein (e.g., IPT7) having at least 80%, at least 85%, at least 90%, at least 95%, at least 96%, at least 97%, at least 98%, at least 99%, or 100% sequence identity to SEQ ID NO: 4, Accession No. CDM82045.1 or ABY78886.1, from a TSS promoter. The disclosure also provides an IPT encoding nucleic acid molecules (e.g., for IPT7) having at least 80%, at least 85%, at least 90%, at least 95%, at least 96%, at least 97%, at least 98%, at least 99%, or 100% sequence identity to SEQ ID NO: 2, JN128581.1 or EU263130.1.

Provided herein are isolated transgenic nucleic acid molecules. Such molecules are not found in nature. The disclosed transgenic nucleic acid molecules include (1) a TPR-domain suppressor of STIMPY (TSS) promoter operably linked to (2) an isopentenyl-transferase 7 (IPT7) coding sequence. In some examples, the transgenic nucleic acid molecules are part of a vector, such as a plasmid or viral vector. In some examples, the vector is one not naturally found in plants. In some examples, such a vector has at least 80%, at least 90%, at least 95%, at least 96%, at least 97%, at least 98%, at least 99%, or 100% sequence identity SEQ ID NO: 3.

In some examples, the TSS promoter has at least 80%, at least 90%, at least 95%, at least 96%, at least 97%, at least 98%, at least 99%, or 100% sequence identity SEQ ID NO: 1. In some examples, the IPT7 coding sequence has at least 80%, at least 90%, at least 95%, at least 96%, at least 97%, at least 98%, at least 99%, or 100% sequence identity SEQ ID NO: 2 or at least 80%, at least 90%, at least 95%, at least 96%, at least 97%, at least 98%, at least 99%, or 100% sequence identity nucleotides 90 to 1079 of SEQ ID NO: 2. In some examples, the IPT7 coding sequence has at least 80%, at least 90%, at least 95%, at least 96%, at least 97%, at least 98%, at least 99%, or 100% sequence identity to the nucleic acid sequence of GenBank® Accession No. JN128581.1 or EU263130.1. In some examples, the IPT7 coding sequence encodes a protein having at least 80%, at least 90%, at least 95%, at least 96%, at least 97%, at least 98%, at least 99%, or 100% sequence identity to SEQ ID NO: 4. In some examples, the IPT7 coding sequence encodes a protein having at least 80%, at least 90%, at least 95%, at least 96%, at least 97%, at least 98%, at least 99%, or 100% sequence identity to the nucleic acid sequence of GenBank® Accession No. CDM82045.1 or ABY78886.1.

In some examples, the IPT7 coding sequence or protein sequence encoded thereby is endogenous to a cell into which the transgenic nucleic acid molecule is introduced. For example, the IPT7 coding sequence or protein sequence encoded thereby can be a tobacco IPT7 sequence, and the cell into which the transgenic nucleic acid molecule is introduced a tobacco plant cell. In some examples, the IPT7 coding sequence or protein sequence encoded thereby is exogenous to a cell into which the transgenic nucleic acid molecule is introduced. For example, the IPT7 coding sequence or protein sequence encoded thereby can be an *Arabidopsis* IPT7 sequence, and the cell into which the transgenic nucleic acid molecule is introduced a *Brassica napus* plant cell.

Also provided are isolated transgenic plant cells that include a disclosed transgenic nucleic acid molecule having a TSS promoter operably linked to an IPT7 coding sequence, as well as isolated transgenic plant cells that include a vector containing any such disclosed transgenic nucleic acid molecule.

Also provided are transgenic plants that include one or more disclosed transgenic nucleic acid molecules having a TSS promoter operably linked to an IPT7 coding sequence, as well as transgenic plants that include a vector or plant cell containing any such disclosed transgenic nucleic acid molecule. In some examples, the transgenic plant is a dicot.

Also provided are transgenic plant parts that include one or more disclosed transgenic nucleic acid molecules having a TSS promoter operably linked to an IPT7 coding sequence, as well as transgenic plant parts that include a vector or plant cell containing any such disclosed transgenic nucleic acid molecule. In some examples, the transgenic plant part is a protoplast, leaf, stem, root, root tips, anther, pistil, stamen, seed, embryo, pollen, ovule, microspore, protoplast, sporophyte, gametophyte, cotyledon, hypocotyl, flower, shoot, tissue, petiole, or meristematic cell.

In some examples, the transgenic plant, isolated transgenic plant cell, or transgenic plant part is or is from a dicot, such as a *Brassica* spp. (e.g., canola), tobacco, legume (e.g., pea, bean, lentil, or peanut), daisy, mint, lettuce, tomato, oak tree, maple tree, elm tree, spruce tree, apple tree, orange tree, rose bush, sunflower, or squash.

The disclosed transgenic plants, transgenic plant cells, and transgenic plant parts can further include one or more additional exogenous nucleic acid(s) encoding a protein(s) that confers upon the transgenic plant, transgenic plant part, or transgenic plant cell a desired trait, such as one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism. The disclosed transgenic plants, transgenic plant cells, and transgenic plant parts can further include a single locus conversion, such as a transgene, for example a single locus that confers a desired trait. Examples of such traits include male sterility, herbicide tolerance, insect resistance, pest resistance, disease resistance, modified fatty acid metabolism, abiotic stress resistance, altered seed amino acid composition, site-specific genetic recombination, and modified carbohydrate metabolism.

The disclosed transgenic plants that include one or more disclosed transgenic nucleic acid molecules having a TSS promoter operably linked to an IPT7 coding sequence, in some examples express at least about 10%, at least 20%, at least 25%, at least 30%, at least 40%, at least 50%, at least 60%, at least 70%, at least 80%, at least 90%, at least 100%, at least 200%, at least 300%, at least 400% or at least 500% greater levels (such as at least 10-fold, at least 25-fold, at least 100-fold, at least 250-fold, at least 750-fold, or at least 1000-fold more) of IPT7 in mesophyll cells during development as compared to a wild-type plant of the same species. In some examples, the disclosed transgenic plants that include one or more disclosed transgenic nucleic acid molecules having a TSS promoter operably linked to an IPT7 coding sequence have (1) at least about 5%, at least 6%, at least 7%, at least 8%, at least 9%, at least 10%, at least 11%, at least 12%, at least 13%, at least 14%, at least 15%, at least 16%, at least 17%, at least 18%, at least 19% or at least 20% more cells in the root meristematic zone at seedling stage as compared to a wild-type plant of the same species, (2) at least about 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29% or at least 30% greater root biomass as compared to a wild-type plant of the same species, (3) no significant decrease in above ground growth as compared to a wild-type plant of the same species (such as a difference of no more than 10%, no more than 5%, no more than 4%, no more than 3%, no more than 2%, or no more than 1%, such as 0.1 to 10%, 0.5 to 10%, 1 to 10%, 1 to 8%, 1 to 6%, 0.1 to 5%, 0.5 to 5%, or 1 to 5%) (4) ability to sequester at least about 20%, at least 40%, at least 50%, at least 60%, at least 70%, at least 80%, at least 90%, at least 95%, at least 100%, at least 200%, at least 300%, at least 400% or at least 500% more carbon in the roots as compared to a wild-type plant of the same species, or (5) combinations thereof. Exemplary methods of measuring an amount or number of roots, root biomass, cells in the root meristematic zone, and above ground growth are provided herein. In some examples, above ground growth is determined by measuring one or more of days to flowering, rosette dry weight, and shoot dry weight.

Also provided are methods for increasing root mass in a plant, such as an increase of at least about 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29% or at least 30% as compared to a wild-type plant of the same species. Such methods can include introducing one or more disclosed transgenic nucleic acid molecules having a TSS promoter operably linked to an IPT7 coding sequence (or a vector including such a nucleic acid molecule) into a plant cell, allowing the plant cell to develop into a plant (for example by cultivating the plant cell to form a plant cell culture and regenerating the plant cell culture to form a plant), and expressing IPT7 from the TSS promoter in mesophyll cells in developing leaves (e.g., pre-senescence leaves) of the plant, thereby increasing root mass in the plant. Thus, in some examples, such a plant is transgenic. In some examples, the method further includes measuring root mass in the resulting plant and in some examples comparing the measured root mass of the resulting plant to a root mass observed with a wild type plant of the same species.

Also provided are methods for decreasing the shoot-to-root dry weight ratio in a plant, such as a decrease of at least about 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29% or at least 30% as compared to a wild-type plant of the same species. The decreased shoot-to-root dry weight ratio can be achieved without reducing or without reducing significantly the shoot dry weight of the comparable wildtype plant. In other words, the decrease in the shoot-to-root dry weight ratio achieved by the methods of the present disclosure is due to an increased root dry weight relative to shoot dry weight of the improved plant when compared to the appropriate wildtype check. Such methods can include introducing one or more disclosed transgenic nucleic acid molecules having a TSS promoter operably linked to an IPT7 coding sequence (or a vector including such a nucleic acid molecule) into a plant cell, allowing the plant cell to develop into a plant (for example by cultivating the plant cell to form a plant cell culture and regenerating the plant cell culture to form a plant), and expressing IPT7 from the TSS promoter in mesophyll cells in developing leaves (e.g., pre-senescence leaves) of the plant, thereby decreasing the shoot-to-root dry weight ratio in the plant. Thus, in some examples, such a plant is transgenic. In some examples, the method further includes measuring the shoot-to-root dry weight ratio in the resulting plant and in some examples comparing the measured shoot-to-root dry weight ratio of the resulting plant to a shoot-to-root dry weight ratio observed with an appropriate wild type (i.e., check) plant of the same species.

Also provided are methods for increasing the number of cells in the root meristematic zone at seedling stage in a plant, such as an increase of at least about 5%, at least 6%, at least 7%, at least 8%, at least 9%, at least 10%, at least 11%, at least 12%, at least 13%, at least 14%, at least 15%, at least 16%, at least 17%, at least 18%, at least 19% or at least 20% as compared to a wild-type plant of the same species. Such methods can include introducing one or more disclosed transgenic nucleic acid molecules having a TSS promoter operably linked to an IPT7 coding sequence (or a vector including such a nucleic acid molecule) into a plant cell, allowing the plant cell to develop into a plant (for example by cultivating the plant cell to form a plant cell culture and regenerating the plant cell culture to form a plant), and expressing IPT7 from the TSS promoter in mesophyll cells in developing leaves (e.g., pre-senescence leaves) of the plant, thereby increasing the cells in the root meristematic zone at seedling stage in the plant. Thus, in some examples, such a plant is transgenic. In some examples, the method further includes measuring the number of cells in the root meristematic zone at seedling stage in the resulting plant and in some examples comparing the number of cells in the root meristematic zone at seedling stage of the resulting plant to a number of roots observed with a wild type plant of the same species.

Also provided are methods for increasing carbon sequestration in the roots of a plant, such as an increase of at least about 20%, at least 40%, at least 50%, at least 60%, at least 70%, at least 80%, at least 90%, at least 95%, at least 100%, at least 200%, at least 300%, at least 400% or at least 500% as compared to an amount observed in a wild-type plant of the same species. Such methods can include introducing one or more disclosed transgenic nucleic acid molecules having a TSS promoter operably linked to an IPT7 coding sequence (or a vector including such a nucleic acid molecule) into a plant cell, allowing the plant cell to develop into a plant (for example by cultivating the plant cell to form a plant cell culture and regenerating the plant cell culture to form a plant), and expressing IPT7 from the TSS promoter in mesophyll cells in developing leaves (e.g., pre-senescence leaves) of the plant, thereby root carbon sequestration by the plant. Thus, in some examples, such a plant is transgenic. In some examples, the method further includes measuring an amount of carbon sequestration by the resulting plant and in some examples comparing the amount of carbon sequestration by the resulting plant to an amount of carbon sequestration by a wild type plant of the same species.

Polynucleotides coding for a gene, homologs of a gene, orthologs of a gene and/or paralogs of a gene, and/or fragments and variations thereof of the present disclosure can be transformed into plant cells, plant tissues, plant parts and whole plants.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and Agrobacterium-mediated transformation. See, for example, U.S. Pat. Nos. 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

Agrobacterium tumefaciens is a naturally occurring bacterium that is capable of inserting its DNA (genetic information) into plants, resulting in a type of injury to the plant known as crown gall. Most species of plants can now be transformed using this method, including cucurbitaceous species.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

The most common method for the introduction of new genetic material into a plant genome involves the use of living cells of the bacterial pathogen Agrobacterium tumefaciens to literally inject a piece of DNA, called transfer or T-DNA, into individual plant cells (usually following wounding of the tissue) where it is targeted to the plant nucleus for chromosomal integration. There are numerous patents governing Agrobacterium mediated transformation and particular DNA delivery plasmids designed specifically for use with Agrobacterium—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. Agrobacterium-mediated plant transformation involves as a first step the placement of DNA fragments cloned on plasmids into living Agrobacterium cells, which are then subsequently used for transformation into individual plant cells. Agrobacterium-mediated plant transformation is thus an indirect plant transformation method. Methods of Agrobacterium-mediated plant transformation that involve using vectors with no T-DNA are also well known to those skilled in the art and can have applicability in the present disclosure. See, for example, U.S. Pat. No. 7,250,554, which utilizes P-DNA instead of T-DNA in the transformation vector.

A transgenic plant formed using Agrobacterium transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767, 378; 5,994,629). More typically, however, negative selection is used because it is more efficient, utilizing selective agents such as herbicides or antibiotics that either kill or inhibit the growth of non-transformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., Nucl Acids Res 18: 1062 (1990), Spencer et al., Theor Appl Genet 79: 625-631(1990), U.S. Pat. Nos. 4,795,855, 5,378, 824 and 6,107,549). In addition, the dhfr gene, which confers resistance to the anticancer agent methotrexate, has been used for selection (Bourouis et al., EMBO J. 2(7): 1099-1104 (1983).

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present disclosure. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example) Enhancer sequences derived from the CaMV can also be utilized (U.S. Pat. Nos. 5,164,316; 5,196,525; 5,322, 938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a pre-existing vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include but are not limited to the *Agrobacterium* octopine synthase signal (Gielen et al., EMBO J 3:835-846 (1984)) or the nopaline synthase signal (Depicker et al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host; preferably a broad host range for prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as improved fatty acid composition, and to introduce these genes into already useful varieties of plants. Once the foreign genes have been introduced into a plant, that plant can then be used in imp plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513; 5,501,967 and 5,527,695.

The phrase "embryogenic callus cell" used herein refers to an embryogenic cell contained in a cell mass produced in vitro.

Several approaches can be utilized to transform and co-express these polynucleotides in plant cells.

Although less preferred, each of the above described polynucleotide sequences can be separately introduced into a plant cell by using three separate nucleic-acid constructs. In some embodiments, the three polynucleotide sequences can be co-introduced and co-expressed in the plant cell using a single nucleic acid construct. Such a construct can be designed with a single promoter sequences co-which can transcribe a polycistronic message including all three polynucleotide sequences. To enable co-translation of the three polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the three polypeptides described above will be translated from both the capped 5' end and the two internal IRES sequences of the polycistronic RNA molecule to thereby produce in the cell all three polypeptides.

Alternatively, the polynucleotide segments encoding the plurality of polypeptides capable of conferring increased suberin content in plant cells, plant tissues, plant parts and whole plants can be translationally fused via a protease recognition site cleavable by a protease expressed by the cell to be transformed with the nucleic acid construct. In this case, a chimeric polypeptide translated will be cleaved by a cell-expressed protease to thereby generate the plurality of polypeptides.

In other embodiments, the present disclosure utilizes a nucleic acid construct which includes three promoter sequences each capable of directing transcription of a specific polynucleotide sequence of the polynucleotide sequences described above.

Suitable promoters which can be used with the nucleic acid of the present disclosure include constitutive, inducible, or tissue-specific promoters.

Suitable constitutive promoters include, for example, CaMV 35S promoter (Odell et al., Nature 313:810-812, 1985); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); and Synthetic Super MAS (Ni et al., The Plant Journal 7: 661-76, 1995). Other constitutive promoters include those in U.S. Pat. Nos. 5,659,026, 5,608,149; 5,608, 144; 5,604,121; 5,569,597: 5,466,785; 5,399,680; 5,268, 463; and 5,608,142.

Suitable inducible promoters can be pathogen-inducible promoters such as, for example, the alfalfa PR10 promoter (Coutos-Thevenot et al., Journal of Experimental Botany 52: 901-910, 2001 and the promoters described by Marineau et al., Plant Mol. Biol. 9:335-342, 1987; Matton et al. Molecular Plant-Microbe Interactions 2:325-331, 1989; Somsisch et al., Proc. Natl. Acad. Sci. USA 83:2427-2430, 1986: Somsisch et al., Mol. Gen. Genet. 2:93-98, 1988; and Yang, Proc. Natl. Acad. Sci. USA 93:14972-14977, 1996.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

The nucleic acid construct of the present disclosure may also include at least one selectable marker such as, for example, nptII. Preferably, the nucleic acid construct is a shuttle vector, which can propagate both in *E. coli* (wherein the construct comprises an appropriate selectable marker and origin of replication) and be compatible for propagation in cells. The construct according to the present disclosure can be, for example, a plasmid, a bacmid, a phagemid, a cosmid, a phage, a virus or an artificial chromosome, preferably a plasmid.

The nucleic acid construct of the present disclosure can be utilized to stably transform plant cells. The principle methods of causing stable integration of exogenous DNA into plant genome include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/ Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/ Technology (1988) 6:559-563; McCabe et al. Bio/ Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. Suitable *Agrobacterium*-mediated procedures for introducing exogenous DNA to plant cells is described by Dougale et al. (Journal of General Virology, 79:2301-2311, 1998) and in U.S. Pat. No. 6,395,962.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Alternatively, the nucleic acid construct of the present disclosure can be introduced into plant cells by a microprojectiles bombardment. In this technique, tungsten or gold particles coated with exogenous DNA are accelerated toward the target cells. Suitable plant transformation procedures by microprojectiles bombardment are described by Sagi et al. (Biotechnology 13:481-485, 1995) and by Dougale et al. (Journal of General Virology, 79:2301-2311, 1998). Preferably, the nucleic acid construct of the present disclosure is introduced into plant cells by a microprojectiles bombardment procedure as described in Example 4 herein below.

Following transformation, the transformed cells are micropropagated to provide a rapid, consistent reproduction of the transformed material.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Stable integration of exogenous DNA sequence in the genome of the transformed plants can be determined using standard molecular biology techniques well known in the art such as PCR and Southern blot hybridization.

Although stable transformation is presently preferred, transient transformation of cultured cells, leaf cells, meristematic cells or the whole plant is also envisaged by the present disclosure.

Transient transformation can be effected by any of the direct DNA transfer methods described above or by viral infection using modified plant viruses.

Viral infection is preferred since is enables circumventing micropropagation and regeneration of a whole plant from cultured cells. Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman et al. (Communications in Molecular Biology: Viral Vectors, Cold Spring Harbor Laboratory, New York, pp. 172-189, 1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson et al. (Virology 172:285-292, 1989; Takamatsu et al. EMBO J. 6:307-311, 1987; French et al. (Science 231:1294-1297, 1986); and Takamatsu et al. (FEBS Letters 269:73-76, 1990).

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA.

If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present disclosure is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters.

Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of the present disclosure can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

IV. Breeding Methods

Also provided are methods for breeding a plant with increased root mass, such as an increase of at least about 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29% or at least 30% as compared to a wild-type plant of the same species. Such methods can include crossing a disclosed transgenic plant expressing IPT7 from the TSS promoter in mesophyll cells in developing leaves with a second plant, obtaining seed from the crossing, planting the seeds and growing the seeds to plants, and selecting from said plants those with increased root mass. In some examples, such a methods includes crossing a disclosed transgenic plant expressing IPT7 from the TSS promoter in mesophyll cells in developing leaves with a second plant, thereby generating plants with increased root mass.

Also provided are methods for breeding a plant with more cells in the root meristematic zone at seedling stage in a plant, such as an increase of at least about 5%, at least 6%, at least 7%, at least 8%, at least 9%, at least 10%, at least 11%, at least 12%, at least 13%, at least 14%, at least 15%, at least 16%, at least 17%, at least 18%, at least 19% or at least 20% as compared to a wild-type plant of the same species. Such methods can include crossing a disclosed transgenic plant expressing IPT7 from the TSS promoter in mesophyll cells in developing leaves with a second plant, obtaining seed from the crossing, planting the seeds and growing the seeds to plants, and selecting from said plants those with more cells in the root meristematic zone at seedling stage. In some examples, such a methods includes crossing a disclosed transgenic plant expressing IPT7 from the TSS promoter in mesophyll cells in developing leaves with a second plant, thereby generating plants with more cells in the root meristematic zone at seedling stage.

Also provided are methods for breeding a plant with increased root carbon sequestration ability, such as an increase of at least about 20%, at least 40%, at least 50%, at least 60%, at least 70%, at least 80%, at least 90%, at least 95%, at least 100%, at least 200%, at least 300%, at least 400% or at least 500% as compared to a wild-type plant of the same species. Such methods can include crossing a disclosed transgenic plant expressing IPT7 from the TSS promoter in mesophyll cells in developing leaves with a second plant, obtaining seed from the crossing, planting the seeds and growing the seeds to plants, and selecting from said plants those with a greater ability to sequester carbon. In some examples, such a methods includes crossing a disclosed transgenic plant expressing IPT7 from the TSS promoter in mesophyll cells in developing leaves with a second plant, thereby generating plants with a greater ability to sequester carbon.

Methods of producing a commodity plant product are provided. Such methods can include collecting or producing the commodity plant product from a transgenic plant, transgenic plant part, or transgenic plant cell provided herein (e.g., one that includes at least one nucleic acid molecule comprising a TSS promoter operably linked to an IPT coding sequence, such as an IPT7 coding sequence). For example, such a method can include growing the transgenic plant, removing the harvestable parts (such as leaves, seeds, or oils) from the transgenic plant, and producing the product from or by the harvestable parts of the plant. Also provided are commodity plant product produced by such methods, wherein the commodity plant product includes at least one nucleic acid molecule comprising a TSS promoter operably linked to an IPT7 coding sequence, or at least one non-native (e.g., exogenous) IPT7 protein. Exemplary commodity products include a protein concentrate, protein isolate, leaves, extract, or oil.

Methods of producing plant seeds are provided herein. Such methods can include crossing a transgenic plant provided herein (e.g., one that expresses IPT7 from a TSS promoter with itself or a second plant. In some examples, the second plant is gene-edited or transgenic. Also provided are $F_1$ seed produced by such a method, and a plant or part thereof produced by growing the seed. Such methods can further include (a) crossing a plant grown from said seed with itself or a different plant to produce a seed of a progeny plant of a subsequent generation; (b) growing a progeny plant of a subsequent generation from said seed of a progeny plant of a subsequent generation and crossing the progeny plant of a subsequent generation with itself or a second plant to produce a progeny plant of a further subsequent generation; and (c) repeating steps (a) and (b) using said progeny plant of a further subsequent generation from step (b) in place of the plant grown from said seed in step (a), wherein steps (a) and (b) are repeated with sufficient inbreeding to produce an inbred plant derived from the plant.

Also provided are containers (such as a paper, plastic or glass container, such as a bag, envelope, clamshell container, vial, or box), which include dried, frozen, or fresh leaves of a transgenic plant provided herein (e.g., one that includes at least one nucleic acid molecule comprising a TSS promoter operably linked to an IPT7 coding sequence); or an oil or oil extract of a transgenic plant provided herein. In some examples, the leaves of a gene-edited plant provided herein are provided alone, or in a mixture with other leaves, such as other tobacco leaves.

V. Breeding New Varieties with Increased Root Mass

Methods for crossing one or more of the disclosed transgenic plants, such as a plant (e.g., Brassica plant) expressing IPT7 from a TSS promoter, with itself or a second plant are provided, as are the seeds and plants produced by such methods. Such methods can be used for propagation of a new plant variety or can be used to produce hybrid seeds and the plants grown therefrom. Hybrid plants can be used, for example, in the commercial production of commodity products (including leaves, biomass and extracts) or in breeding programs for the production of novel varieties. A hybrid plant can also be used as a recurrent parent at any given stage in a backcrossing protocol during the production of a single locus conversion (for example introduction of one or more desirable traits) of a transgenic plant provided herein.

Methods of producing plants and/or seed are provided. Such methods can include crossing one or more of the disclosed transgenic plants, such as a plant (e.g., Brassica plant) expressing IPT7 from a TSS promoter, with itself or a second plant and harvesting a resulting seed, such as an $F_1$ hybrid seed. The resulting plant can be grown, resulting in a plant or part thereof (such as an F1 plant).

In one example methods of producing an inbred plant derived from a transgenic plant provided herein, such as a plant (e.g., Brassica plant) expressing IPT7 from a TSS promoter, are provided. In one example such methods include (a) generating a progeny plant derived from transgenic plant provided herein, such as a plant (e.g., Brassica plant) expressing IPT7 from a TSS promoter, by crossing such a transgenic plant with a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred plant derived from a transgenic plant provided herein.

The second plant crossed with a transgenic plant provided herein, such as a plant (e.g., Brassica plant) expressing IPT7 from a TSS promoter, for the purpose of developing novel varieties, is typically a plant which either itself exhibits one or more desirable characteristics or which exhibits one or more desired characteristic(s) when in hybrid combination. In one example, the second plant is gene-edited, such as transgenic. Exemplary desired characteristics include, but are not limited to: increased seed yield, increased seedling vigor, modified maturity date, desired plant height, high anthocyanin content, high phenolic content, herbicide tolerance or resistance, drought tolerance or resistance, heat tolerance or resistance, low or high soil pH level tolerance, salt tolerance or resistance, resistance to an insect, resistance to a bacterial disease, resistance to a viral disease, resistance to a fungal disease, resistance to a nematode, resistance to a pest, male sterility, site-specific recombination, and abiotic stress tolerance.

When a transgenic plant provided herein, such as a plant (e.g., Brassica plant) expressing IPT7 from a TSS promoter, is crossed with another different variety, first generation (F1) progeny are produced. The hybrid progeny are produced regardless of characteristics of the two varieties produced. As such, an $F_1$ hybrid plant can be produced by crossing a transgenic plant provided herein, such as a plant (e.g., Brassica plant) expressing IPT7 from a TSS promoter, with any second plant. The second plant can be genetically homogeneous (e.g., inbred) or can itself be a hybrid. Therefore, the disclosure provides any $F_1$ hybrid plant produced by crossing a transgenic plant provided herein, such as a plant (e.g., Brassica plant) expressing IPT7 from a TSS promoter, with a second plant (such as a transgenic plant having one or more genes that confer to the plant one or more desired characteristics).

Plants can be crossed by either natural or mechanical techniques. Natural pollination occurs by self-pollination or natural cross pollination, which typically is aided by pollinating organisms. In either natural or artificial crosses, flowering and flowering time can be a consideration.

Sensitivity to day length can be a consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting. Plants can be grown in winter nurseries located at sea level in tropical latitudes where day lengths are shorter than their critical photoperiod. The short day lengths and warm temperatures encourage early flowering and seed maturation. Early flowering can be useful for generation advance when only a few self-pollinated seeds per plant are desired, but usually not for artificial hybridization because the flowers self-pollinate before they are large enough to manipulate for hybridization. Artificial lighting can be used to extend the natural day length to about 14.5 hours to obtain flowers suitable for hybridization and to increase yields of self-pollinated seed. The effect of a short photoperiod on flowering and seed yield can be partly offset by altitude. At tropical latitudes, varieties adapted to the northern U.S. perform more like those adapted to the southern U.S. at high altitudes than they do at sea level. The light level for delay of flowering can be dependent on the quality of light emitted from the source and the genotype being grown. For example, blue light with a wavelength of about 480 nm typically needs more than about 30 times the energy to inhibit flowering as red light with a wavelength of about 640 nm (Parker et al. 1946. *Bot. Gaz.* 108:1-26).

Temperature can also affect the flowering and development of plants. It can influence the time of flowering and suitability of flowers for hybridization. Artificial hybridization is typically successful between about 26° C. and about 32° C.

Self-pollination can occur naturally with no manipulation of the flowers. In some examples, the crossing of two plants is accomplished using artificial hybridization. In artificial hybridization, the flower used as a female in a cross is manually cross pollinated prior to maturation of pollen from the flower, thereby preventing self-fertilization, or alternatively, the male parts of the flower are emasculated using known methods. Exemplary methods for emasculating the male parts of a flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed, for example with forceps. Immature buds, such as those hidden under the stipules at the leaf axil, are removed. The calyx is removed, for example by grasping a sepal with the forceps, pulling it down and around the flower, and repeating the procedure until the five sepals are removed. The exposed corolla is removed, for example by grasping it just above the calyx scar, then lifting and wiggling the forceps simultaneously. The ring of anthers is visible after the corolla is removed, unless the anthers were removed with the petals. Cross-pollination can then be performed using, for example, petri dishes or envelopes in which male flowers have been collected. Desiccators containing calcium chloride crystals are used in some environments to dry male flowers to obtain adequate pollen shed.

Emasculation is not necessary to prevent self-pollination (Walker et al. 1979. *Crop Sci.* 19:285-286). When emasculation is not used, the anthers near the stigma can be removed to make the stigma visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Pollen is available from a flower with a recently opened corolla, but the degree of corolla opening associated with pollen shed can vary during the day. In many environments, collection and use of male flowers immediately without storage can be conducted. In the southern U.S. and other humid climates, pollen shed occurs in the morning when female flowers are more immature and difficult to manipulate than in the afternoon, and the flowers can be damp from heavy dew. In those circumstances, male flowers are collected into envelopes or petri dishes in the morning, and the open container is typically placed in a desiccator for about 4 hours at a temperature of about 25° C. The desiccator can be taken to the field in the afternoon and kept in the shade to prevent excessive temperatures from developing within it. Pollen viability can be maintained in flowers for up to about 2 days when stored at about 5° C. In a desiccator at about 3° C., flowers can be stored successfully for several weeks; however, varieties can differ in the percentage of pollen that germinates after long-term storage.

Either with or without emasculation of the female flower, hand pollination can be carried out by removing the stamens and pistil from a flower of the male parent and gently brushing the anthers against the stigma of the female flower. Access to the stamens can be achieved by removing the front sepal and keel petals or piercing the keel with closed forceps and allowing them to open to push the petals away. Brushing the anthers on the stigma causes them to rupture, and high percentages of successful crosses are typically obtained when pollen is clearly visible on the stigma. Pollen shed can be checked by tapping the anthers before brushing the stigma. Several male flowers can be used to obtain suitable pollen shed when conditions are unfavorable, or the same male can be used to pollinate several flowers with good pollen shed.

When male flowers are not collected and dried in a desiccator, the parents of a cross can be planted adjacent to each other. Plants are typically grown in rows about 65 cm to about 100 cm apart, but plant densities for seed production fields can be significantly higher in density without compromising fertilization and seed quality. Yield of self-pollinated seed from an individual plant can range from a few seeds to more than about 1,000 as a function of plant density. A density of about 30 plants/m of row can be used when about 30 or fewer seeds per plant is adequate, about 10 plants/m can be used to obtain about 100 seeds/plant, and about 3 plants/m usually results in a high seed production per plant. Densities of about 12 plants/m or less can be used for artificial hybridization.

Multiple planting dates about 7 days to about 14 days apart can typically be used to match parents of different flowering dates. When differences in flowering dates are extreme between parents, flowering of the later parent can be hastened by creating an artificially short day. Alternatively, flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 hours for about 15 days beginning when there are three nodes with trifoliate leaves on the main stem. Plants induced to flower early tend to have flowers that self-pollinate when they are small and can be difficult to prepare for hybridization. Grafting can be used to hasten the flowering of late flowering genotypes.

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, Plant Breeding Methodology, John Wiley & Sons, Inc. (1988). For population improvement methods specific for soybean see, e.g., J. R. Wilcox, editor (1987) SOYBEANS: Improvement, Production, and Uses, Second Edition, American Society of Agronomy, Inc., Crop Science Society of America, Inc., and Soil Science Society of America, Inc., publishers, 888 pages.

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids. As discussed above, hybrid is an individual plant resulting from a cross between parents of differing genotypes. Commercial hybrids are now used extensively in many crops, including corn (maize), sorghum, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA). BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences, USA*, 99:9828-9832) and Quarrie et al. (Quarrie et al., Bulk segregant analysis with molecular markers and its use for improving drought resistance in maize, 1999, *Journal of Experimental Botany*, 50(337): 1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding. The method to combine into a single genotype a series of target genes identified in different parents is usually referred as gene pyramiding. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

VI. Gene Editing

As used herein, the term "gene editing system" refers to a system comprising one or more DNA-binding domains or components and one or more DNA-modifying domains or components, or isolated nucleic acids, e.g., one or more vectors, encoding said DNA-binding and DNA-modifying domains or components. Gene editing systems are used for modifying the nucleic acid of a target gene and/or for modulating the expression of a target gene. In known gene editing systems, for example, the one or more DNA-binding domains or components are associated with the one or more DNA-modifying domains or components, such that the one or more DNA-binding domains target the one or more DNA-modifying domains or components to a specific nucleic acid site. Methods and compositions for enhancing gene editing is well known in the art. See example, U.S. Patent Application Publication No. 2018/0245065, which is incorporated by reference in its entirety.

Certain gene editing systems are known in the art, and include but are not limited to, zinc finger nucleases, transcription activator-like effector nucleases (TALENs); clustered regularly interspaced short palindromic repeats (CRISPR)/Cas systems, meganuclease systems, and viral vector-mediated gene editing.

In some embodiments, the present disclosure teaches methods for gene editing/cloning utilizing DNA nucleases. CRISPR complexes, transcription activator-like effector nucleases (TALENs), zinc finger nucleases (ZFNs), and FokI restriction enzymes, which are some of the sequence-specific nucleases that have been used as gene editing tools. These enzymes are able to target their nuclease activities to desired target loci through interactions with guide regions engineered to recognize sequences of interest. In some embodiments, the present disclosure teaches CRISPR-based gene editing methods to genetically engineer the genome of plant species of the present disclosure in order to stimulate, enhance, or modulate suberin content of plant cells, plant tissues, plant parts or whole plants.

(i) CRISPR Systems

CRISPR (Clustered Regularly Interspaced Short Palindromic Repeats) and CRISPR-associated (cas) endonucleases were originally discovered as adaptive immunity systems evolved by bacteria and archaea to protect against viral and plasmid invasion. Naturally occurring CRISPR/Cas systems in bacteria are composed of one or more Cas genes and one or more CRISPR arrays consisting of short palindromic repeats of base sequences separated by genome-targeting sequences acquired from previously encountered viruses and plasmids (called spacers). (Wiedenheft, B et. al. Nature. 2012; 482:331; Bhaya, D., et. al., Annu. Rev. Genet. 2011; 45:231; and Terns, M. P. et. al., Curr. Opin. Microbiol. 2011; 14:321). Bacteria and archaea possessing one or more CRISPR loci respond to viral or plasmid challenge by integrating short fragments of foreign sequence (protospacers) into the host chromosome at the proximal end of the CRISPR array. Transcription of CRISPR loci generates a library of CRISPR-derived RNAs (crRNAs) containing sequences complementary to previously encountered invading nucleic acids (Haurwitz, R. E., et. al., Science. 2012:329; 1355; Gesner, E. M., et. al., Nat. Struct. Mol. Biol. 2001, 18:688; Jinek, M., et. al., Science. 2012:337; 816-21). Target recognition by crRNAs occurs through complementary base pairing with target DNA, which directs cleavage of foreign sequences by means of Cas proteins. (Jinek et. al. 2012 "A Programmable dual-RNA-guided DNA endonuclease in adaptive bacterial immunity." Science. 2012:337; 816-821).

There are at least five main CRISPR system types (Type I, II, III, IV and V) and at least 16 distinct subtypes (Makarova, K. S., et al., Nat Rev Microbiol. 2015. Nat. Rev. Microbiol. 13, 722-736). CRISPR systems are also classified based on their effector proteins. Class 1 systems possess multi-subunit crRNA-effector complexes, whereas in Class 2 systems all functions of the effector complex are carried out by a single protein (e.g., Cas9 or Cpf1). In some embodiments, the present disclosure provides using type II and/or type V single-subunit effector systems.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, which processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cm' or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) Science 341: 833-836.

(ii) CRISPR/Cas9

In some embodiments, the present disclosure provides methods of gene editing using a Type II CRISPR system. Type II systems rely on a i) single endonuclease protein, ii) a transactivating crRNA (tracrRNA), and iii) a crRNA where a ~20-nucleotide (nt) portion of the 5' end of crRNA is complementary to a target nucleic acid. The region of a CRISPR crRNA strand that is complementary to its target DNA protospacer is hereby referred to as "guide sequence."

In some embodiments, the tracrRNA and crRNA components of a Type II system can be replaced by a single guide RNA (sgRNA), also known as a guide RNA (gRNA). The sgRNA can include, for example, a nucleotide sequence that comprises an at least 12-20 nucleotide sequence complementary to the target DNA sequence (guide sequence) and can include a common scaffold RNA sequence at its 3' end. As used herein, "a common scaffold RNA" refers to any RNA sequence that mimics the tracrRNA sequence or any RNA sequences that function as a tracrRNA.

Cas9 endonucleases produce blunt end DNA breaks and are recruited to target DNA by a combination of a crRNA and a tracrRNA oligos, which tether the endonuclease via complementary hybridization of the RNA CRISPR complex.

In some embodiments, DNA recognition by the crRNA/endonuclease complex requires additional complementary base-pairing with a protospacer adjacent motif (PAM) (e.g., 5'-NGG-3') located in a 3' portion of the target DNA, downstream from the target protospacer. (Jinek, M., et. al., Science. 2012, 337:816-821). In some embodiments, the PAM motif recognized by a Cas9 varies for different Cas9 proteins.

In some embodiments the Cas9 disclosed herein can be any variant derived or isolated from any source. In other embodiments, the Cas9 peptide of the present disclosure can include one or more of the mutations described in the literature, including but not limited to the functional mutations described in: Fonfara et al. Nucleic Acids Res. 2014 February; 42(4):2577-90; Nishimasu H. et al. Cell. 2014

Feb. 27,156(5):935-49; Jinek M. et al. Science. 2012 337: 816-21; and Jinek M. et al. Science. 2014 Mar. 14, 343 (6176); see also U.S. patent application Ser. No. 13/842,859, filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference. Thus, in some embodiments, the systems and methods disclosed herein can be used with the wild-type Cas9 protein having double-stranded nuclease activity, Cas9 mutants that act as single stranded nickases, or other mutants with modified nuclease activity.

According to the present disclosure, Cas9 molecules of, derived from, or based on the Cas9 proteins of a variety of species can be used in the methods and compositions described herein. For example, Cas9 molecules of, derived from, or based on, e.g., *S. pyogenes, S. thermophilus, Staphylococcus aureus* and/or *Neisseria meningitidis* Cas9 molecules, can be used in the systems, methods and compositions described herein. Additional Cas9 species include: *Acidovorax avenae, Actinobacillus pleuropneumoniae, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhiz obium* sp., *Brevibacillus latemsporus, Campylobacter coli, Campylobacter jejuni, Campylobacter lad, Candidatus puniceispirillum, Clostridium cellulolyticum, Clostridium perfringens, Corynebacterium accolens, Corynebacterium diphtheria, Corynebacterium matruchotii, Dinoroseobacter sliibae, Eubacterium dolichum, Gamma proteobacterium, Gluconacetobacler diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica. Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tislrella mobilis, Treponema* sp., or *Verminephrobacter eiseniae.*

In some embodiments, the present disclosure teaches the use of tools for genome editing techniques in plants such as crops and methods of gene editing using CRISPR-associated (cas) endonucleases including SpyCas9, SaCas9, St1Cas9. These powerful tools for genome editing, which can be applied to plant genome editing are well known in the art. See example, Song et al. (2016), CRISPR/Cas9: A powerful tool for crop genome editing, *The Crop Journal* 4:75-82, Mali et al. (2013) RNA-guided human genome engineering via cas9, Science 339: 823-826; Ran et al. (2015) In vivo genome editing using *Staphylococcus aureus* cas9, Nature 520: 186-191; Esvelt et al. (2013) Orthogonal cas9 proteins for rna-guided gene regulation and editing, Nature methods 10(11): 1116-1121, each of which is hereby incorporated by reference in its entirety for all purposes.

(iii) CRISPR/Cpf1

In other embodiments, the present disclosure provides methods of gene editing using a Type V CRISPR system. In some embodiments, the present disclosure provides methods of gene editing using CRISPR from *Prevotella, Francisella, Acidaminococcus*, Lachnospiraceae, and *Moraxella* (Cpf1).

The Cpf1 CRISPR systems of the present disclosure comprise i) a single endonuclease protein, and ii) a crRNA, wherein a portion of the 3' end of crRNA contains the guide sequence complementary to a target nucleic acid. In this system, the Cpf1 nuclease is directly recruited to the target DNA by the crRNA. In some embodiments, guide sequences for Cpf1 must be at least 12 nt, 13 nt, 14 nt, 15 nt, or 16 nt in order to achieve detectable DNA cleavage, and a minimum of 14 nt, 15 nt, 16 nt, 17 nt, or 18 nt to achieve efficient DNA cleavage.

The Cpf1 systems of the present disclosure differ from Cas9 in a variety of ways. First, unlike Cas9, Cpf1 does not require a separate tracrRNA for cleavage. In some embodiments, Cpf1 crRNAs can be as short as about 42-44 bases long—of which 23-25 nt is guide sequence and 19 nt is the constitutive direct repeat sequence. In contrast, the combined Cas9 tracrRNA and crRNA synthetic sequences can be about 100 bases long.

Second, certain Cpf1 systems prefer a "TTN" PAM motif that is located 5' upstream of its target. This is in contrast to the "NGG" PAM motifs located on the 3' of the target DNA for common Cas9 systems such as *Streptococcus pyogenes* Cas9. In some embodiments, the uracil base immediately preceding the guide sequence cannot be substituted (Zetsche, B. et al. 2015. "Cpf1 Is a Single RNA-Guided Endonuclease of a Class 2 CRISPR-Cas System" Cell 163, 759-771, which is hereby incorporated by reference in its entirety for all purposes).

Third, the cut sites for Cpf1 are staggered by about 3-5 bases, which create "sticky ends" (Kim et al., 2016. "Genome-wide analysis reveals specificities of Cpf1 endonucleases in human cells" published online Jun. 6, 2016). These sticky ends with 3-5 nt overhangs are thought to facilitate NHEJ-mediated-ligation and improve gene editing of DNA fragments with matching ends. The cut sites are in the 3' end of the target DNA, distal to the 5' end where the PAM is. The cut positions usually follow the 18th base on the non-hybridized strand and the corresponding 23rd base on the complementary strand hybridized to the crRNA.

Fourth, in Cpf1 complexes, the "seed" region is located within the first 5 nt of the guide sequence. Cpf1 crRNA seed regions are highly sensitive to mutations, and even single base substitutions in this region can drastically reduce cleavage activity (see Zetsche B. et al. 2015 "Cpf1 Is a Single RNA-Guided Endonuclease of a Class 2 CRISPR-Cas System" Cell 163, 759-771). Critically, unlike the Cas9 CRISPR target, the cleavage sites and the seed region of Cpf1 systems do not overlap. Additional guidance on designing Cpf1 crRNA targeting oligos is available on Zetsche B. et al. 2015. ("Cpf1 Is a Single RNA-Guided Endonuclease of a Class 2 CRISPR-Cas System" Cell 163, 759-771).

(iv) Guide RNA (gRNA)

In some embodiments, the guide RNA of the present disclosure comprises two coding regions, encoding for crRNA and tracrRNA, respectively. In other embodiments, the guide RNA is a single guide RNA (sgRNA) synthetic crRNA/tracrRNA hybrid. In other embodiments, the guide RNA is a crRNA for a Cpf1 endonuclease.

Persons having skill in the art will appreciate that, unless otherwise noted, all references to a single guide RNA (sgRNA) in the present disclosure can be read as referring to a guide RNA (gRNA). Therefore, embodiments described in the present disclosure which refer to a single guide RNA (sgRNA) will also be understood to refer to a guide RNA (gRNA).

The guide RNA is designed so as to recruit the CRISPR endonuclease to a target DNA region. In some embodiments, the present disclosure teaches methods of identifying viable target CRISPR landing sites and designing guide RNAs for targeting the sites. For example, in some embodiments, the present disclosure teaches algorithms designed to facilitate the identification of CRISPR landing sites within target DNA regions.

In some embodiments, the present disclosure teaches use of software programs designed to identify candidate CRISPR target sequences on both strands of an input DNA sequence based on desired guide sequence length and a CRISPR motif sequence (PAM, protospacer adjacent motif) for a specified CRISPR enzyme. For example, target sites for Cpf1 from *Francisella novicida* U112, with PAM sequences TTN, may be identified by searching for 5'-TTN-3' both on the input sequence and on the reverse-complement of the input. The target sites for Cpf1 from Lachnospiraceae bacterium and *Acidaminococcus* sp., with PAM sequences TTTN, may be identified by searching for 5'-TTTN-3' both on the input sequence and on the reverse complement of the input. Likewise, target sites for Cas9 of *S. thermophilus* CRISPR, with PAM sequence NNAGAAW, may be identified by searching for 5'-Nx-NNAGAAW-3' both on the input sequence and on the reverse-complement of the input. The PAM sequence for Cas9 of *S. pyogenes* is 5'-NGG-3'.

Since multiple occurrences in the genome of the DNA target site may lead to nonspecific genome editing, after identifying all potential sites, sequences may be filtered out based on the number of times they appear in the relevant reference genome or modular CRISPR construct. For those CRISPR enzymes for which sequence specificity is determined by a 'seed' sequence (such as the first 5 bp of the guide sequence for Cpf1-mediated cleavage) the filtering step may also account for any seed sequence limitations.

In some embodiments, algorithmic tools can also identify potential off target sites for a particular guide sequence. For example, in some embodiments Cas-Offinder can be used to identify potential off target sites for Cpf1 (see Kim et al., 2016. "Genome-wide analysis reveals specificities of Cpf1 endonucleases in human cells" Nature Biotechnology 34, 863-868). Any other publicly available CRISPR design/identification tool may also be used, including for example the Zhang lab crispr.mit.edu tool (see Hsu, et al. 2013 "DNA targeting specificity of RNA guided Cas9 nucleases" Nature Biotech 31, 827-832).

In some embodiments, the user may be allowed to choose the length of the seed sequence. The user may also be allowed to specify the number of occurrences of the seed: PAM sequence in a genome for purposes of passing the filter. The default is to screen for unique sequences. Filtration level is altered by changing both the length of the seed sequence and the number of occurrences of the sequence in the genome. The program may in addition or alternatively provide the sequence of a guide sequence complementary to the reported target sequence(s) by providing the reverse complement of the identified target sequence(s).

In the guide RNA, the "spacer/guide sequence" sequence is complementary to the "proto spacer" sequence in the DNA target. The gRNA "scaffold" for a single stranded gRNA structure is recognized by the Cas9 protein.

In some embodiments, the transgenic plant, plant part, plant cell, or plant tissue culture taught in the present disclosure comprise a recombinant construct, which comprises at least one nucleic acid sequence encoding a guide RNA. In some embodiments, the nucleic acid is operably linked to a promoter. In other embodiments, a recombinant construct further comprises a nucleic acid sequence encoding a Clustered regularly interspaced short palindromic repeats (CRISPR) endonuclease. In other embodiments, the guide RNA is capable of forming a complex with said CRISPR endonuclease, and said complex is capable of binding to and creating a double strand break in a genomic target sequence of said plant genome. In other embodiments, the CRISPR endonuclease is Cas9.

In some embodiments, the modified plant cells comprise one or more modifications (e.g., insertions, deletions, or mutations of one or more nucleic acids) in the genomic DNA sequence of an endogenous target gene resulting in the altered function the endogenous gene, thereby modulating, stimulating, or enhancing suberin content in plant cells, plant tissues, plant parts and whole plants. In such embodiments, the modified plant cells comprise a "modified endogenous target gene." In some embodiments, the modifications in the genomic DNA sequence cause mutation, thereby altering the function of the protein. In some embodiments, the modifications in the genomic DNA sequence results in amino acid substitutions, thereby altering the normal function of the encoded protein. In some embodiments, the modifications in the genomic DNA sequence encode a modified endogenous protein with modulated, altered, stimulated or enhanced function compared to the unmodified version of the endogenous protein.

In some embodiments, the modified plant cells described herein comprise one or more modified endogenous target genes, wherein the one or more modifications result in an altered function of a gene product (i.e., a protein) encoded by the endogenous target gene compared to an unmodified plant cell. For example, in some embodiments, a modified plant cell demonstrates expression of a protein or an upregulated expression of said protein. In some embodiments, the expression of the gene product in a modified plant cell is enhanced by at least 0.5%, 1%, 2%, 3%, 4%, 5% or higher compared to the expression of the gene product in an unmodified plant cell. In other embodiments, the expression of the gene product in a modified plant cell is enhanced by at least 10%, 20%, 30%, 40%, 50%, 60%, 70%, 80%, 90%, or more compared to the expression of the gene product in an unmodified plant cell. In some embodiments, the modified plant cells described herein demonstrate enhanced expression and/or function of gene products encoded by a plurality (e.g., two or more) of endogenous target genes compared to the expression of the gene products in an unmodified plant cell. For example, in some embodiments, a modified plant cell demonstrates enhanced expression and/or function of gene products from 2, 3, 4, 5, 6, 7, 8, 9, 10, or more endogenous target genes compared to the expression of the gene products in an unmodified plant cell.

In some embodiments, the modified plant cells described herein comprise one or more modified endogenous target genes, wherein the one or more modifications to the target DNA sequence results in expression of a protein with reduced or altered function (e.g., a "modified endogenous protein") compared to the function of the corresponding protein expressed in an unmodified plant cell (e.g., a "unmodified endogenous protein"). In some embodiments, the modified plant cells described herein comprise 2, 3, 4, 5, 6, 7, 8, 9, 10, or more modified endogenous target genes encoding 2, 3, 4, 5, 6, 7, 8, 9, 10, or more modified endogenous proteins. In some embodiments, the modified endogenous protein demonstrates enhanced or altered binding affinity for another protein expressed by the modified plant cell or expressed by another cell; enhanced or altered signaling capacity; enhanced or altered enzymatic activity; enhanced or altered DNA-binding activity; or reduced or altered ability to function as a scaffolding protein.

VII. Plants Having One or More Desired Heritable Traits

The disclosure provides transgenic plants, such as a plant (e.g., *Brassica* plant) expressing IPT7 from a TSS promoter, which can be further modified to include one or more additional desired heritable traits. In some examples, such plants can be developed using backcrossing or genetic engineering (for example by introducing one or more transgenes into a transgenic plant provided herein, such as a plant (e.g., *Brassica* plant) expressing IPT7 from a TSS promoter wherein the transgenes encode one or more desired traits), wherein essentially all of the desired morphological and physiological characteristics of a disclosed transgenic plant are recovered (such as increased root mass) in addition to a genetic locus transferred into the plant via the backcrossing technique. Plants developed using such methods can be referred to as a single locus converted plant.

In one example, the method of introducing one or more desired traits into one or more of the transgenic plants provided herein, such as a plant (e.g., *Brassica* plant) expressing IPT7 from a TSS promoter, with a second plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of the transgenic variety to produce backcross progeny plants; (d) selecting backcross progeny plants that have the one or more desired traits and physiological and morphological characteristics of a transgenic variety to produce selected backcross progeny plants; and (e) repeating steps (c) and (d) one or more times in succession to produce selected second or higher backcross progeny plants that have the one or more desired traits and the physiological and morphological characteristics of a transgenic plant provided herein, such as a plant (e.g., *Brassica* plant) expressing IPT7 from a TSS promoter, when grown in the same environmental conditions.

Backcrossing methods can be used to improve or introduce a characteristic into a transgenic plant provided herein, such as a plant (e.g., *Brassica* plant) expressing IPT7 from a TSS promoter. The parental plant, which contributes the locus for the desired characteristic, is termed the "nonrecurring" or "donor" parent. This terminology refers to the fact that the nonrecurring parent is used one time in the backcross protocol and therefore does not recur. The parental plant to which the locus or loci from the nonrecurring parent are transferred is known as the recurrent parent as it is used for several rounds in the backcrossing protocol (Poehlman and Sleper. 1995. "Breeding Field Crops" Ames, Iowa: Iowa State University Press; Sprague and Dudley, eds. 1988. Corn and Improvement, 3rd edition). In a typical backcross protocol, the original variety of interest (e.g., transgenic plant provided herein, such as a plant (e.g., *Brassica* plant) expressing IPT7 from a TSS promoter) is crossed to a second variety (nonrecurring parent) that carries the single locus of interest (such as a desirable trait) to be transferred. The resulting progeny from this cross are then crossed again to the recurrent parent and the process is repeated until a plant is obtained wherein essentially all of the desired morphological and physiological characteristics of the recurrent parent (e.g., the transgenic plant provided herein, such as a plant (e.g., *Brassica* plant) expressing IPT7 from a TSS promoter) are recovered (such as increased root mass) in the converted plant, in addition to the single transferred locus from the nonrecurring parent.

A backcross protocol alters or substitutes a single trait or characteristic in the original variety, such as a transgenic plant provided herein, such as a plant (e.g., *Brassica* plant) expressing IPT7 from a TSS promoter. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent can depend on the purpose of the backcross; for example, to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield or root mass in extensive replicated tests. In general, four or more backcrosses are used when there is no evaluation of the progeny for specific traits, such as yield. As in this example, lines with the phenotype of the recurrent parent can be composited without the usual replicated tests for traits such as yield or root mass, in the individual lines.

Varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease, insect resistance, restoration of male fertility, enhanced nutritional quality, modified phosphorus characteristics, modified antioxidant characteristics, yield stability, and yield enhancement. These comprise genes generally inherited through the nucleus. Thus, plants of a transgenic plant provided herein, such as a plant (e.g., *Brassica* plant) expressing IPT7 from a TSS promoter, or progeny thereof, which include a single locus conversion (such as one that confers a desired trait, such as increased root mass).

Direct selection can be applied where the single locus acts as a dominant trait. An example of a dominant trait is the herbicide resistance trait (such as glyphosate resistance). For the selection process, the progeny of the initial cross are sprayed with a herbicide (such as RoundUp® herbicide) prior to the backcrossing. The spraying eliminates any plants which do not have the desired herbicide resistance characteristic; only those plants which have the herbicide resistance gene are used in the subsequent backcross. This process is then repeated for all additional backcross generations.

Selection of plants for breeding may not be dependent on the phenotype of a plant and instead can be based on genetic investigations. For example, a suitable genetic marker can be used which is genetically-linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to plant breeding are well known. Such methods can be useful in the case of recessive traits and variable phenotypes, or where conventional assays are more expensive, time consuming, or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, which is incorporated herein by reference in its entirety), and Single Nucleotide Polymorphisms (SNPs).

Qualitative characteristics can also be useful as phenotype-based genetic markers in plants; however, some or many may not differ among varieties commonly used as parents. Exemplary genetic markers include flower color, differences in maturity, height, and pest resistance.

Useful or desirable traits can be introduced by backcrossing, as well as directly into a plant by genetic transformation methods. Genetic transformation can therefore be used to insert a selected transgene into a transgenic plant provided herein, such as a plant (e.g., *Brassica* plant) expressing IPT7 from a TSS promoter, or progeny thereof, or can, alternatively, be used for the preparation of transgenes which can be introduced by backcrossing. Thus, the disclosure provides methods of producing a plant of a transgenic plant provided herein, such as a plant (e.g., *Brassica* plant) expressing IPT7 from a TSS promoter, or progeny thereof, that includes one or more added desired traits, for example that include introducing a transgene(s) conferring the one or more desired traits into a transgenic plant provided herein, such as a plant (e.g., *Brassica* plant) expressing IPT7 from a TSS promoter, or progeny thereof (for example by transformation with a transgene that confers upon the plant the desired trait), thereby producing a transgenic plant provided herein, such as a plant (e.g., *Brassica* plant) expressing IPT7 from a TSS promoter, or progeny thereof that includes the one or more added desired traits.

Methods for the transformation of plants, including tobacco and *Brassica*, are known. Methods for introducing a desired nucleic acid molecule (e.g., transgene), such as DNA or RNA which can be employed for the genetic transformation of plants include, but are not limited to, electroporation, microprojectile bombardment, *Agrobacterium*-mediated transformation and direct DNA uptake by protoplasts.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner. Protoplasts can also be employed for electroporation transformation of plants (Bates. 1994. *Mol. Biotechnol.* 2(2):135-145; Lazzeri. 1995. *Methods Mol. Biol.* 49:95-106).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target plant cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large.

*Agrobacterium*-mediated transfer is a method for introducing gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is known (e.g., Fraley et al. 1985. *Bio. Tech.* 3(7):629-635; U.S. Pat. No. 5,563,055). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189): 454-457).

In one example, such methods can also be used to introduce transgenes for the production of proteins in transgenic plant cells. The resulting produced protein can be harvested from the transgenic plant. The transgene can be harvested from the transgenic plants that are originated or are descended from a transgenic plant provided herein, such as a plant (e.g., *Brassica* plant) expressing IPT7 from a TSS promoter, a seed of such a plant, or a hybrid progeny of such a plant.

Numerous different genes are known and can be introduced into a transgenic plant provided herein, such as a plant (e.g., tobacco or *Brassica* plant) expressing IPT7 from a TSS promoter, or progeny thereof. Non-limiting examples of particular genes and corresponding phenotypes that can be chosen for introduction into a plant are provided herein.

Herbicide Resistance. A herbicide resistance gene can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to an herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) can be used (e.g., see U.S. Pat. No. 4,940,835). Examples of specific EPSPS transformation events conferring glyphosate resistance are described, for example, in U.S. Pat. No. 6,040,497.

DNA molecules encoding a mutant aroA gene are known (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of gene-edited plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Exemplary genes conferring resistance to an herbicide that inhibits photosynthesis include triazine (psbA and gs+genes) and benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseudomonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is well known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

Disease Resistance. Plant defenses are often activated by specific interaction between the product of a disease resistance gene (R) in the plant and the product of a corresponding avirulence (Avr) gene in the pathogen. A plant, such as a transgenic plant provided herein, such as a plant (e.g., tobacco plant) expressing IPT7 from a TSS promoter, or progeny thereof, can be transformed with cloned resistance gene to engineer plants that are resistant to specific pathogen strains. See, for example Jones et al. (1994. *Science* 266: 789) (tomato Cf-9 gene for resistance to *Cladosporium fulvum*); Martin et al. (1993. *Science* 262(5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclosed that transgenic plants expressing a barley ribosome-inactivating gene have an increased resistance to fungal disease.

Insect Resistance. One example of an insect resistance gene includes a *Bacillus thuringiensis* (Bt) protein, a derivative thereof or a synthetic polypeptide modeled thereon (e.g., see Geiser et al., 1986. *Gene* 48:109, discloses a Bt Δendotoxin gene). Moreover, DNA molecules encoding A-endotoxin genes can be obtained from the ATCC (Manassas, VA), for example under ATCC Accession Nos. 40098, 67136, 31995 and 31998. Another example is a lectin. See, for example, Van Damme et al. (1994. *Plant Mol Biol* 24(5):825-830), which discloses several *Clivia miniata* mannose-binding lectin genes. A vitamin-binding protein can also be used, such as avidin. See WIPO Publication No. WO 1994/000992, which teaches the use of avidin and avidin homologues as larvicides against insect pests.

In one example the insect resistance gene is an enzyme inhibitor, for example, a protease, proteinase inhibitor, or an α-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. *Nature* 344:458-461; discloses juvenile hormone esterase, an inactivator of juvenile hormone).

Still other examples include an insect-specific antibody or an immunotoxin derived therefrom and a developmental-arrestive protein. See Taylor et al. (1994. Seventh Intl.

Symposium on Molecular Plant-Microbe Interactions (Edinburgh Scotland), Abstract #497), who described enzymatic inactivation in transgenic tobacco via production of single-chain antibody fragments.

Male Sterility. Genetic male sterility can increase the efficiency with which hybrids are made, in that it can eliminate the need to physically emasculate the plant used as a female in a given cross (Brim and Stuber. 1973. *Crop Sci.* 13:528-530). Herbicide-inducible male sterility systems are known (e.g., U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile F1 hybrid progeny. If no restorer gene is present in the male parent, male-sterile hybrids are obtained. Such hybrids are useful where the vegetative tissue of the plant is utilized. However, in many cases, the seeds are considered to be a valuable portion of the crop, thus, it is desirable to restore the fertility of the hybrids in these crops. Therefore, the disclosure provides a transgenic plant provided herein, such as a plant (e.g., tobacco plant) expressing IPT7 from a TSS promoter, comprising a genetic locus capable of restoring male fertility in an otherwise male-sterile plant. Examples of male-sterility genes and corresponding restorers which can be employed are known (see, e.g., U.S. Pat. Nos. 5,530,191 and 5,684,242).

VIII. Tissue Cultures and In Vitro Regeneration of Plants

Tissue cultures of one or more of the transgenic plants provided herein, such as a plant (e.g., tobacco plant) expressing IPT7 from a TSS promoter, are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, petiole, stein, ovule, cotyledon, hypocotyl, shoot or stem, and the like. In a particular example, the tissue culture includes embryos, protoplasts, meristematic cells, pollen, leaves or anthers of the transgenic plants provided herein, such as a plant (e.g., tobacco plant) expressing IPT7 from a TSS promoter. Also provided are plants regenerated from such tissue cultures, wherein the regenerated plant expresses the physiological and morphological characteristics of a new transgenic plant disclosed herein (e.g., one having increased root mass).

Methods for preparing tissue cultures of regenerable plant cells and regenerating plants therefrom, are known, such as those disclosed in U.S. Pat. Nos. 4,992,375; 5,015,580; 5,024,944, and 5,416,011. Tissue culture provides the capability to regenerate fertile plants. This can allow, for example, transformation of the tissue culture cells followed by regeneration of transgenic plants. For transformation to be efficient and successful, DNA can be introduced into cells that give rise to plants or germ-line tissue.

Plants can be regenerated using organogenesis or somatic embryogenesis. Organogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Organogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in organogenesis may not generate many somatic embryos, while lines that produce large numbers of embryos during an "induction" step (typically, exposure of the plant material to a specific regimen of plant growth regulators) may not give rise to rapidly-growing proliferative cultures. In addition to line-specific responses, proliferative cultures can be observed with both shoot morphogenesis and somatic embryogenesis. Proliferation allows a single, transformed cell to multiply to the point that it can contribute to germ-line tissue.

Organogenesis is a system whereby shoots are obtained de novo from cotyledonary nodes of seedlings (Wright et al., 1986. *Plant Cell Reports* 5:150-154). The shoot meristems form subepidermally and morphogenic tissue can proliferate on a medium containing benzyl adenine (BA). This system can be used for transformation if the subepidermal, multicellular origin of the shoots is recognized and proliferative cultures are utilized. Tissue that can give rise to new shoots are targeted and proliferated within the meristematic tissue to lessen problems associated with chimerism.

Somatic embryogenesis is a system in which embryogenic tissue is obtained from the zygotic embryo axis (Christianson et al., 1983. *Science* 222:632-634). The embryogenic cultures are proliferative and the proliferative embryos are of apical or surface origin with a small number of cells contributing to embryo formation. The origin of primary embryos (the first embryos derived from the initial explant) is dependent on the explant tissue and the auxin levels in the induction medium (Hartweck et al., 1988. *In Vitro Cell. Develop. Bio.* 24:821-828). With proliferative embryonic cultures, single cells or small groups of surface cells of the "older" somatic embryos form the "newer", more recently developed somatic embryos.

Embryogenic cultures can also be used for regeneration, including regeneration of transgenic plants.

IV. Products

The disclosure provides products obtained from one or more of the transgenic plants provided herein, such as a plant (e.g., tobacco or *Brassica* plant) expressing IPT7 from a TSS promoter, or progeny thereof. Exemplary products include a biomass or part thereof, such as an extract, oil, protein isolate, protein concentrate, oil extract, or leaves. For example, a dried biomass and/or leaves of one or more of the transgenic plants provided herein, such as a plant (e.g., tobacco plant) expressing IPT7 from a TSS promoter, or progeny thereof can be used as part of an animal feed, food, beverage, tobacco-based product, or a cannabis/hemp-based product. In some examples, the product includes at least one cell, DNA, and/or protein of a transgenic plant provided herein, such as a plant (e.g., tobacco, cannabis/hemp, or *Brassica* plant) expressing IPT7 from a TSS promoter.

The disclosure provides containers, such as a glass, paper, or plastic container, which includes leaves of a transgenic plant provided herein, such as a plant (e.g., tobacco or cannabis/hemp plant) expressing IPT7 from a TSS promoter. The leaves can be dried, frozen, or fresh.

Provided herein is a product from oil or an oil extract of more of the transgenic plants provided herein, such as a plant (e.g., *Brassica* plant) expressing IPT7 from a TSS promoter, or progeny thereof.

Further Numbered Embodiments of the Disclosure

Other subject matter contemplated by the present disclosure is set out in the following numbered embodiments:

1. An isolated transgenic nucleic acid molecule, comprising:
    a TPR-domain suppressor of STIMPY (TSS) promoter operably linked to an isopentenyl-transferase 7 (IPT7) coding sequence.
2. The isolated transgenic nucleic acid molecule of embodiment 1, wherein the TSS promoter comprises at least 80%, at least 90%, at least 95%, at least 96%, at least 97%, at least 98%, at least 99%, or 100% sequence identity to SEQ ID NO: 1.
3. The isolated transgenic nucleic acid molecule of embodiment 1, wherein the IPT7 coding sequence comprises
    at least 80%, at least 90%, at least 95%, at least 96%, at least 97%, at least 98%, at least 99%, or 100% sequence identity to SEQ ID NO: 2; or
    at least 80%, at least 90%, at least 95%, at least 96%, at least 97%, at least 98%, at least 99%, or 100% sequence identity to nucleotides 90 to 1079 to SEQ ID NO: 2.
4. The isolated transgenic nucleic acid molecule of embodiment 1, wherein the IPT7 coding sequence encodes a protein comprising at least 80%, at least 90%, at least 95%, at least 96%, at least 97%, at least 98%, at least 99%, or 100% sequence identity to SEQ ID NO: 4.
5. A vector comprising the isolated transgenic nucleic acid molecule of any one of embodiments 1-4.
6. The vector of embodiment 5, wherein the vector is a plasmid vector not found in plants.
7. The vector of embodiment 5 or 6, wherein the vector comprises at least 80%, at least 90%, at least 95%, at least 96%, at least 97%, at least 98%, at least 99%, or 100% sequence identity SEQ ID NO: 3.
8. An isolated transgenic plant cell comprising the isolated transgenic nucleic acid molecule of any one of embodiments 1-4 or the vector of any one of embodiments 5-7.
9. A transgenic plant, comprising:
    the isolated transgenic nucleic acid molecule of any one of embodiments 1-4;
    the vector of any one of embodiments 5-7; or
    the plant cell of embodiment 8.
10. A transgenic plant part, comprising:
    the isolated transgenic nucleic acid molecule of any one of embodiment 1-4;
    the vector of any one of embodiments 5-7; or
    the plant cell of embodiment 8.
11. The isolated transgenic plant cell of embodiment 8, the transgenic plant of embodiment 9, or transgenic plant part of embodiment 10, wherein the isolated transgenic plant cell, transgenic plant, or transgenic plant part, is or is from a dicot.
12. The isolated transgenic plant cell, transgenic plant, or transgenic plant part of embodiment 11, wherein the dicot is a canola, tobacco, legume (e.g., pea, bean, lentil, or peanut), daisy, mint, lettuce, tomato, radish, alfalfa, pennycress, clover, rose bush, sunflower, and squash.
13. The transgenic plant of embodiment 9, wherein the transgenic plant expresses at least about at least 50%, at least 60%, at least 70%, at least 80%, at least 90%, at least 100%, at least 200%, at least 300%, at least 400%, at least 500%, or at least 1000% greater levels of IPT7 in mesophyll cells of developing leaves as compared to a wild-type plant.
14. The transgenic plant of embodiment 9 or 13, wherein the transgenic plant comprises:
    at least about 5%, at least 6%, at least 7%, at least 8%, at least 9%, at least 10%, at least 11%, at least 12%, at least 13%, at least 14%, at least 15%, at least 16%, at least 17%, at least 18%, at least 19% or at least 20% more cells in the root meristematic zone at seedling stage as compared to a wild-type plant;
    at least about 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29% or at least 30% greater root biomass as compared to a wild-type plant;
    no significant decrease in above ground growth as compared to a wild-type plant; or
    combinations thereof.
15. A method for increasing root mass in a plant, comprising:
    introducing the isolated transgenic nucleic acid molecule of any one of embodiment 1-4 or the vector of any one of embodiments 5-7 into a plant cell;
    allowing the plant cell to develop into a plant;
    expressing IPT7 from the TSS promoter in mesophyll cells of developing leaves of the plant, thereby increasing root mass in the plant by at least 10%, in comparison to a wild type plant.
16. The method of embodiment 15, further comprising measuring root mass in the plant and in some examples comparing the measured root mass to a root mass observed with a wild type plant.
17. The transgenic plant cell of embodiment 8, 11, or 12, the transgenic plant of embodiment 9, 11, 12, 13 or 14, transgenic plant part of embodiment 10, 11 or 12, or the method of any one of embodiments 15-16, wherein the transgenic plant, transgenic plant part, or transgenic plant cell further comprises one or more additional exogenous nucleic acid(s) encoding a protein(s) that confers upon the transgenic plant, transgenic plant part, or transgenic plant cell a desired trait, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.
18. The transgenic plant cell of embodiment 8, 11, 12, or 17 the transgenic plant of embodiment 9, 11, 12, 13, 14, or 17, transgenic plant part of embodiment 10, 11, 12, or 17, or the method of any one of embodiments 15-17, wherein the transgenic plant, transgenic plant part, or transgenic plant cell further comprises single locus conversion.

19. A method for breeding a plant with increased root mass, comprising:
    crossing the transgenic plant of any one of embodiments 9, 11, 12, 13, 14, 17 or 18 with a second plant;
    obtaining seed from the crossing;
    planting the seeds and growing the seeds to plants; and
    selecting from said plants those with increased root mass.

20. A method of generating a plant with increased root mass, comprising:
    crossing the transgenic plant of any one of embodiments 9, 11, 12, 13, 14, 17 or 18 with a second plant, thereby generating plants with increased root mass.

21. The transgenic plant part of any one of embodiments 10, 11, 12, 17, or 18, wherein the plant part is a protoplast, leaf, stem, root, root tips, anther, pistil, stamen, seed, embryo, pollen, ovule, microspore, protoplast, sporophyte, gametophyte, cotyledon, hypocotyl, flower, shoot, tissue, petiole, or meristematic cell.

22. The method of any one of embodiments 15-20, wherein the method increases root carbon sequestration by the plant, such as an increase of at least 20%.

23. An isolated recombinant nucleic acid molecule, comprising:
    a TPR-domain suppressor of STIMPY (TSS) promoter operably linked to an isopentenyl-transferase (IPT) coding sequence, wherein the IPT coding sequence is modified to encode an IPT peptide that comprises amino acids 1-29 and 298-329 of SEQ ID NO: 4 at the corresponding positions in the unmodified IPT coding sequence.

24. The IPT coding sequence of embodiment 23, wherein the unmodified IPT coding sequence is a homolog, homeolog, ortholog or paralog of an IPT7 coding sequence that encodes the peptide of SEQ ID NO: 4.

25. An isolated recombinant nucleic acid molecule, comprising:
    a TPR-domain suppressor of STIMPY (TSS) promoter operably linked to a modified isopentenyl-transferase 3 (IPT3) or a modified isopentenyl-transferase 4 (IPT4) coding sequence, wherein the coding sequence of the IPT3 or IPT4 nucleic acids have been modified to comprise nucleic acids encoding amino acids 1-29 and 298-329 of SEQ ID NO: 4 at the corresponding positions in unmodified IPT3 or IPT4 coding sequences, respectively.

26. An isolated recombinant nucleic acid molecule for expression in mesophyll cells in non-senescing leaves:
    a promoter operably linked to an isopentenyl-transferase 7 (IPT7) coding sequence, wherein the promoter drives the expression of IPT7 in the mesophyll cells in non-senescing leaves.

27. An isolated recombinant nucleic acid molecule for expression in mesophyll cells in non-senescing leaves comprising:
    a promoter operably linked to an isopentenyl-transferase (IPT) coding sequence, wherein the IPT coding sequence is modified to encode an IPT peptide that comprises amino acids 1-29 and 298-329 of SEQ ID NO: 4 at the corresponding positions in the unmodified IPT coding sequence; wherein the promoter drives the expression of the IPT coding sequence in the mesophyll cells in non-senescing leaves.

28. A vector comprising the isolated recombinant nucleic acid molecule of any one of embodiments 23-27.

29. A plant cell, plant tissue, plant part, seed or whole plant comprising the isolated recombinant nucleic acid molecule of any one of embodiments 23-27 or the vector of embodiment 28.

30. A method of modifying a nucleic acid sequence encoding an isopentenyl-transferase (IPT), said method comprising substituting or otherwise altering the nucleic acid sequence so that it encodes amino acids 1-29 and 298-329 of SEQ ID NO: 4 at the corresponding amino acid positions encoded by the unmodified IPT nucleic acid sequence.

31. The method of embodiment 30, wherein the unmodified IPT nucleic acid sequence is a homolog, homeolog, ortholog or paralog of an IPT7 nucleic acid sequence that encodes the peptide of SEQ ID NO: 4.

32. An isolated nucleic acid molecule comprising a TPR-domain suppressor of STIMPY (TSS) promoter.

33. The isolated transgenic nucleic acid molecule of embodiment 32, wherein the TSS promoter comprises at least 80%, at least 90%, at least 95%, at least 96%, at least 97%, at least 98%, at least 99%, or 100% sequence identity to SEQ ID NO: 1.

34. A vector comprising the isolated nucleic acid molecule of embodiment 32 or embodiment 33.

35. A plant cell, plant tissue, plant part, seed or whole plant comprising the isolated nucleic acid molecule of any one of embodiments 32-33 or the vector of embodiment 34.

36. A transgenic plant, transgenic plant tissue or transgenic plant part comprising:
    the isolated transgenic nucleic acid molecule of any one of embodiments 23-27 and 32-33;
    the vector of embodiment 28 or 34; or
    the plant cell of embodiment 29 or 35.

INCORPORATION BY REFERENCE

All references, articles, publications, patents, patent publications, and patent applications cited herein within the above text and/or cited below are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

EXAMPLES

Example 1. Materials and Methods

This example describes materials and methods used to generate the results described herein.

Figure 11:
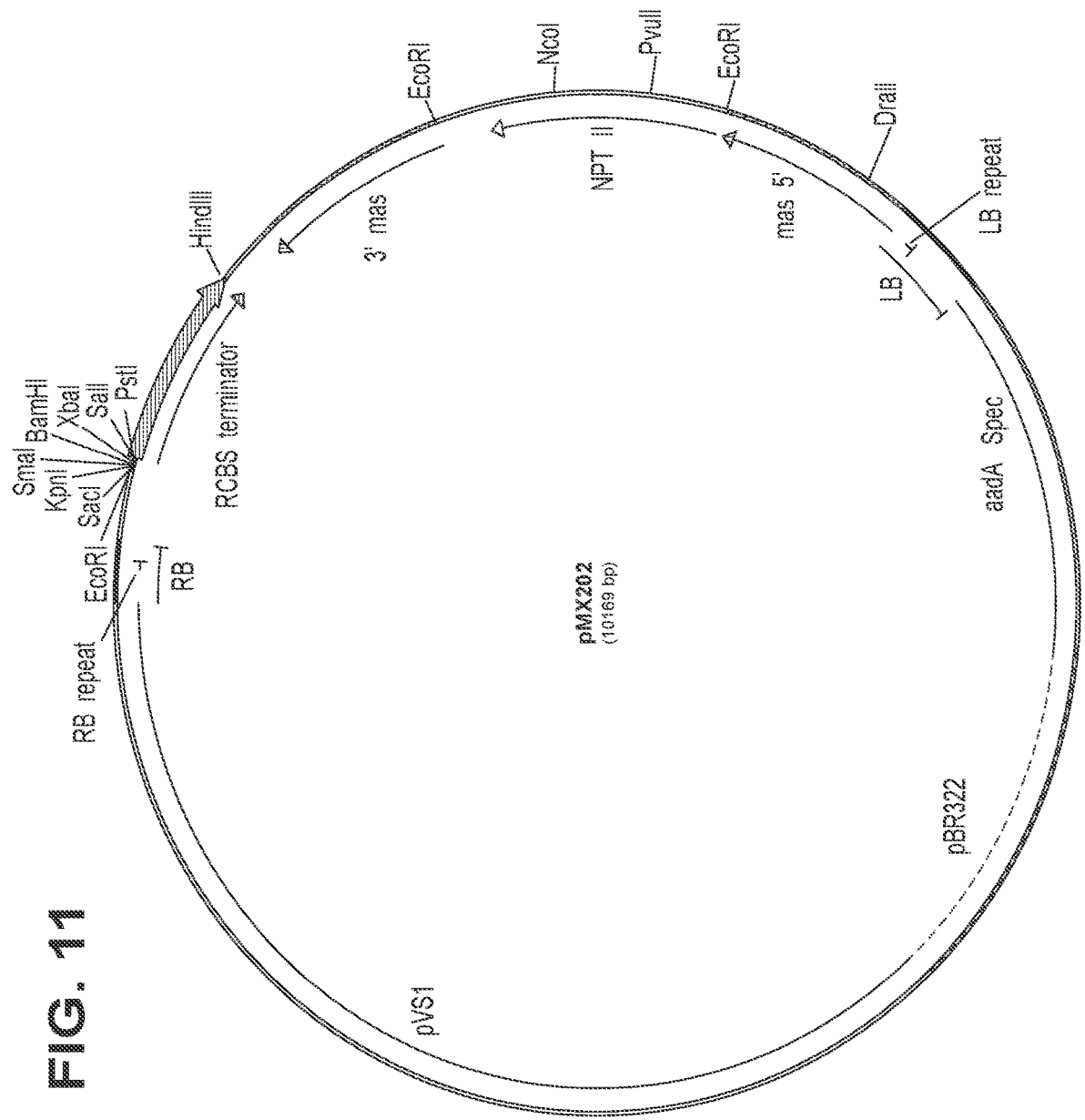
FIG. 11. A schematic drawing of the binary vector pMX202 that was used in plant transformation. For rice transformation, the kanamycin resistance gene was replaced with the hygromycin resistance gene hytII under the control of Z. maize mUB-1 promoter.

The 1643 bp TSS promoter (including its 5' untranscribed region) (SEQ ID NO: 1) was used to direct the ectopic IPT7 expression in the developing leaves. The TSS promoter and IPT7 cDNA fragments were cloned into the binary vector pMX202 (SEQ ID NO: 3, FIG. 11), which contains a pea RBCS terminator and a kanamycin resistant selectable marker in transgenic plants. The transgene was transformed into *Agrobacterium tumefaciens* strain GV3101.

For *Arabidopsis* transformation, wildtype *Arabidopsis* Col-0 plants were transformed using floral dipping. T1 transgenic *Arabidopsis* plants were selected with 50 μg/ml kanamycin on ½ LS-agar medium, and single insertion homozygous lines were selected in subsequent generations based on both the segregation ratio and transgene expression levels. IPT7 expression levels were measured using RT-qPCR in seedlings that were 7 days post germination. Both soil and hydroponically grown plants were grown in long-day conditions (16 hr day/8 hr night), under approximately 120 µmol m$^{-2}$ sec$^{-1}$ light at 22° C.

The same plasmid as described above was transformed into *N. benthmiana, N. tabacum*, and *B. napus* through *Agrobacterium tumefaciens* mediated transformation. Specifically, the GV3101 strain containing the said plasmid was used to infect seedling tissue, followed by callus induction and plant regeneration. Transgenic T1 plants were selected with kanamycin on growth medium and confirmed with PCR-based genotyping for the presence of NPTII gene, which confers kanamycin resistance.

For rice transformation, the kanamycin resistance gene (NPTII) in pMX202-TSS-IPT7 was replaced with the hygromycin resistance gene hytII under the control of *Z. maize* mUB-1 promoter. The resulting plasmid, XW359, was transformed into *Agrobacterium tumefaciens* strain EHA105, which was used to infect calli generated from wildtype *Oryza sativa japonica* seeds. Regenerated transgenic plants were selected with hygromycin on growth medium and confirmed with PCR-based genotyping for the presence of hytII gene.

Example 2. TSS Promoter is Active in Growing Green Tissues

IPT7 has been ectopically expressed in *Arabidopsis* and other plant species under different promoters by several groups. When it was expressed in the shoot meristem and leaf primordia, it led to altered leaf morphology and meristem activities. When it was expressed in mature leaves, it resulted in delayed senescence. Additionally, IPT7 expression in cambium leads to increased cell proliferation, which is the expected outcome of ectopic IPT7 expression in meristematic tissues.

Here, the TSS promoter from *Arabidopsis thaliana* (SEQ ID NO: 1) was used to drive the expression of a GUS reporter in *Arabidopsis* as set forth in Example 1.

FIGS. 1A-J provide a detailed time course of TSS promoter activities. Strong GUS activities were detected in the cotyledons and young green tissues. It becomes weak in older leaves and is excluded from the shoot meristematic region and the root.

The native TSS mRNA is detected only in the mesophyll cells of young leaves and is excluded from the shoot meristem and leaf primordial (FIG. 1A) (Metabolic sugar signal promotes *Arabidopsis* meristematic proliferation via G2. Skylar A, Sung F, Hong F, Chory J, Wu X. Dev Biol. 2011 Mar. 1; 351(1):82-9. doi: 10.1016/j.ydbio.2010.12.019. Epub 2010 Dec. 23. PMID: 21185286). TSS: GUS activities are only found in young leaves, not in mature leaves. In addition, TSS promoter is active in the inflorescence and throughout embryogenesis. Based on these findings, we concluded that the TSS promoter is active mostly in the green sink tissues only and is excluded from the shoot meristematic region.

In addition to the TSS promoter, we have also expressed IPT7 under the green tissue-specific AtRBCS2b promoter. Plants carrying RBCSp::IPT7 accumulated high levels of anthocyanin, had severe reductions in fertility, and delayed senescence by more than one month compared to the wild type. Therefore, based on all of these observations by both us and others, we hypothesized that the expression pattern of the TSS promoter is the key factor in achieving the root biomass increase without disrupting the normal developmental processes achieved.

The TSS promoter GUS activity time course showed mesophyll expression that is consistent with the in situ hybridization result. Furthermore, there is a clear exclusion of GUS activity from the vasculature as shown in FIG. 1B. We did not observe IPT7 expression in the cambium or increased cell proliferation with the phenotype of the TSS:IPT7 transformed plants.

Example 3. TSS:IPT7 Increases Root Growth

The TSS promoter from *Arabidopsis thaliana* (SEQ ID NO: 1) was used to drive the expression of IPT7 (SEQ ID NO: 2) in *Arabidopsis* as set forth in Example 1.

Figure 2:
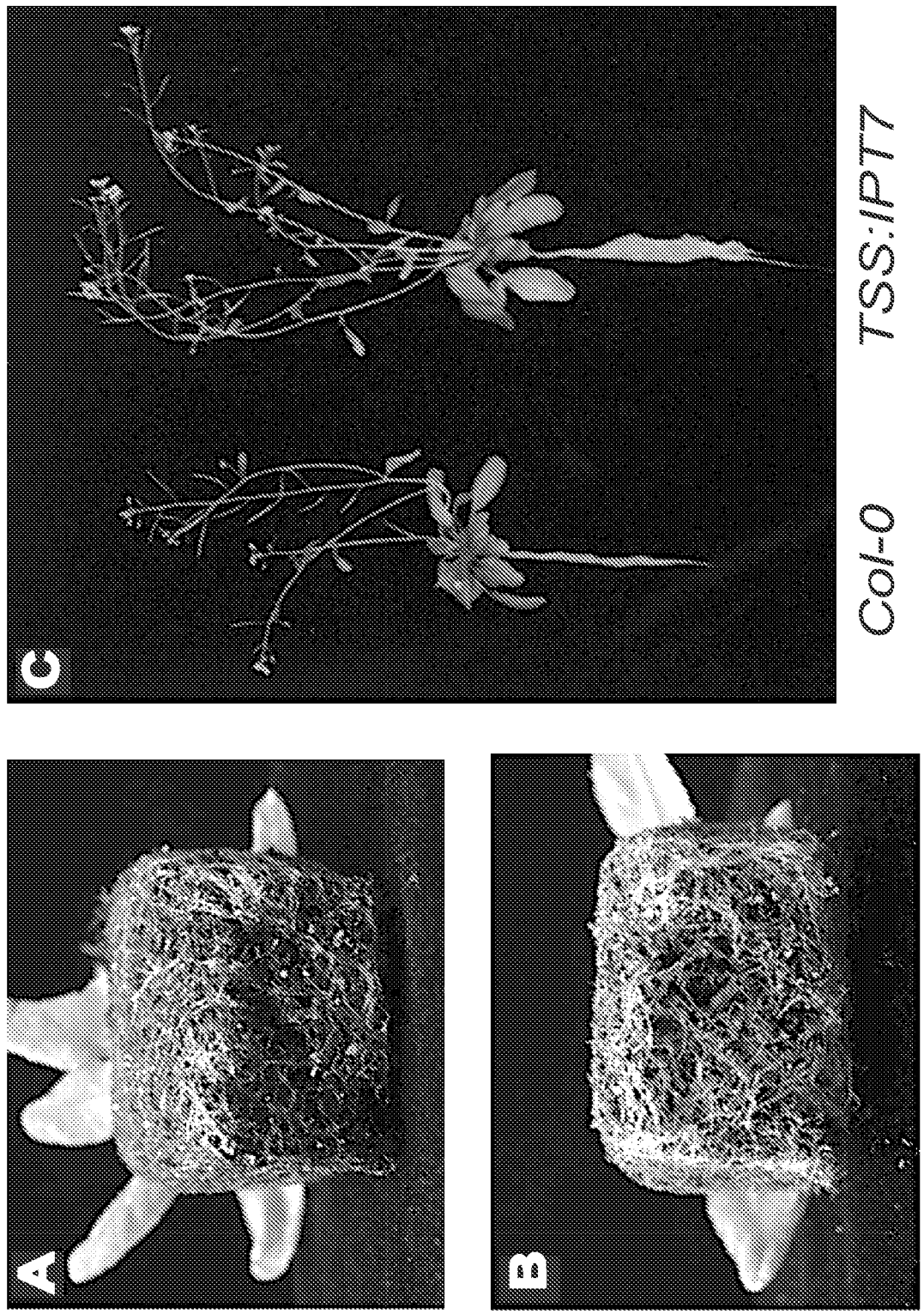
FIGS. 2A-2C. TSS:IPT7 leads to enhanced root growth in *Arabidopsis* plants. Representative five-week-old soil grown (A and B) and hydroponically grown (C) Col-0 (i.e., wildtype) (A and left in C) and T1 plants carrying TSS:IPT7 (B and right in C) are shown. The ectopic IPT7 expression resulted in visibly more roots under both growth conditions.

Following introduction of pMX202-TSSp-IPT7 into *Arabidopsis*, plants were grown in soil or hydroponically. As shown in FIGS. 2A-C, soil-grown and hydroponically grown TSS:IPT7 *Arabidopsis* plants had more roots than controls (Col-0) under both growth conditions.

Example 4. TSS:IPT7 Enhances Root Growth

The TSS promoter from *Arabidopsis thaliana* (SEQ ID NO: 1) was used to drive the expression of IPT7 (SEQ ID NO: 2) in *Arabidopsis* as set forth in Example 1.

Following introduction of pMX202-TSSp-IPT7 into *Arabidopsis*, plants were grown in soil or hydroponically.

Figure 3:
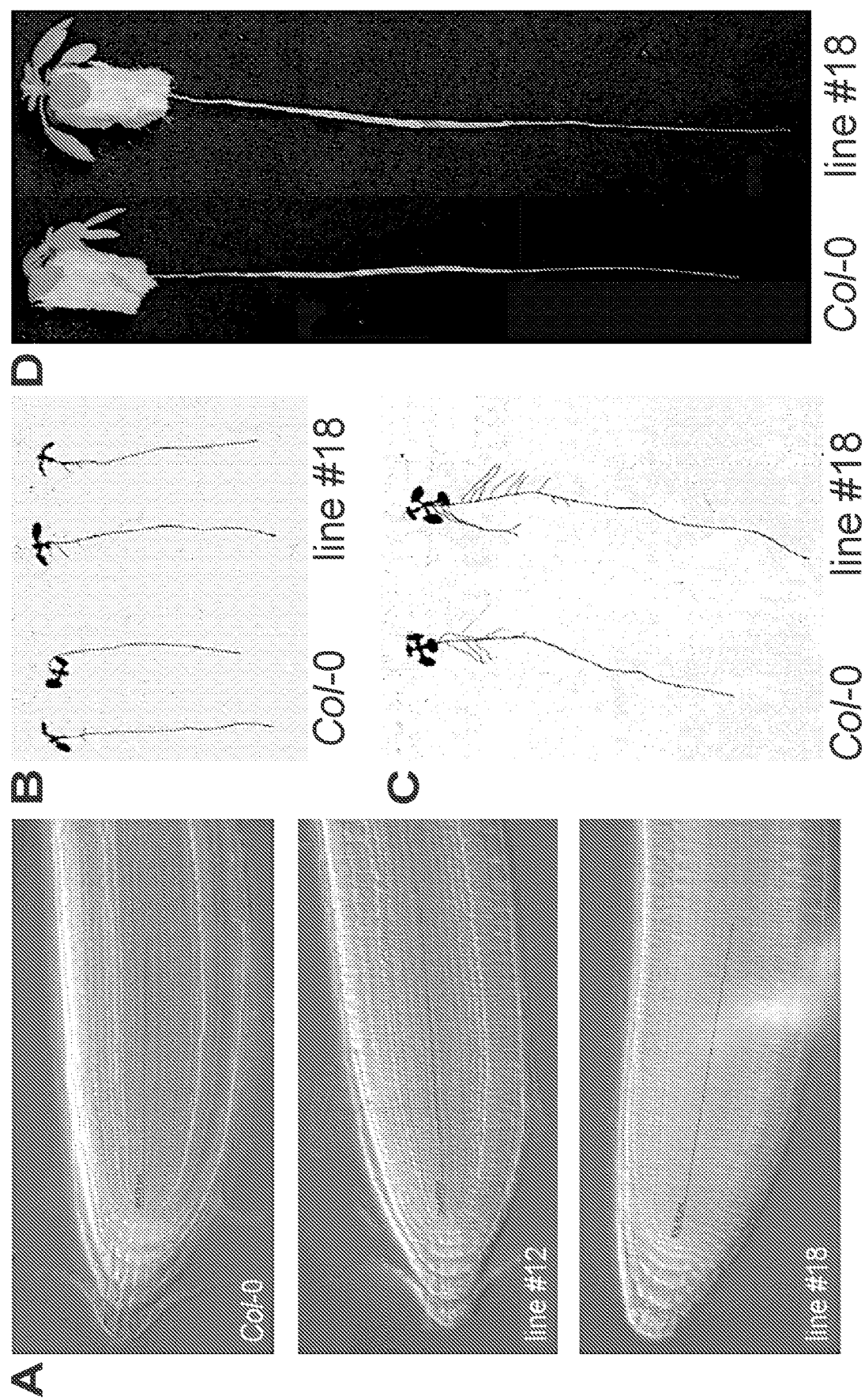
FIGS. 3A-3D. TSS:IPT7 enhances root growth during early development in *Arabidopsis*. (A) Images of the primary root meristematic zone of control (Col-0; wildtype) and two lines of TSS:IPT7 plants (i.e., line #12 and line #18). There is an 18% increase in the length of the meristematic zone (marked by the red line) in TSS:IPT7. (B) 7-day-old vertically grown seedlings of Col-0 and TSS:IPT7 line #18. The average root length is 2.55 cm for Col-0 (n=13) and 2.97 cm for line #18 (n=13). (C) Representative 10-day-old vertically grown seedlings of Col-0 and line #18. The TSS:IPT7 seedlings have both longer primary roots and more lateral roots. (D) 3-week-old hydroponically grown plants of Col-0 and line #18. The average root dry weight is 1.0 mg per Col-0 plant (n=18) and 1.38 mg per plant in line #18 (n=18).

As shown in FIG. 3, TSS:IPT7 *Arabidopsis* plants have a greater sized primary root meristematic zone than control plants (Col-0). For example, the TSS:IPT7 plants as compared to the control plants (Col-0) have enlarged root meristematic zones with an approximately 18% increase in the length of the meristematic zone at the seedling stage.

FIGS. 3B-C provide root biomass phenotypic observations and measurements. In summary, we observed increased primary root length 7 days after the seeds were exposed to light (FIG. 3B) and increased lateral root emergence by 10 days (FIG. 3C). This resulted in a measurable increase in root dry weight by 3 weeks (FIG. 3D).

Additionally, root suberin content has been measured in hydroponically grown mature wildtype and TSS:IPT7 plants. The ectopic IPT7 expression does not change the percentage of suberin per unit dry mass. Therefore, based on the increased root mass, this transgene also leads to approximately 20% increase in root suberin content in each plant.

Example 5. TSS:IPT7 Increases Root Biomass During Late Stages of Development

The TSS promoter from *Arabidopsis thaliana* (SEQ ID NO: 1) was used to drive the expression of IPT7 (SEQ ID NO: 2) in *Arabidopsis* as set forth in Example 1.

Following introduction of pMX202-TSSp-IPT7 into *Arabidopsis*, plants were grown hydroponically. As shown in FIG. 4A, a significant increase (approximately 18% to 24%) in root biomass was detected in hydroponically grown plants when the plants are near maturity (6-weeks old). Detailed measurements are included in the figure description for FIG. 4A. This percentage of increase is consistent with the earlier stage measurements discussed in Example 4 and shown in FIG. 3.

As shown in FIG. 4B, this increase in root biomass becomes more pronounced as the plants age further (7-weeks old).

Example 6. TSS:IPT7 does not Reduce Above-Ground Growth

The TSS promoter from *Arabidopsis thaliana* (SEQ ID NO: 1) was used to drive the expression of IPT7 (SEQ ID NO: 2) in *Arabidopsis* as set forth in Example 1.

Figure 5:
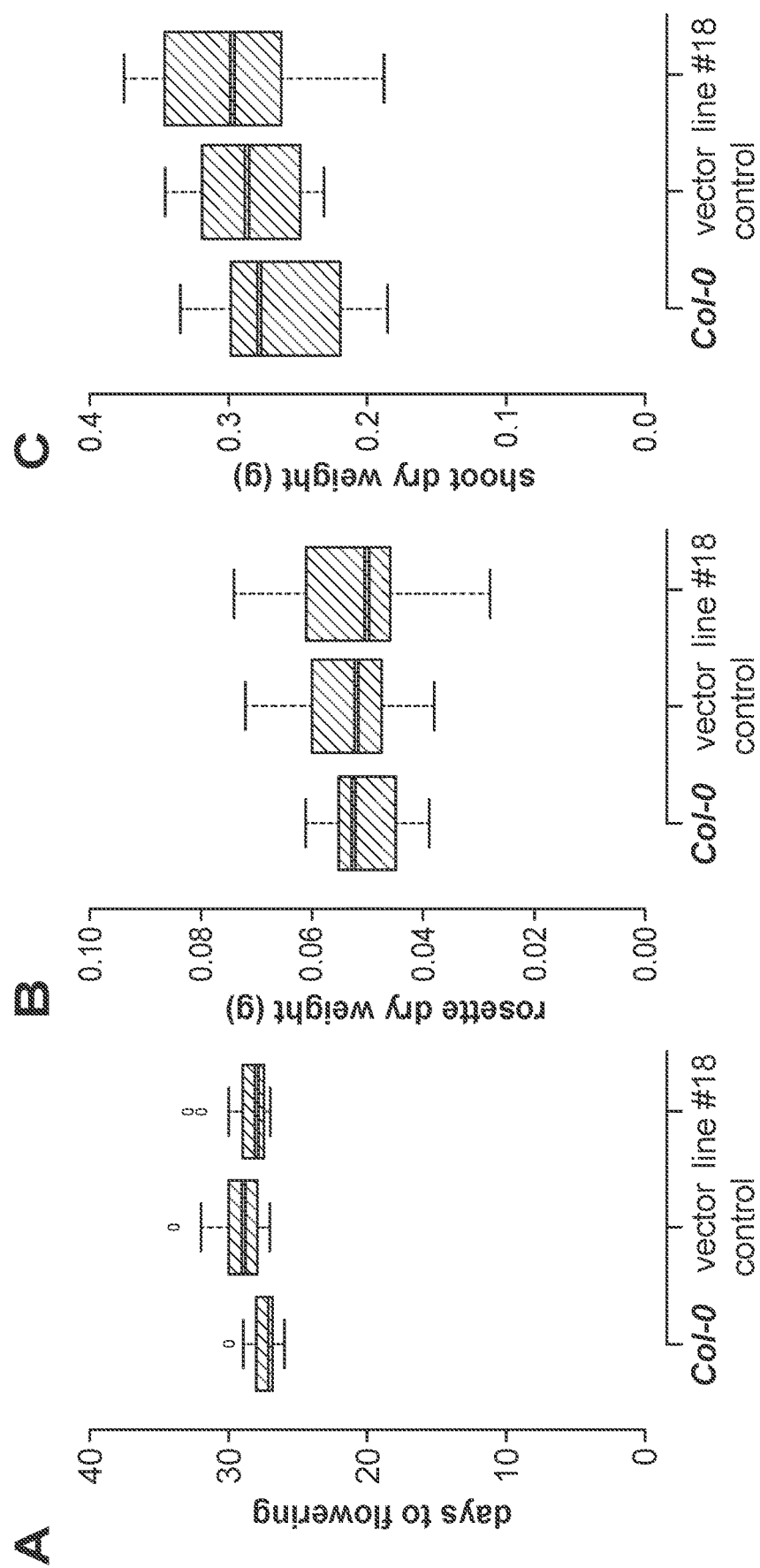
FIGS. 5A-5C. TSS:IPT7 expression has little effect on above-ground growth in *Arabidopsis*. Flowering time (A), rosette (B) and inflorescence and seed (C) dry weight of mature plants were measured in soil grown plants. TSS:IPT7 line #18 is shown here as a representative example. Col-0 is the wildtype.

Following introduction of pMX202-TSSp-IPT7 into *Arabidopsis*, plants were grown in soil. As shown in FIGS. 5A-C, TSS:IPT7 transgenic plants (line #18) have about the same amount of above ground growth as control Col-0 and vector control DL06. The same was found for TSS:IPT7 line #18, which has low IPT7 expression levels, but the strongest root phenotype as shown in FIG. 4. Days to flowering is counted from the day of sowing to first open flower. In some trials, line #18 plants also showed a slight increase in shoot biomass (data not provided).

Example 7. TSS:IPT7 Expression is Well Tolerated

A common issue with ectopic expression is transgene silencing. Following introduction of pMX202-TSSp-IPT7 into *Arabidopsis* as set forth in Example 1, IPT7 expression was tracked through four generations of transgenic plants in multiple independent transgenic lines. As shown in FIGS. 6A-B, no reduction of IPT7 expression level was observed on a per line or per generation basis. For each of the graphs in FIG. 6A and FIG. 6B the first entry on the X-axis is the control Col-0 (wildtype) and the second entry on the X-axis is the vector control.

Example 8. IPT7 Compared to Other *Arabidopsis* IPT Genes in Transformed Plants We have evidence that, when compared to other *Arabidopsis* IPT genes in the same family, IPT7 is unique in its function when expressed in the abovementioned tissue.

Specifically, IPT7 is a member of a seven (IPT)-gene sub-family in *Arabidopsis*. Their proposed function is to catalyze the first and rate-limiting step of cytokinin biosynthesis, which occurs in the plastids. However, it was reported in 2004 that, unlike other members of this gene family, IPT7 protein has an N-terminal mitochondria transit peptide (amino acids 1-29) (Distinct isoprenoid origins of cis- and trans-zeatin biosyntheses in *Arabidopsis*. Kasahara H, Takei K, Ueda N, Hishiyama S, Yamaya T, Kamiya Y, Yamaguchi S, Sakakibara H. J Biol Chem. 2004 Apr. 2; 279(14):14049-54. doi: 10.1074/jbc.M314195200. Epub 2004 Jan. 15. PMID: 14726522). Based on this finding, it was proposed that IPT7 may also be involved in the ubiquinone biosynthesis pathway in the mitochondria. Recently, we were able to confirm the presence of the mitochondria transit peptide using a TSS:IPT7:GFP transgene in *Arabidopsis*. A blast search revealed that IPT proteins with the mitochondria transit peptide are only found in the plant family of Rosids.

The Rosids are members of a large clade of flowering plants, containing about 70,000 species, more than a quarter of all angiosperms. The clade is divided into 16 to 20 orders, depending upon circumscription and classification. These orders, in turn, together comprise about 140 families. See, e.g., Angiosperm Phylogeny Group, 2016, Botanical Journal of the Linnaean Society 181(1):1-20 and Wang et al., 2009, Proceedings of the National Academy of Sciences 106(10): 3853-3858.

The IPT proteins within the same subfamily in *Arabidopsis* are highly conserved in their catalytic domain, which encompasses the majority of the peptides. The differences lie in the short stretches of amino acids in their N- and C-termini. The alignment was published in: Identification of plant cytokinin biosynthetic enzymes as dimethylallyl diphosphate:ATP/ADP isopentenyltransferases. Kakimoto T. Plant Cell Physiol. 2001 July; 42(7):677-85. doi: 10.1093/pcp/pce112. PMID: 11479373. In addition to the N-terminal mitochondria transit peptide, we have preliminary data suggesting that the C-terminal amino acids are also important for IPT7 function. The IPT7 amino acid sequence is provided in SEQ ID NO:4 and FIG. 12. In FIG. 12, the N-terminus transit peptide amino acids are highlighted in yellow (amino acids positions 1-29) and the unconserved C-terminus amino acids between IPT7 and other IPT proteins of the same subfamily are shown in red (amino acids positions 298-329).

In addition to IPT7, we expressed IPT3 (protein sequence disclosed by GenBank® Accession No. OAP02216.1) and IPT4 (protein sequence disclosed by GenBank® Accession Nos. OAO99927.1, NP 194196.1, Q9SB60.1 and AEE84938.1) under the TSS promoter in *Arabidopsis*. TSS:IPT4 caused complete seedling lethality. TSS:IPT3 was not tolerated by the plants and was silenced by the time the plants reached T3 generation. This is another indication that IPT7 is unique in its function, when compared to other IPTs in the same subfamily.

By swapping the terminal sequences between IPT7 and the other IPTs one skilled in the art can achieve the same effects as provided in the instant disclosure. For example, by substituting the nucleic acids coding for the amino acids of the N-terminus and C-terminus of IPT7 (FIG. 12) for the corresponding sequences of IPT3 or IPT4, one skilled in the art can then use the modified IPT4 nucleic acid sequence in a binary vector, for example pMX202, to produce transformed plants with increased root mass and/or an increased ability to sequester carbon in its roots. While pMX202 utilizes the TSS promoter to drive IPT expression, the modified IPT can be driven by any promoter that results in ectopic IPT expression, particularly wherein the ectopic IPT expression occurs in the mesophyll.

Example 9. TSS:IPT7 and TSS:GUS Expression in *Nicotiana* Species

We transformed TSS:IPT7 and TSS:GUS into two species of tobacco plants using the basic procedures set forth in Example 1.

Figure 7:
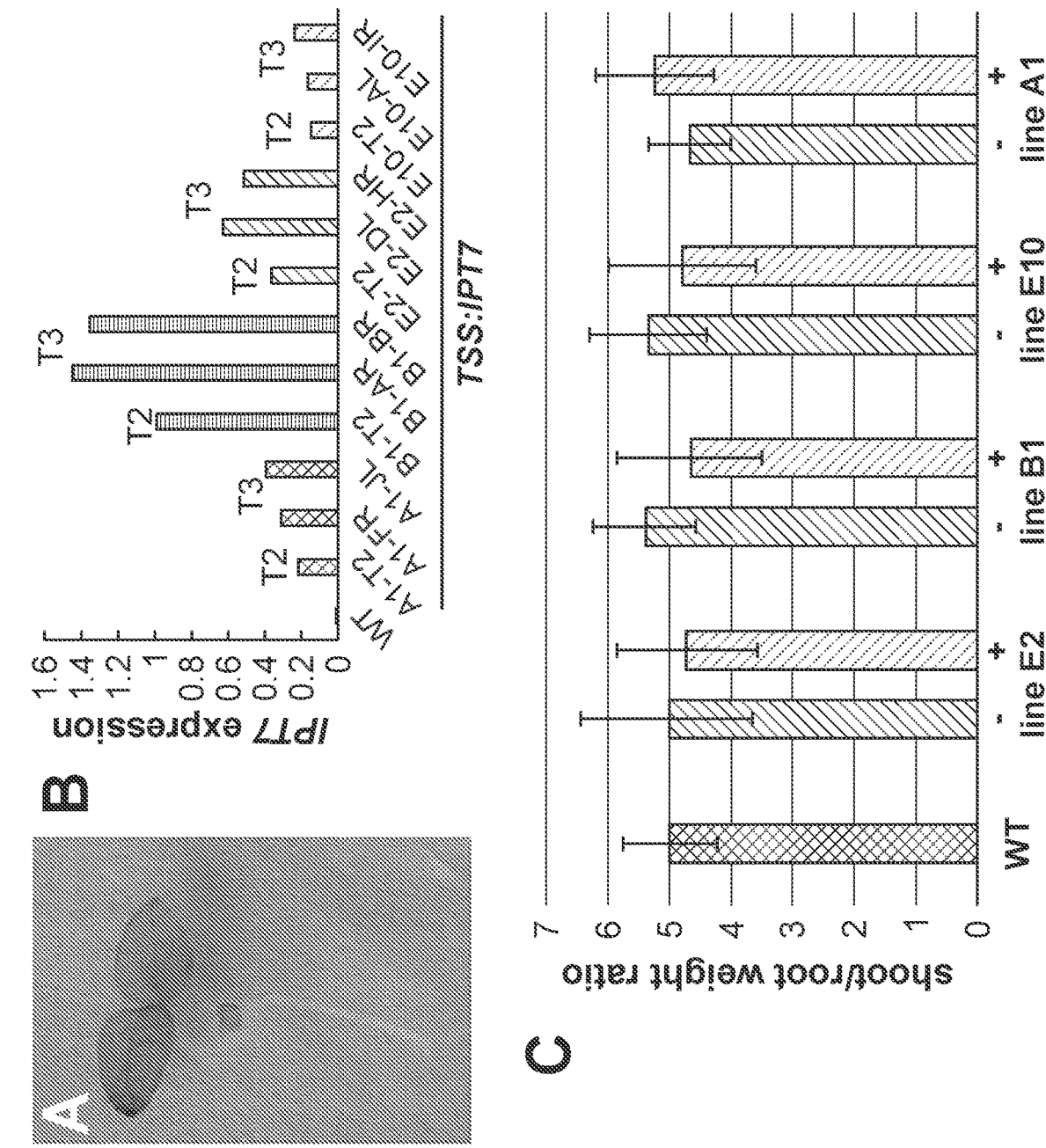
FIGS. 7A-7B. TSS:IPT7 enhances root growth in transgenic *Nicotiana benthamiana*. (A) TSS promoter GUS activity (in dark color) in an *N. benthamiana* seedling. It showed the same expression pattern as what was observed in *Arabidopsis* seedlings. (B) Ectopic IPT7 expression levels in four independent single insertion *N. benthamiana* lines carrying TSS:IPT7 (i.e., A1, B1, E2 and E10). IPT7 levels were measured using RT-qPCR and data was normalized to a housekeeping gene. For each line, the T2 population and two T3 homozygous siblings were included in the analyses. WT=wildtype, the control plant. (C) The homozygous T3 *N. benthamiana* plants from each of the four lines (light color bars, marked with +) were grown side-by-side with their non-transgenic siblings that segregated out from the T2 populations (dark color bars, marked with −). The nontransgenic siblings serve as the controls within each line. WT=wildtype. Tissue was harvested at the "first open flower" stage, which is approximately five and half weeks after sowing. The average total plant dry weight for each genotype is: WT 6.36 g, line E2 (−) 8.18 g, line E2 (+) 7.66 g, line B1 (−) 8.40 g, line B1 (+) 8.24 g, line E10 (−) 8.46 g, line E10 (+) 7.86 g, line A1 (−) 6.98 g, line A1 (+) 6.91 g. The shoot-to-root dry weight ratio is used to evaluate the growth and carbon partition pattern within each genotype. Of the four lines included in the study, three of them, E2, B1, and E10, showed a decrease in their shoot/root weight ratio in the presence of the transgene in comparison to their nontransgenic siblings, which indicates enhanced root growth.
Figure 8:
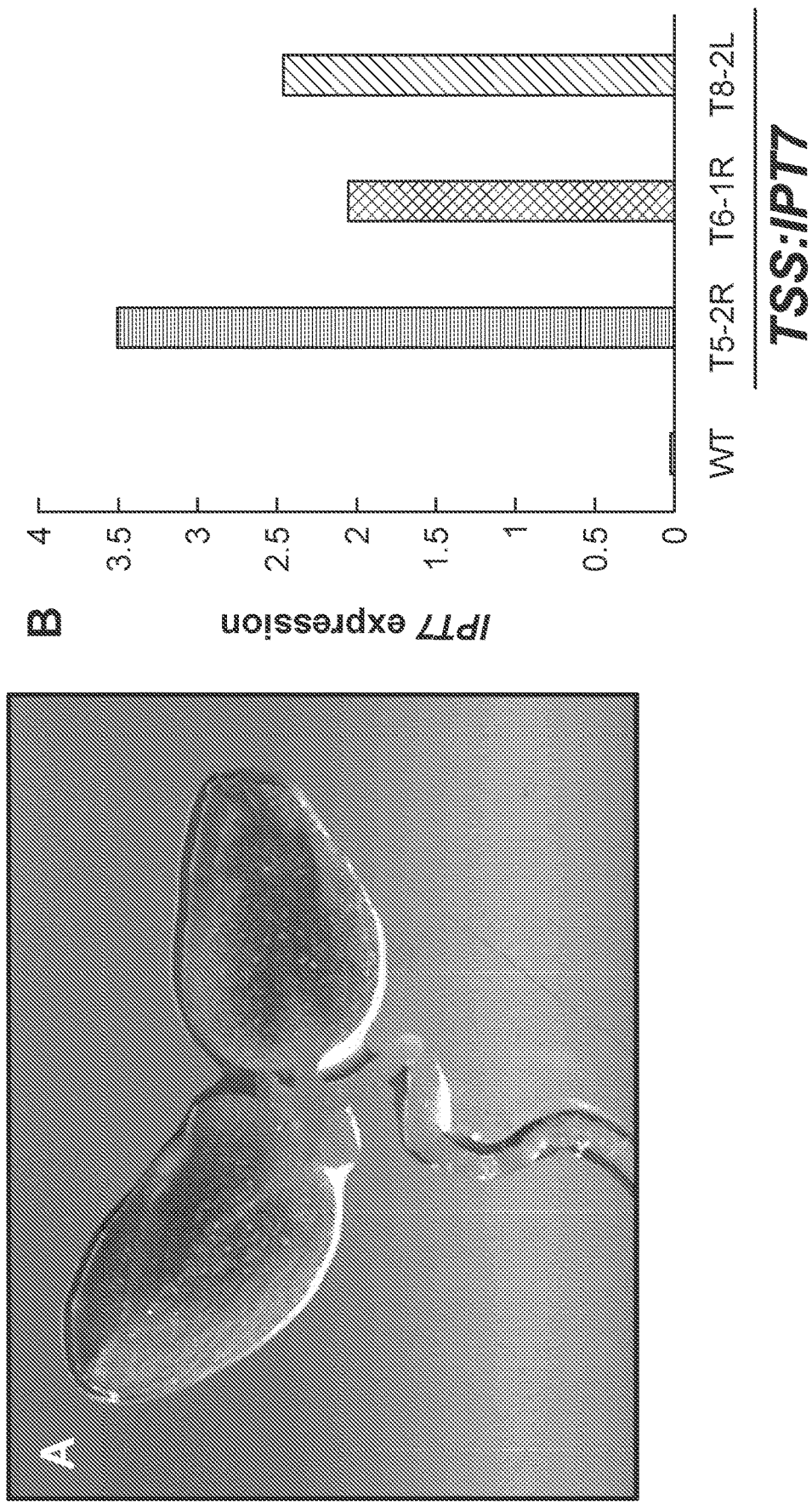
FIGS. 8A-8B. TSS:IPT7 expression in transgenic *Nicotiana tabacum*. (A) TSS promoter GUS activity (in dark color) in an *N. tabacum* seedling. It showed a similar pattern as what was observed in *Arabidopsis* seedlings. (B) Ectopic IPT7 expression levels in three independent T3 single-insertion homozygous *N. tabacum* lines carrying TSS:IPT7 (i.e., T5, T6 and T8). IPT7 levels were measured using qRT-PCR and data was normalized to a housekeeping gene. WT=wildtype, the control plant.

*Nicotiana benthamiana*: This is a wild species in the *Nicotiana* genus that is native to Australia. We established T3 homozygous populations from four independent single-insertion lines carrying TSS:IPT7. The promoter-GUS activity staining and IPT7 expression levels are shown in FIGS. 7A-B, respectively.

Based on the early increase in *Arabidopsis* root biomass, we harvested the tissue at the "first open flower" stage for our first round of phenotyping. As shown in FIGS. 7C, three of the four lines tested showed decreased shoot-to-root dry weight ratio in comparison to their nontransgenic counterparts. This indicates enhanced root growth due to the presence of TSS:IPT7. Further evaluations in more mature plants will be conducted in these three lines to determine their root biomass at a later stage.

*Nicotiana tabacum*: This is the common tobacco species that includes that used for smoking tobacco. We have established T3 homozygous populations from three independent single-insertion lines. The promoter-GUS activity staining and IPT7 expression levels are shown in FIGS.

8A-B, respectively. We will collect tissue for biomass measurement in a similar manner as with *N. benthamiana*.

Example 10. TSS:IPT7 Expression in *Brassica napus*

We transformed TSS:IPT7 into *Brassica napus* plants using the basic procedures set forth in Example 1.

Figure 9:
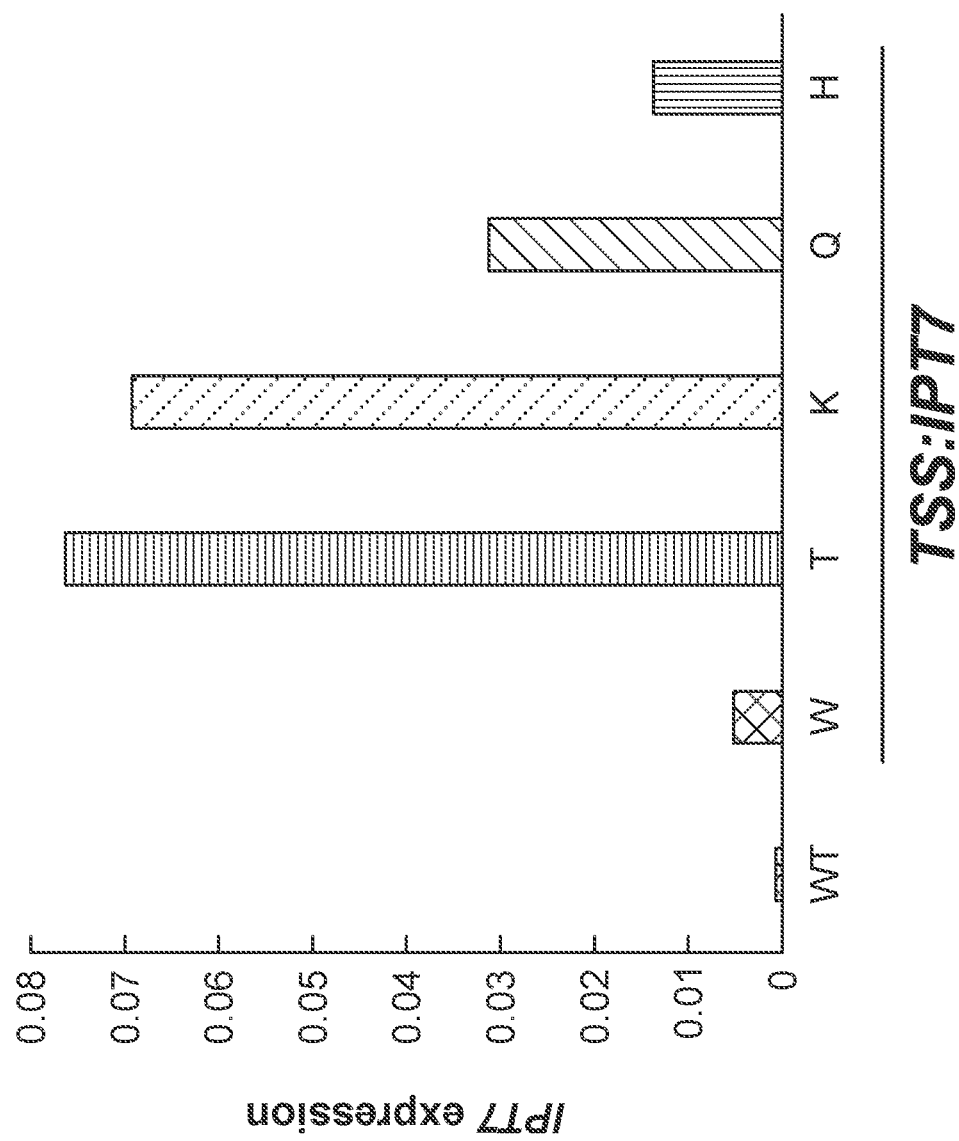
FIG. 9. TSS:IPT7 expression in transgenic *Brassica napus*. Ectopic IPT7 expression levels in the T2 populations of five independent single-insertion lines carrying TSS:IPT7 (i.e., W, T, K, Q and H) were measured using qRT-PCR. Data was normalized to a housekeeping gene. WT=wildtype, the control plant.

We identified five single-insertion TSS:IPT7 lines from the T2 populations. Their IPT7 expression levels are shown in FIG. 9. The TSS promoter expression pattern is expected to be very similar to what we observed in *Arabidopsis*, because these two species are closely related and the promoter-GUS data we have from the tobacco species, which are much further from *Arabidopsis* evolutionarily, appear very similar to *Arabidopsis* pattern.

We are currently in the process of identifying T3 homozygous plants from four of these T2 populations. These plants will be used for *B. napus* phenotyping and measurements will be obtained for dry weight data.

Example 11. TSS:IPT7 Expression in *Glycine max*

We transformed TSS:IPT7 into *Glycine max* (i.e., soybean) plants by enlisting the service of a plant transformation facility.

We are planning to generate and test plants originating from four to six T0 populations of TSS:IPT7 in soybean.

Example 12. TSS:IPT7 Expression in *Oryza sativa japonica*

We transformed TSS:IPT7 into *Oryza sativa japonica* (i.e., rice) plants using the basic procedures set forth in Example 1.

Prior research by us and others has demonstrated that very few promoters are able to stay active across the dicot-monocot boundary.

Figure 10:
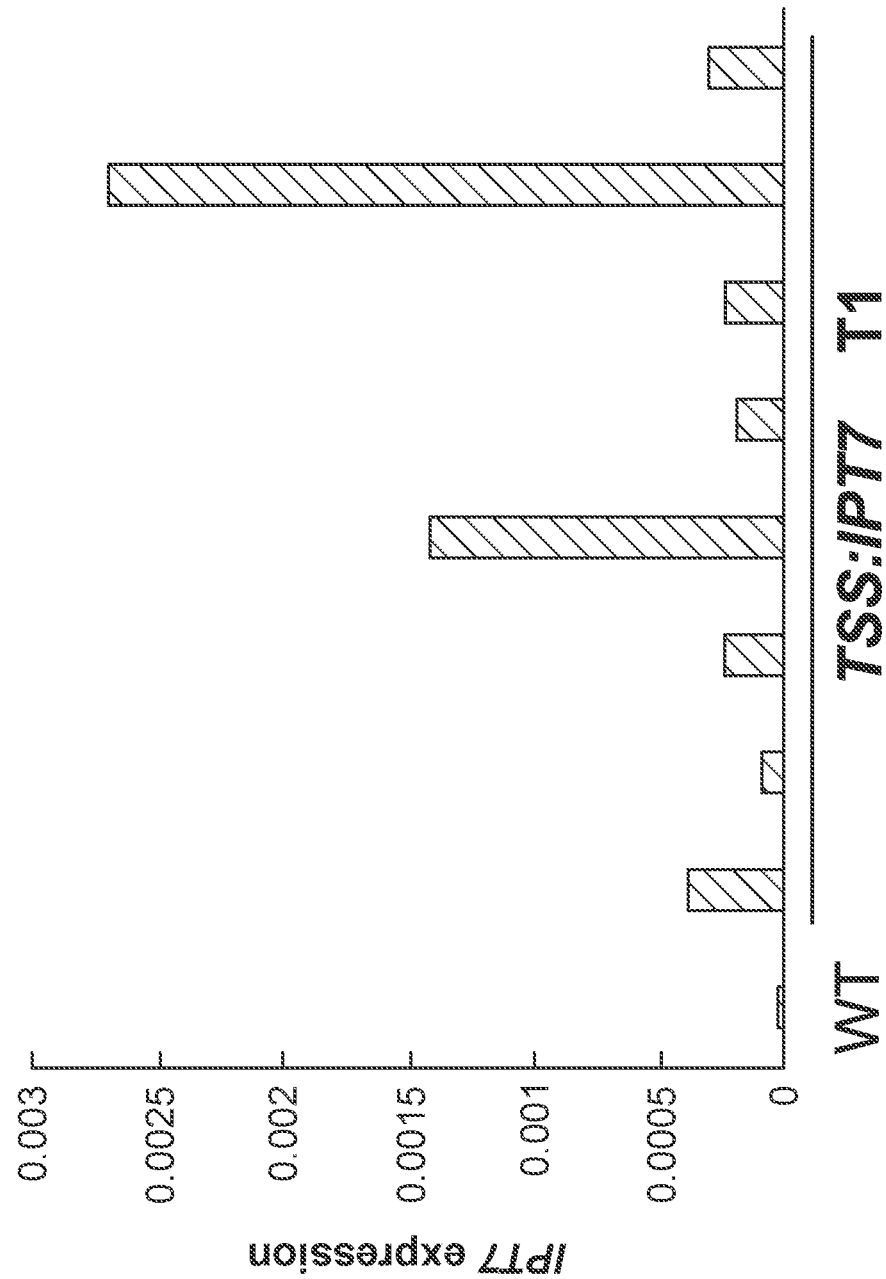
FIG. 10. TSS:IPT7 expression in *Oryza sativa japonica* T1 transgenic lines. Ectopic IPT7 expression levels were measured in single leaves collected from eight independent T1 transgenic lines using qRT-PCR. Data was normalized to a housekeeping gene. WT=wildtype, the control plant.

We generated rice transgenic lines carrying TSS:IPT7. RT-PCR results from leaf samples collected from eight of the rice T1 lines showed that the TSS promoter is active in the young leaves of rice (FIG. 10), which is similar to that in *Arabidopsis*. These results have been confirmed in the T1 transgenic rice lines carrying TSS: GUS.

We are in the process of generating a more detailed promoter activity map in the T2 TSS: GUS rice plants.

The T1 TSS:IPT7 rice plants were healthy and had good seed set. In comparison, most of the AtRBCSp::IPT7 rice transgenic lines had much reduced seed set, a phenotype that mimics what we observed in *Arabidopsis* as set forth in Example 2. These results suggest that the *Arabidopsis* IPT7 protein is active in rice. We expect to see an increase in root biomass in rice plants with TSS:IPT7 as compared to the control, wildtype plants.

Progress is underway to identify single-insertion lines in the T2 populations, which will be propagated to T3 generation for phenotyping and dry weight measurement.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A recombinant nucleic acid molecule, comprising: a tetratricopeptide repeat (TPR)-domain suppressor of STIMPY (TSS) promoter operably linked to an isopentenyl-transferase 7 (IPT7) coding sequence, wherein the TSS promoter comprises at least 95% sequence identity to SEQ ID NO: 1, and the IPT7 coding sequence encodes a protein comprising at least 85% sequence identity to SEQ ID NO: 4; and wherein the TSS promoter allows expression of the IPT7 coding sequence in mesophyll cells.

2. The recombinant nucleic acid molecule of claim 1, wherein the IPT7 coding sequence comprises at least 80% sequence identity to SEQ ID NO: 2.

3. The recombinant nucleic acid molecule of claim 1, wherein the IPT7 coding sequence encodes a protein comprising at least 90% sequence identity to SEQ ID NO: 4.

4. A vector comprising the recombinant nucleic acid molecule of claim 1.

5. The vector of claim 4, wherein the vector is a plasmid vector not found in plants.

6. The vector of claim 4, wherein the vector comprises at least 80% sequence identity to SEQ ID NO: 3.

7. A transgenic plant, plant part, or plant cell, comprising the recombinant nucleic acid molecule of claim 1.

8. The transgenic plant, plant part, or plant cell of claim 7, wherein the IPT protein is ectopically expressed in the plant, the plant part thereof, or the plant cell thereof, thereby increasing root biomass of the plant as compared to a control plant.

9. The transgenic plant, plant part, or plant cell of claim 7, wherein the plant is a dicot.

10. The transgenic plant, plant part, or plant cell of claim 9, wherein the dicot is a canola, a tobacco, a legume, a daisy, a mint, a lettuce, a tomato, a radish, an alfalfa, a pennycress, a clover, a rose bush, a sunflower, or a squash.

11. The transgenic plant, plant part, or plant cell of claim 7, wherein the plant has enlarged root meristem zones with at least 10% increase in the length of root meristematic zones at seedling stage as compared to a wild-type plant.

12. The transgenic plant, plant part, or plant cell of claim 7, wherein the transgenic plant has at least 10% greater root biomass as compared to a wild-type plant.

13. A method for increasing root mass in a plant, comprising:
    introducing the recombinant nucleic acid molecule of claim 1 into a plant cell; and
    allowing the plant cell to develop into a plant;
    wherein the plant exhibits at least 10% increase in root mass in comparison to a wild-type plant.

14. The method of claim 13, wherein the transgenic plant, plant part, or plant cell, further comprises one or more additional exogenous nucleic acid(s) encoding a protein(s) that confers a desired trait upon the transgenic plant, plant part, or plant cell, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.

15. The method of claim 13, wherein the transgenic plant, plant part, or plant cell further comprises single locus conversion.

16. A method for producing a plant with increased root mass as compared to a control plant, comprising:
    crossing the transgenic plant of claim 7 with a second plant;
    obtaining seeds from the crossing;
    planting the seeds to produce plants; and
    selecting from said plants those with increased root mass and comprising the recombinant nucleic acid molecule, thereby producing the plant with increased root mass.

17. A method of generating a plant with increased root mass as compared to a control plant, comprising:
    crossing the transgenic plant of claim 7 with a second plant, thereby generating the plants with increased root mass, wherein the plant with increased root mass comprises the recombinant nucleic acid molecule.

18. A plant produced by the method of claim 13, wherein the plant increases root carbon sequestration by at least 20% when compared to a wild-type plant.

19. The plant, the plant part thereof, or the plant cell thereof of claim 7, wherein the plant has at least 15% increase in root suberin content when compared to a wild-type plant.

* * * * *